United States Patent
Tour et al.

(10) Patent No.: US 12,329,780 B2
(45) Date of Patent: Jun. 17, 2025

(54) ACUTE AND CHRONIC MITOCHONDRIAL ELECTRON TRANSPORT CHAIN DYSFUNCTION TREATMENTS AND GRAPHENIC MATERIALS FOR USE THEREOF

(71) Applicants: WILLIAM MARSH RICE UNIVERSITY, Houston, TX (US); BOARD OF REGENTS, THE UNIVERSITY OF TEXAS SYSTEM, Austin, TX (US); BAYLOR COLLEGE OF MEDICINE, Houston, TX (US); HOUSTON METHODIST RESEARCH INSTITUTE, Houston, TX (US); THE UNITED STATES GOVERNMENT, Washington, DC (US)

(72) Inventors: James M. Tour, Bellaire, TX (US); Lizanne Nilewski, La Jolla, CA (US); William Sikkema, Langley (CA); Kimberly Mendoza, Houston, TX (US); Thomas Andrew Kent, Houston, TX (US); William Dalmeida, Jr., League City, TX (US); Paul J. Derry, Houston, TX (US); Ah-Lim Tsai, Sugarland, TX (US); Muralidhar L. Hegde, Houston, TX (US); Prakash Dharmalingam, Houston, TX (US); Pavana Dixit Hegde, Houston, TX (US); Sankar Mitra, Houston, TX (US); Joy Mitra, Houston, TX (US)

(73) Assignees: William Marsh Rice University, Houston, TX (US); Board of Regents, The University of Texas System, Austin, TX (US); Baylor College of Medicine, Houston, TX (US); Houston Methodist Research Institute, Houston, TX (US); The United States Government, Washington, DC (US)

( * ) Notice: Subject to any disclaimer, the term of this patent is extended or adjusted under 35 U.S.C. 154(b) by 790 days.

(21) Appl. No.: 16/608,713
(22) PCT Filed: Apr. 30, 2018
(86) PCT No.: PCT/US2018/030315
§ 371 (c)(1),
(2) Date: Oct. 25, 2019
(87) PCT Pub. No.: WO2018/201157
PCT Pub. Date: Nov. 1, 2018

(65) Prior Publication Data
US 2020/0222453 A1    Jul. 16, 2020

Related U.S. Application Data

(60) Provisional application No. 62/556,719, filed on Sep. 11, 2017, provisional application No. 62/491,995, filed on Apr. 28, 2017.

(51) Int. Cl.
*A61K 33/36* (2006.01)
*A61K 9/16* (2006.01)
(Continued)

(52) U.S. Cl.
CPC ............ *A61K 33/36* (2013.01); *A61K 9/1641* (2013.01); *A61K 9/51* (2013.01); *A61K 33/0* (Continued)

(58) Field of Classification Search
None
See application file for complete search history.

(56) References Cited

U.S. PATENT DOCUMENTS 8,313,724 B2   11/2012  Hwang et al.
8,784,866 B2    7/2014  Tour et al.
(Continued)

FOREIGN PATENT DOCUMENTS

WO   WO-2013066398 A1 *  5/2013  ......... A61K 47/6925
WO        2014062228 A1     4/2014
(Continued)

OTHER PUBLICATIONS

Almarsson, O., et al., "Mechanism of One-Electron Oxidation of NAD(P)H and Function of NADPH Bound to Catalase", J Am. Chem. Soc. 1993, 115, 7093-7102 ("Almarsson 1993"); 10 pages.
(Continued)

*Primary Examiner* — Kyung S Chang
(74) *Attorney, Agent, or Firm* — Dickinson Wright PLLC; Ross Spencer Garsson

(57) ABSTRACT

Modified hydrophilic carbon clusters (HCCs), poly(ethylene glycol)-hydrophilic carbon clusters (PEG-HCCs) and similarly structured materials like graphene quantum dots
(Continued)

(GQDs), PEGylated GQDs, small molecule antioxidants, and PEGylated small molecule antioxidants. These materials have been modified with an iron chelating moiety, deferoxamine, or a similar chelating moiety. By exploiting common binding sites, the carbon nanostructure facilitates intracellular transport including in mitochondria, reduces oxidative breakdown of the chelator moiety prior to treatment, and reduces both the cause and consequences of metal induced oxidative stress within the body thus providing a novel form of therapy for a range of oxidative and metal-related toxicities. Graphenic materials can be used for the treatment of acute and chronic mitochondrial electron transport chain dysfunction.

4 Claims, 45 Drawing Sheets

(51) Int. Cl.
```
A61K 9/51      (2006.01)
A61K 33/04     (2006.01)
A61K 33/24     (2019.01)
A61K 33/241    (2019.01)
A61K 33/26     (2006.01)
A61K 33/30     (2006.01)
A61K 33/34     (2006.01)
A61P 25/28     (2006.01)
```
(52) U.S. Cl.
CPC .... 4 (2013.01); *A61K 33/24* (2013.01); *A61K 33/241* (2019.01); *A61K 33/26* (2013.01); *A61K 33/30* (2013.01); *A61K 33/34* (2013.01); *A61P 25/28* (2018.01)

(56) References Cited

U.S. PATENT DOCUMENTS

| | | | |
|---|---|---|---|
| 8,916,606 | B2 | 12/2014 | Tour et al. |
| 9,572,834 | B2 | 2/2017 | Tour et al. |
| 2016/0256403 | A1* | 9/2016 | Singh ............... A61K 9/5146 |

FOREIGN PATENT DOCUMENTS

| | | |
|---|---|---|
| WO | 2015034930 A1 | 3/2015 |
| WO | 2018201157 A1 | 11/2018 |

OTHER PUBLICATIONS

"A Re-Assessment of Iron and Reactive Oxygen Species as an Alzheimer's Disease Target: Do Tau Oligomers Change the Playing Field?"; 41 pages.
"DNA damage mediated neuronal and vasculature cell death in mouse/cellular models of hemorrhagic stroke"; 1 page.
Bitner, B., et al., "Antioxidant carbon particles improve cerebrovascular dysfunction following traumatic brain injury", ACS Nano. Sep. 25, 2012; 6(9):8007-14 ("Bitner 2012"); 8 pages.
Candeias, L., et al., "The catalysed NADH reduction of resazurin to resorufin", J. Chem Soc. Perkin Trans. 1998, 2 2333, 2333-2334 ("Candeias 1998"); 2 pages.
Deferoxamine to Prevent Delayed Cerebral Ischemia After Subarachnoid Hemorrhage, ClinicalTrials gov, Aug. 15, 2014 Identifier:NCT02216513 ("Deferoxamine 2014").
Frontera, J., et al., "Acute ischemia after subarachnoid hemorrhage, relationship with early brain injury and impact on outcome: a prospective quantitative MRI study", J Neurol Neurosurg Psychiatry. Jan. 2015; 86(1):71-8. doi: 10.1136/innp-2013-307313 ("Frontera 2015"); 8 pages.
Gerbicki, J., et al., "Transient Species in the Stepwise Interconversion of NADH and NAD+", Acc. Chem. Res. 2004, 37, 379-386 ("Gebicki 2004"); 8 pages.
Grodkowski, J., et al., "One-Electron Transfer Reactions of the Couple NAD/NADH", J Phys. Chem. 1983, 87, 3135-3138 ("Grodkowski 1983"); 4 pages.
Hedge, M., et al., "Specific Inhibition of NEIL-initiated repair of oxidized base damage in human genome by copper and iron: potential etiological linkage to neurodegenerative diseases", J Biol Chem 285, 28812-28825 ("Hegde 2010"); 15 pages.
Hishikawa, T., et al., "Effects of deferoxamine-activated hypoxia-inducible factor-1 on the brainstem after subarachnoid hemorrhage in rats", Neurosurgery. Jan. 2008;62(1):232-40 ("Hishikawa 2008"); 10 pages.
Inoue, T., et al., "Characterization of a Novel MR-detectable nanoantioxidant that Mitigates the Recall Immune Response", NMR in Biomedicine, Aug. 24, 2016, 29: 1436-1444, 9 pages.
Jain, K., "Cerebral vasospasm: treatment", http://www.medmerits.com/index.php/article/cerebral_vasospasm_treatment/P6. Originally released Aug. 11, 1998; last updated Nov. 4, 2020; 2 pages.
Khazalpour, S., et al., "Electrochemical study of Alamar Blue (resazurin) in aqueous solutions and room-temperature ionic liquid I-butyl-3-methylimidazolium tetrafluoroborate at a glassy carbon electrode", RSC Adv. 2004, 4, 8431 ("Khazalpour 2014"); 8 pages.
Lee, J., et al., "Deferoxamine Reduces Early Brain Injury Following Subarachnoid Hemorrhage", Trends in Neurovascular Surgery. vol. 112 of the series Acta Neurochirurgica Supplementum pp. 101-106 ("Lee 2011"); 6 pages.
Lee, J., et al., "Hemoglobin and iron handling in brain after subarachnoid hemorrhage and the effect of deferoxamine on early brain injury", J Cereb Blood Flow Metab. Nov. 2010; 30(11):1793-803 ("Lee 2010"); 11 pages.
Mitra, J., et al., "Revisiting Metal Toxicity in Neurodegenerative Diseases and Stroke: Therapeutic Potential", Neurol Res Ther 1(2). pii:107 ("Mitra 2014"); 9 pages.
Mori, T., et al., "Intracisternal increase of superoxide anion production in a canine subarachnoid hemorrhage model", Stroke. Mar. 2001; 32(3):636-42 ("Mori 2001"); 7 pages.
Nilewski, L., et al., "Carbon nanoparticles and oxidative stress: could an injection stop brain damage in minutes?", Nanomedicine (Lond). 2015;10(11):1677-9 ("Nilewski 2015"); 3 pages.
Samuel, E., et al., "Highly efficient conversion of superoxide to oxygen using hydrophilic carbon clusters", Proc Natl Acad Sci U S A. Feb. 24, 2015;112(8):2343-8 ("Samuel 2015"); 6 pages.
Samuel, E., et al., "Hydrophilic carbon clusters as therapeutic, high-capacity antioxidants", Trends Biotechnol. Oct. 2014;32(10):501-5 ("Samuel 2014"); 5 pages.
Wang, H., et al., "Chronic oxidative damage together with genome repair deficiency in the neurons is a double whammy for neurodegeneration: Is damage response signaling a potential therapeutic target?", Mech Ageing Dev. Sep. 20.pii:S0047-6347. .Epub ahead of print ("Wang 2016"); 14 pages.
International Bureau, International Preliminary Report on Patentability for PCT/US2018/030315 mailed on Nov. 7, 2019, 7 pages.
International Searching Authority, International Search Report and Written Opinion for PCT/US2018/03015 mailed on Aug. 1, 2018, 12 pages.

\* cited by examiner

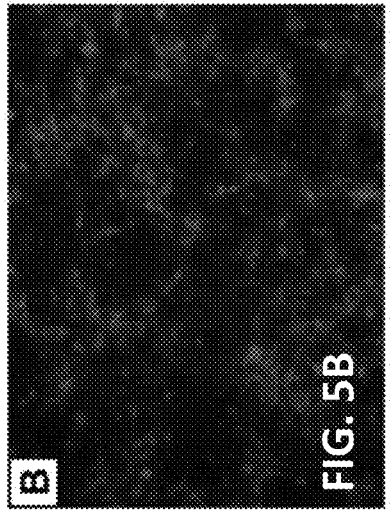
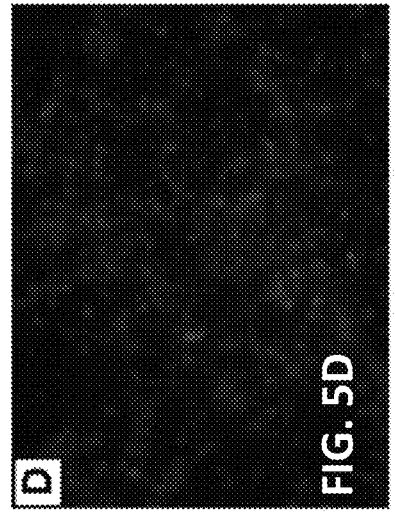
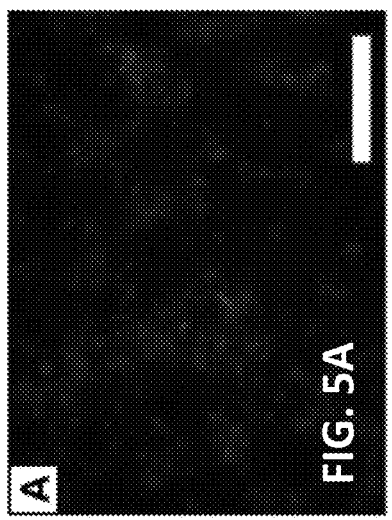
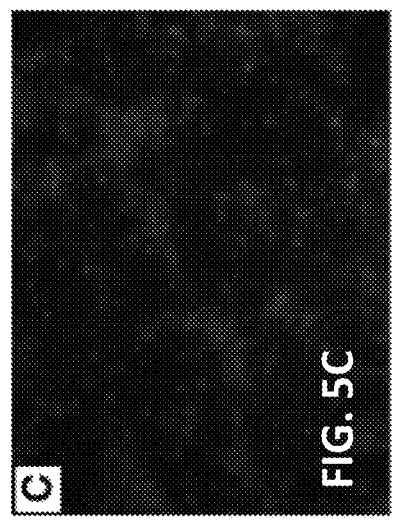

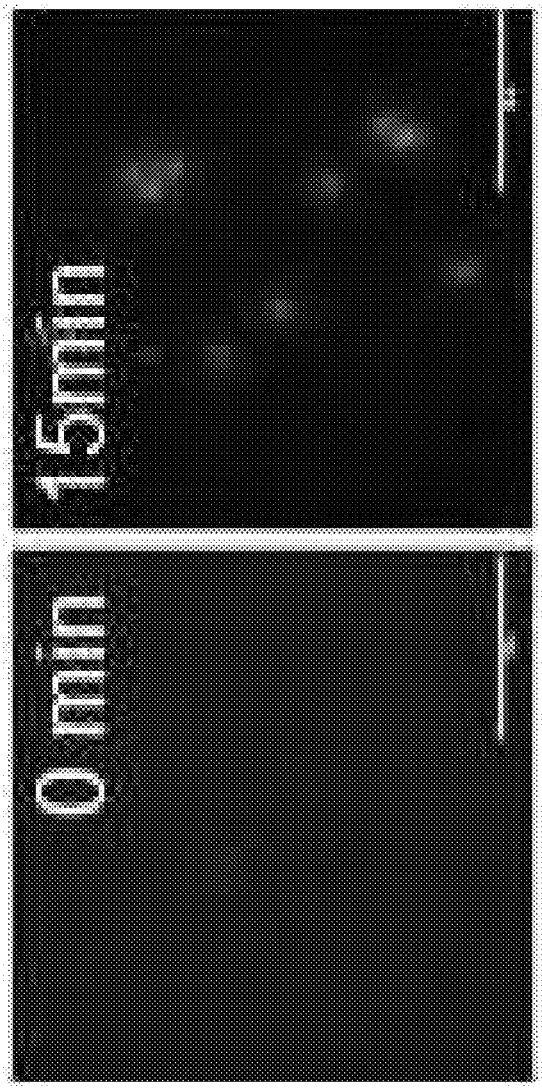

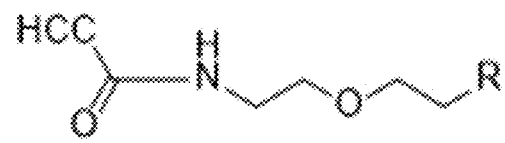
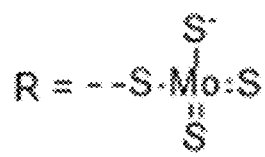
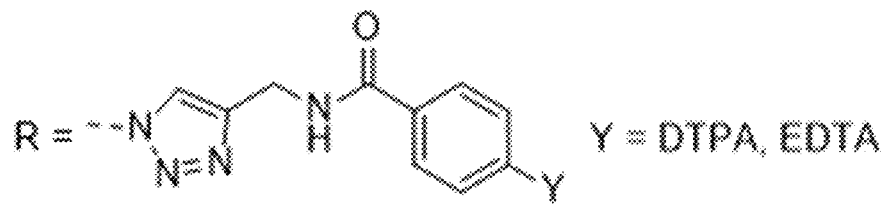
Y = DTPA, EDTA
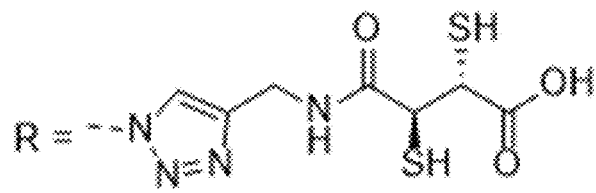
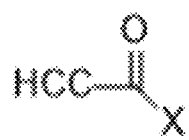
X = DEF, Pencillamine
FIG. 21

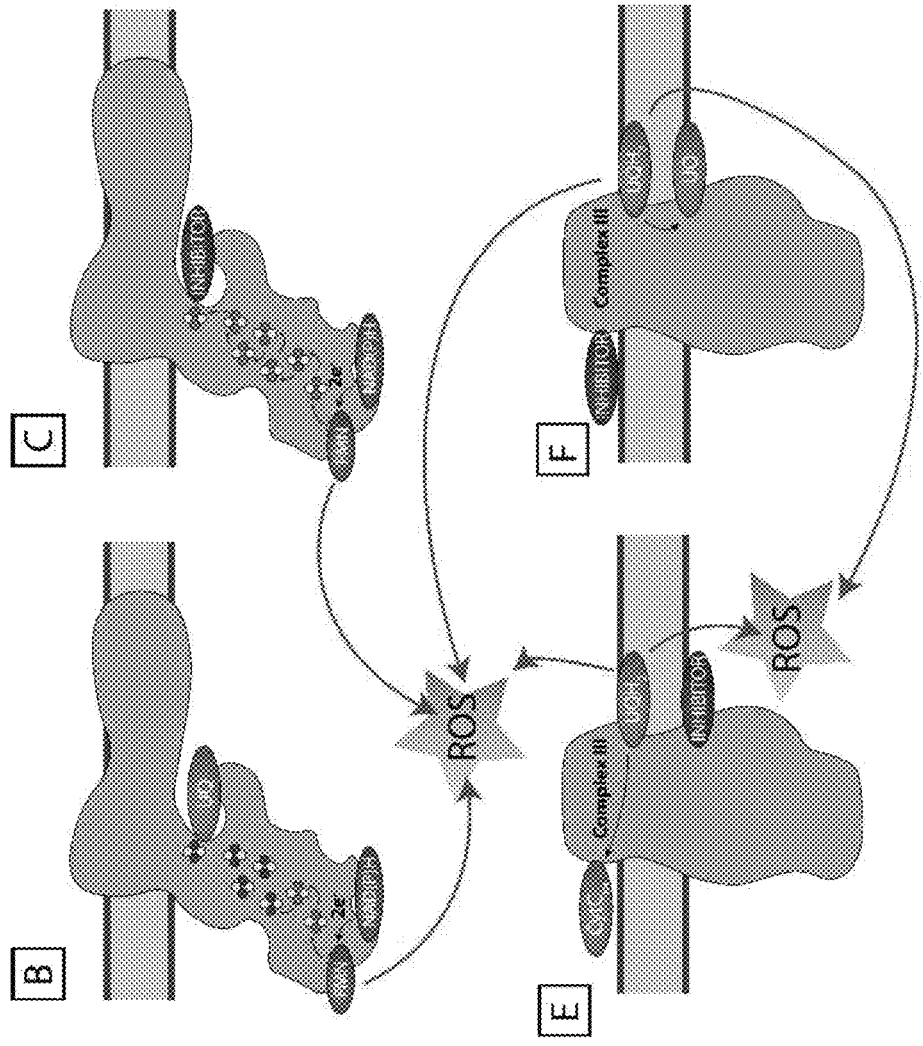

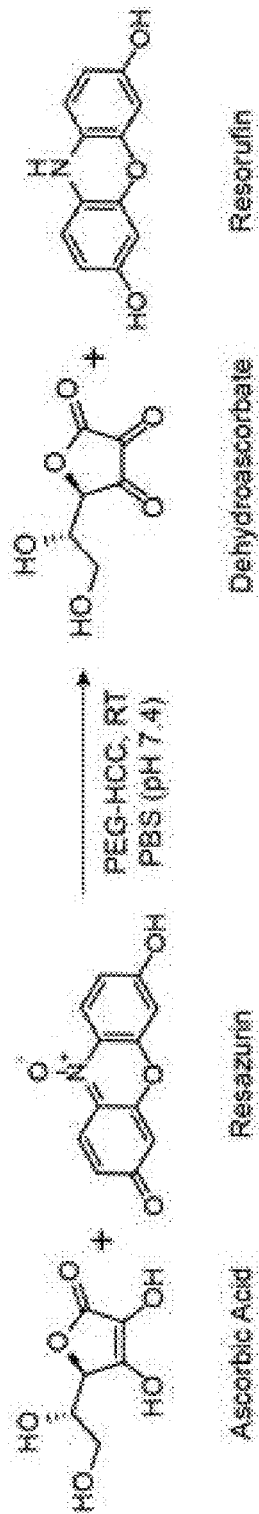
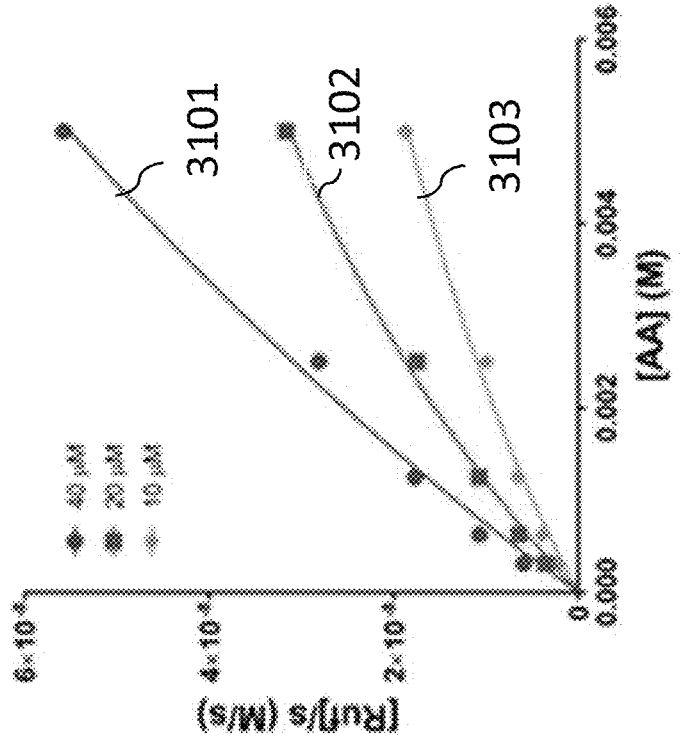
FIG. 31A
FIG. 31B

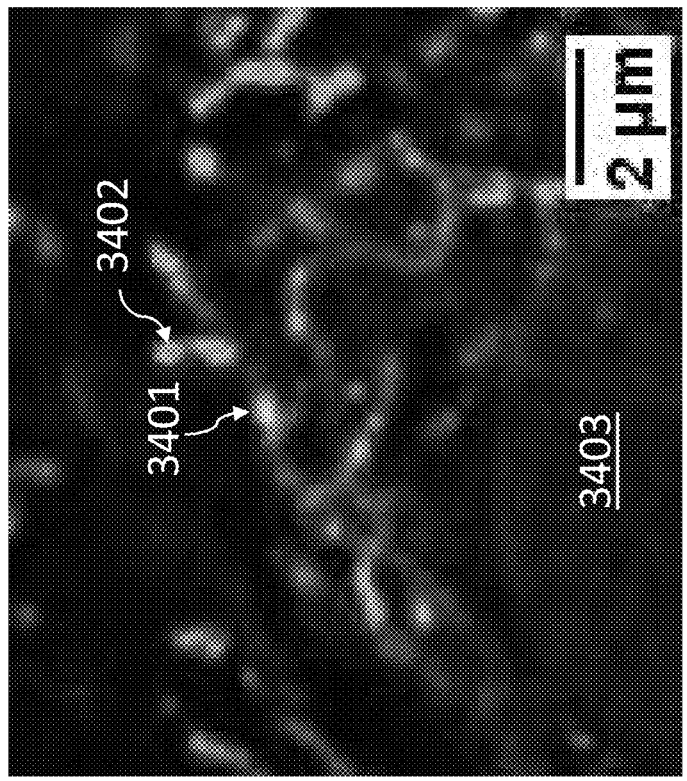
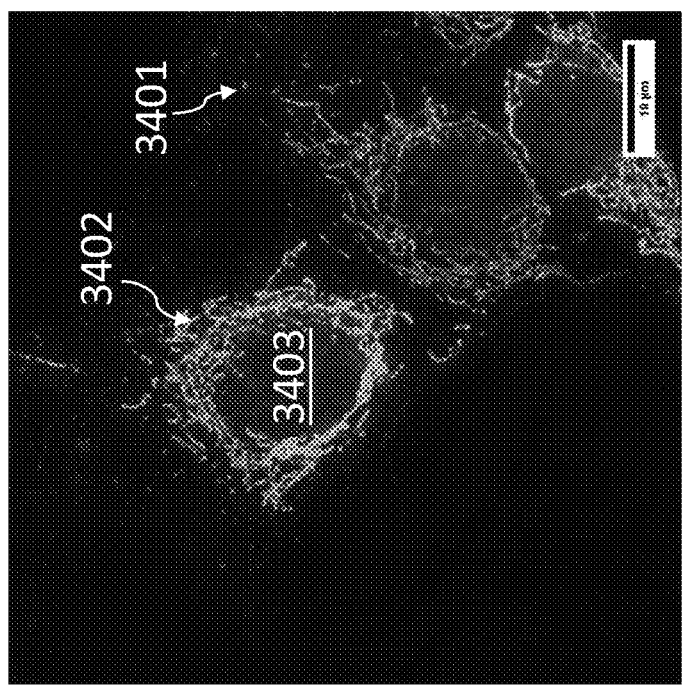
FIG. 34B
FIG. 34A

ACUTE AND CHRONIC MITOCHONDRIAL ELECTRON TRANSPORT CHAIN DYSFUNCTION TREATMENTS AND GRAPHENIC MATERIALS FOR USE THEREOF

RELATED PATENTS/PATENT APPLICATIONS

The application is a 35 U.S.C § 371 national application of International PCT Application Publ. No. WO/2018/201157, filed Apr. 30, 2018, published Nov. 1, 2018, and entitled "Acute And Chronic Mitochondrial Electron Transport Chain Dysfunction Treatments And Graphenic Materials For Use Thereof." which designated the United States, and which claims priority to provisional patent application: (a) U.S. Patent Application No. 62/491,995, entitled "Antioxidant Nanoparticles Having Attached Chelating Moieties And Methods Of Making And Using Same," filed on Apr. 28, 2017, and (b) U.S. Patent Application No. 62/556,719, entitled "Graphenic Materials For The Treatment Of Acute And Chronic Mitochondrial Electron Transport Chain Dysfunction," filed on Sep. 11, 2017, which applications are commonly assigned to the Applicants of the present invention and are hereby incorporated herein by reference in their entirety for all purposes.

GOVERNMENT INTEREST

This invention was made with government support under Grant Nos. NS094535, NS084290, and NS088645 award by the National Institutes of Health. The government has certain rights in the invention.

TECHNICAL FIELD

The present invention relates in general to acute and chronic mitochondrial electron transport chain dysfunction treatments and graphenic materials, such as modified antioxidant nanoparticles for use thereof, including, antioxidant nanoparticles having attached chelating moieties for synergistic activity.

BACKGROUND OF INVENTION

Traumatic brain injury (TBI) is a leading cause of death and disability in the United States. Annually, an estimated 1.7 million individuals sustain TBI, resulting in 52,000 deaths and 275,000 hospitalizations. TBI is classified into mild, moderate and severe injury, with approximately 75% of TBI injuries each year designated as concussions or forms of mild traumatic brain injury (MTBI). Hypotension, often due to hemorrhage from concomitant injury, worsens all severity levels of TBI. Oxidative stress is a prominent feature of TBI, especially when complicated by secondary trauma such as hemorrhagic hypotension.

Based on many lines of evidence, oxidative stress is a major pathophysiological factor in ischemia and reperfusion injury. This evidence is exemplified by robust neuroprotection in multiple transgenic antioxidant overexpression models of ischemia/reperfusion. However, no clinical trial of antioxidant therapy in any form of brain injury has shown benefit. It is believed this failure is due to two major factors: (1) There are severe limitations in currently available antioxidants that hinder their effectiveness when employed following ischemia as opposed to pretreatment and (2) oxidative stress injury is quantitatively more important under specific clinical circumstances, so a benefit might be missed if it is not tested under the most relevant conditions. In stroke, those conditions are typically those that have the worst outcomes such as hyperglycemia at the time of stroke when treated with recanalization therapy (6). More specifically, animal models were often tested with the antioxidant immediacy following the TBI. While in clinical scenarios, there is often a delay between the time of the injury and the time of definitive care. Therefore, more accurate animal models should delay the treatment regime by a period of 60 to 90 minutes to simulate the typical time from an injury to the time that a patient can be treated in an emergency facility.

Several defense mechanisms exist to cope with oxidative radicals generated during normal physiology. These mechanisms consist of enzymes and other proteins that modify the radical species in a series of steps ultimately leading to water. For example, the fate of superoxide radical ($O_2^{\cdot-}$ or abbreviated SO) when dismutation catalyzed by superoxide dismutase (SOD) is to react with 2 molecules of SO to form one molecule of $O_2$ and one molecule of hydrogen peroxide, $H_2O_2$. As the $H_2O_2$ encounters free iron, the iron catalyzes the Fenton reaction where $H_2O_2$ generates hydroxyl radical, HO. Under normal conditions, there are sufficient levels of protective proteins for detoxification to remove this excess free iron, thereby inhibiting the formation of the very reactive hydroxyl radical. Under pathological circumstances, however, these protective factors are depleted. After acute injury, they cannot upregulate fast enough. As a result, unstable intermediates are formed that become part of a radical cascade leading to damage and disruption of a wide variety of vital functions.

Given these considerations, once a radical cascade begins, the limitations of many current antioxidants can be summarized as including the following:

(A) Mechanism of Action: Many antioxidants "transfer" the radical to another unstable species. SOD generates $H_2O_2$ that can subsequently generate ·OH. Under normal circumstances, catalase, and glutathione are present in sufficient quantities to quench the resultant radicals. This may not be the case under pathological conditions; SOD may actually generate more damaging species.

(B) Need for Regeneration: Many antioxidants, such as vitamin E and vitamin C, require regeneration and require factors (glutathione) that are themselves consumed in the oxidative milieu.

(C) Limited Capacity: Most current antioxidants have limited capacity and are unlikely to be able to cope with a burst of radicals and their subsequent unstable products if administered after the burst is initiated. High dose albumin, recently failing to show benefit as an antioxidant in stroke, has a restricted number of thiol moieties that quench radicals.

(D) Selectivity: High selectivity is a disadvantage if the agent's mechanism involves radical transfer and depends on downstream enzymes to cope with newly formed radicals.

Nearly, every currently antioxidant shares one or more of these limitations. Accordingly, needs remain for improved antioxidants.

SUMMARY OF THE INVENTION

The present invention involves modified hydrophilic carbon clusters (HCCs), poly(ethylene glycol)-hydrophilic carbon clusters (PEG-HCCs) and similarly structured materials like graphene quantum dots (GQDs), PEGylated GQDs (PEG-GQDs), small molecule antioxidants, and PEGylated small molecule antioxidants. Specifically, these materials have been modified with an iron chelating moiety, deferoxamine, or a similar chelating moiety. By exploiting common binding sites, the carbon nanostructure facilitates intracellular transport including in mitochondria, reduces oxidative breakdown of the chelator moiety prior to treatment, and reduces both the cause and consequences of metal induced oxidative stress within the body thus providing a novel form of therapy for a range of oxidative and metal-related toxicities.

The present invention further relates to a newly discovered function of graphenic materials to serve a new use as an electron transport chain "bypass" mechanism in cases of mitochondrial injury to capture electrons from superoxide and reduce oxidized species in the electron transport chain while not directly replacing, or substituting the existing electron transport chain members. This is a new use for materials that Applicants have previously shown to function as high capacity antioxidants and extends the potential use of these agents to conditions involving mitochondrial injury. A new mechanism to shuttle electrons between key surrogates and proteins of the mitochondrial electron transport chain has been discovered. This new mechanism of electron transport shuttle (ETS) is termed the Kent Electron Transport Shuttle (KETS).

In general, in one embodiment, the invention features a therapeutic composition that includes an antioxidant nanoparticle covalently modified with a chelating moiety. The antioxidant nanoparticle has both antioxidant and pro-oxidant properties. The therapeutic composition is operable to act as a high capacity oxidant and directly transports electrons and reduces key mitochondrial enzymes when administered to a subject. The therapeutic composition has a chelation efficacy that is at least ten times greater as compared to a same amount of the chelating moiety without the antioxidant nanoparticle.

Implementations of the invention can include one or more of the following features:

The therapeutic composition can have a chelation efficacy that is at least 100 times greater as compared to a same amount of the chelating moiety without the antioxidant nanoparticle.

The chelating moiety can be a metal-chelating moiety.

The metal-chelating moiety can be a chelator of a metal selected from a group consisting of aluminum, americium, arsenic, cadmium, cesium, chromium, copper, curium, iron, lead, mercury, plutonium, thallium, uranium, or zinc.

The metal can be selected from a group consisting of arsenic, cadmium, copper, iron, lead, selenium, zinc, and combinations thereof.

The chelating moiety can be DEF.

The antioxidant nanoparticle can be selected from a group consisting of PEG-HCC, PEG-GQD, and PEG-PDI.

The therapeutic composition can be DEF-PEG-HCC.

The therapeutic composition can be DEF-PEG-GQD.

The ratio of PEG to chelating moiety can be between 1:3 and 3:1.

The ratio of PEG to chelating moiety can be less than 1:1.

The therapeutic composition can be operable to treat, reduce, or prevent mitochondrial injury.

The chelating moiety can be selected from a group consisting of DEF, DTPA, dimercaprol, succimer, unithiol, Prussian blue, D-penicillamine, trientine, deferasirox, deferiprone, calcium disodium edetate (EDTA), hydroxypyridonates, tetrathiomolybdate, pentetic acid, or trientine.

In general, in another embodiment, the invention features a method that includes selecting one of the above-described therapeutic compositions. The method further includes administering the therapeutic composition to a subject. The amount of chelator moiety in the therapeutic composition administered is reduced to at most 10% of the amount of chelator moiety needed to be administered to obtain the same amount of chelation efficacy of the chelator moiety without the antioxidant nanoparticle. The therapeutic compositions acts as a high capacity oxidant and directly transports electrons and reduces key mitochondrial enzymes when administered to the subject.

Implementations of the invention can include one or more of the following features:

The amount of chelator moiety in the therapeutic composition administered can be reduced to at most 1% of the amount of chelator moiety needed to be administered to obtain the same amount of chelation efficacy of the chelator moiety without the antioxidant nanoparticle The method step of administering the therapeutic composition can be to treat, reduce, or prevent mitochondrial injury.

The step of administering the therapeutic composition to the subject can reduce the metal induced oxidative stress in the subject.

The step of administering the therapeutic composition to the subject can treat tissue injury of the subject.

The tissue injury can be brain injury.

The brain injury can be intracerebral hemorrhage.

The tissue injury can be of a tissue that is part of the central nervous system.

The step of administering the therapeutic composition to the subject can inhibit ferroptosis.

The step of administering the therapeutic composition to the subject can treat metal toxicity in the subject.

The metal toxicity in the subject can include a metal selected from a group consisting of aluminum, americium, arsenic, cadmium, cesium, copper, chromium, copper, curium, iron, lead, mercury, plutonium, thallium, uranium, and zinc.

The step of administering the therapeutic composition to the subject can improve oxygenated ($O_2$) blood flow in the subject.

The step of administering the therapeutic composition to the subject can treat, reduce, or prevent ischemia and reperfusion injury of the subject.

In general, in another embodiment, the invention features a method of making a therapeutic composition. The method includes the step of selecting an antioxidant nanoparticle. The antioxidant nanoparticle has both antioxidant and pro-oxidant properties. The method further includes the step of covalently modifying the antioxidant nanoparticle with a chelating moiety. The therapeutic composition is operable to act as a high capacity oxidant and directly transports electrons and reduces key mitochondrial enzymes when administered to a subject. The therapeutic composition has a chelation efficacy that is at least ten times greater as compared to a same amount of the chelating moiety without the antioxidant nanoparticle.

Implementations of the invention can include one or more of the following features:

The therapeutic composition can have a chelation efficacy that is at least 100 times greater as compared to a same amount of the chelating moiety without the antioxidant nanoparticle.

The chelating moiety can be a metal-chelating moiety.

The metal-chelating moiety can be a chelator of a metal san aluminum, americium, arsenic, cadmium, cesium, chromium, copper, curium, iron, lead, mercury, plutonium, thallium, uranium, or zinc-chelating moiety.

The metal can be selected from a group consisting of arsenic, cadmium, copper, iron, lead, selenium, zinc, and combinations thereof.

The chelating moiety can be DEF.

The antioxidant nanoparticle can be selected from a group consisting of PEG-HCC, PEG-GQD, and PEG-PDI.

The therapeutic composition can be DEF-PEG-HCC.

The therapeutic composition can be DEF-PEG-GQD.

The ratio of PEG to chelating moiety can be between 1:3 and 3:1.

The ratio of PEG to chelating moiety can be less than 1:1.

The therapeutic composition can be operable to treat, reduce, or prevent mitochondrial injury.

The chelating moiety can be selected from a group consisting of DEF, DTPA, dimercaprol, succimer, unithiol, Prussian blue, D-penicillamine, trientine, deferasirox, deferiprone, calcium disodium edetate (EDTA), hydroxypyridonates, tetrathiomolybdate, pentetic acid, or trientine.

In general, in another embodiment, the invention features a therapeutic composition that includes an antioxidant nanoparticle covalently modified with a chelating moiety. The antioxidant nanoparticle has both antioxidant and pro-oxidant properties. The chelating moiety is an iron-chelating moiety. The therapeutic composition is operable to act as a high capacity oxidant and directly transports electrons and reduces key mitochondrial enzymes when administered to a subject.

Implementations of the invention can include one or more of the following features:

The iron-chelating moiety can be DEF.

The antioxidant nanoparticle can be selected from a group consisting of PEG-HCC, PEG-GQD, and PEG-PDI.

In general, in another embodiment, the invention features a method that includes selecting one of the above-described therapeutic compositions. The method further includes administering the therapeutic composition to a subject. The therapeutic compositions acts as a high capacity oxidant and directly transports electrons and reduces key mitochondrial enzymes when administered to the subject.

In general, in another embodiment, the invention features a method of making a therapeutic composition. The method includes the step of selecting an antioxidant nanoparticle. The antioxidant nanoparticle has both antioxidant and pro-oxidant properties. The method further includes the step of covalently modifying the antioxidant nanoparticle with a chelating moiety. The chelating moiety is an iron-chelating moiety. The therapeutic composition is operable to act as a high capacity oxidant and directly transports electrons and reduces key mitochondrial enzymes when administered to a subject.

Implementations of the invention can include one or more of the following features:

The iron-chelating moiety can be DEF.

The antioxidant nanoparticle can be selected from a group consisting of PEG-HCC, PEG-GQD, and PEG-PDI.

In general, in another embodiment, the invention features a therapeutic composition that includes an antioxidant nanoparticle covalently modified with a chelating moiety. The antioxidant nanoparticle has both antioxidant and pro-oxidant properties. The chelating moiety has a first portion that is not an active site for chelation by the chelating moiety. The chelating moiety is covalently bound to the antioxidant nanoparticle at the first portion. The therapeutic composition is operable to act as a high capacity oxidant and directly transports electrons and reduces key mitochondrial enzymes when administered to a subject.

Implementations of the invention can include one or more of the following features:

The antioxidant nanoparticle can be selected from a group consisting of PEG-HCC, PEG-GQD, and PEG-PDI.

In general, in another embodiment, the invention features a method that includes selecting one of the above-described therapeutic compositions. The method further includes administering the therapeutic composition to a subject. The therapeutic compositions acts as a high capacity oxidant and directly transports electrons and reduces key mitochondrial enzymes when administered to the subject.

In general, in another embodiment, the invention features a method of making a therapeutic composition. The method includes the step of selecting an antioxidant nanoparticle. The antioxidant nanoparticle has both antioxidant and pro-oxidant properties. The method includes the step of covalently modifying the antioxidant nanoparticle with a chelating moiety. The chelating moiety has a first portion that is not an active site for chelation by the chelating moiety. The chelating moiety is covalently bound to the antioxidant nanoparticle at the first portion. The therapeutic composition is operable to act as a high capacity oxidant and directly transports electrons and reduces key mitochondrial enzymes when administered to a subject.

Implementations of the invention can include one or more of the following features:

The antioxidant nanoparticle can be selected from a group consisting of PEG-HCC, PEG-GQD, and PEG-PDI.

In general, in another embodiment, the invention features a method of treating disorders of electron transport in a subject. The method includes identifying a subject who needs to be treated for a disorder of electron transport. The disorder of electron transport includes electronic leakage from mitochondrial complexes in the electron transport chain. The method further includes administering a therapeutic composition to the subject. The therapeutic composition comprises a carbon material that has antioxidant and pro-oxidant properties. The method further includes utilizing the therapeutic composition to terminate the free radical on reactive oxygen species (ROS) in the subject. The method further includes utilizing the therapeutic composition to transport electrons in the mitochondrial membrane of cells in the subject.

Implementations of the invention can include one or more of the following features:

The method can further include utilizing the therapeutic composition to directly address electron leakage from the mitochondrial complexes in the electron transport chain by quenching reactive oxygen species (ROS) that had been generated or reactive nitrogen species (RNS) that had been generated.

The reactive oxygen species (ROS) can include a superoxide.

The reactive oxygen species (ROS) can be a hydroxyl radical.

The method can further include utilizing the therapeutic composition to terminate free radicals on reactive nitrogen species.

The method can further include utilizing the therapeutic composition to provide electron shuttle and transport restoration.

The step of utilizing the therapeutic composition to provide electron shuttle and transport restoration can include protecting against dysfunction of the endogenous electron shuttle capability of the subject.

Damage to critical cellular systems can be treated by reducing the electron leakage that result in loss of proton gradient, increased levels of reactive oxygen species, and cellular injury in the subject.

The electron leakage can occur from injury to electron transport proteins and their intermediates.

The electron proteins and their intermediates can be selected from a group consisting of NADPH, Flavin, cytochrome c, mitochondrial, organelle enzymes and combinations thereof.

The electron shuttle and transport restorative ability can take place in the mitochondria membrane of a cell, organelles, or a combination thereof.

The method can further include utilizing the therapeutic composition to transport electrons in the mitochondrial membrane of a cell.

The subject can be a mammal.

The mammal can be a human.

The administering of the therapeutic composition can include administration through intravenous, subcutaneous, intramuscular, oral, dermal or nasal routes.

The method disorder of electron transport can be associated with a condition selected from a group consisting of hereditary and acquired mitochondrial injuries; acute injuries to the nervous system; peripheral injuries; systemic injuries; neurodegenerative disorders; systemic organ disorders; disorders of inflammation; organ transplantations, organ transplantations coupled with blood reperfusion, trauma, trauma coupled with hemorrhagic shock and blood reperfusion, stroke, stroke coupled with blood-flow restoration to the brain, and combinations thereof.

The hereditary and acquired mitochondrial injuries can be selected from a group consisting of mitochondrial genetic mutation disorders, Wilson's Disease, genetic disorders of metal metabolism, acute and chronic poisoning with mitochondrial toxins exemplified by cyanide or arsenic, and combinations thereof. The acute injuries to the nervous system can be selected from a group consisting of traumatic brain injuries, ischemia, hemorrhage, anoxic encephalopathy, hypoxic or ischemic encephalopathy, reperfusion, blood reperfusion, stroke, cerebrovascular dysfunction, spinal cord injuries, central nervous system injuries, and combinations thereof. The peripheral injuries can be selected from a group consisting of neuropathy. The systemic injuries can be selected from a group consisting of hemorrhagic shock, hypoxia, hypotension, myocardial infarction and injuries, pulmonary injuries, and combinations thereof. The neurodegenerative disorders can be selected from a group consisting of Alzheimer's disease, Parkinson's disease, amyotrophic lateral sclerosis, autism, Wilson's Disease and combinations thereof. The systemic organ disorders can be selected from a group consisting of liver disease, non-alcoholic fatty liver disease, diabetes, myocardial infarction and injury, pulmonary injuries, and combinations thereof. The disorders of inflammation can be selected from a group consisting of inflammatory bowel disease.

The disorder of electron transport can be associated with cerebrovascular dysfunction following traumatic brain injury.

The carbon material can be selected from a group consisting of single-walled nanotubes, double-walled nanotubes, triple-walled nanotubes, multi-walled nanotubes, ultra-short nanotubes, graphene, graphene nanoribbons, graphite, graphene oxide, graphene oxide nanoribbons, carbon black, oxidized carbon black, hydrophilic carbon clusters, graphene quantum dots, carbon dots, coal, coke, and combinations thereof.

The carbon material can be doped with heteroatoms.

The heteroatoms can be selected from a group consisting of O, N, S, P, B, and combinations thereof.

The carbon material can be functionalized with a plurality of solubilizing groups.

The solubilizing groups can be selected from a group consisting of poly(ethylene glycol), poly(propylene glycol), poly(vinyl alcohol), poly(p-phenylene oxide), poly(ethylene imines), poly(vinyl alcohol), poly(acrylic acid), poly(vinyl amine), vinyl polymers, chain-growth polymers, step-growth polymers, condensation polymers, ring-opening polymers, ring-opening metathesis polymers, living polymers, and combinations thereof.

The carbon material can be functionalized perylene diimide or small molecules with polycyclic aromatic cores that are functionalized.

The small molecule can have moieties of hydroxyl, carboxyl, quinone, epoxy, amino, trifluoromethyl, sulfone, hydrazine, imine, hydroxyimine, groups or combinations thereof.

The therapeutic composition can further include a targeting agent.

The targeting agent can be a targeting agent for organelle, organ or cell type.

The targeting agent can be a protein that targets a cell surface moiety that is up-regulated in response to oxidative stress.

The targeting agent can be a protein selected from a group consisting of p-selectin, transferrin receptors, angiotensin receptors, cannabinoid receptors, epidermal growth factor receptors, adhesion molecules, channel proteins, and combinations thereof.

The targeting agent can be selected from a group consisting of antibodies, proteins, RNA, DNA, aptamers, small molecules, dendrimers, carbohydrates and combinations thereof.

The targeting agent can be a chelator.

The chelator can be selected from a group consisting of DEF, DTPA, dimercaprol, succimer, unithiol, Prussian blue, D-penicillamine, trientine, deferasirox, deferiprone, calcium disodium edetate (EDTA), hydroxypyridonates, tetrathiomolybdate, pentetic acid, or trientine.

The targeting agent can be covalently associated with the carbon material.

The carbon material can be associated with a transporter moiety. The transporter moiety can facilitate the transport of the carbon material through a barrier.

The barrier can be selected from a group consisting of the blood brain barrier, the blood spinal cord barrier, and combinations thereof.

The transporter moiety can be selected from a group consisting of adamantane molecules, adamantine molecule derivatives, cannabinoid molecules, cannabinoid molecule derivatives, HU-210 and combinations thereof.

The transporter moiety can be selected from a group consisting of unnatural enantiomers.

The carbon material can have electron shuttle and transport restorative ability combined with antioxidant activity.

The antioxidant activity can be active toward reactive oxygen species or reactive nitrogen species or combinations thereof.

The reactive oxygen species can include a superoxide or hydroxyl radical or combinations thereof.

The antioxidant can be not reactive toward nitric oxide.

The foregoing has outlined rather broadly the features and technical advantages of the invention in order that the detailed description of the invention that follows may be better understood. Additional features and advantages of the invention will be described hereinafter that form the subject of the claims of the invention. It should be appreciated by those skilled in the art that the conception and the specific embodiments disclosed may be readily utilized as a basis for modifying or designing other structures for carrying out the same purposes of the invention. It should also be realized by those skilled in the art that such equivalent constructions do not depart from the spirit and scope of the invention as set forth in the appended claims.

It is also to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of the description and should not be regarded as limiting.

BRIEF DESCRIPTION OF THE DRAWINGS

The foregoing and other objects, features, and advantages of the present invention will be apparent from the following description of embodiments as illustrated in the accompanying drawings, in which reference characters refer to the same parts throughout the various views. The drawings are not necessarily to scale, emphasis instead being placed upon illustrating principles of the present invention:

FIGS. 5A-5D show that hydrophilic carbon clusters, conjugated to PEG-HCCs reduce the oxidation of CellROX fluorescent dye by hydrogen peroxide in primary murine cortical neurons.

FIGS. 6A-6E illustrates additional in-vitro and in-vivo data related to the mechanism of action involved improvement of the DNA damage response to iron and reactive oxygen toxicity. FIG. 6A-6B show mitochondria specific $H_2O_2$ sensor pHyper fluorescence within 15 min of iron exposure in neurons (FIG. 6A at 0 minutes and FIG. 6B at 15 minutes). FIGS. 6A-6B illustrate the rapid effect of addition iron to cultured neurons in elaboration of reactive oxygen species in the mitochondria. FIG. 6C illustrates that DNA is damaged (lane 2) in both mitochondria and nucleus by the hemoglobin breakdown product hemin. FIG. 6D demonstrates that following experimental intracerebral hemorrhage (ICH) in mice, there is evidence of DNA damage in the peri-hemorrhage region of the brain. FIG. 6E indicates the DEF-PEG-HCC reduces this DNA damage when treated following the ICH better than PEG-HCC or deferoxamine individually.

FIG. 14A is PBS control demonstrating entire middle cerebral artery (MCA) territory infarction. FIG. 14B is following treatment with PEG-HCCs and demonstrated considerable cortical sparing. Tissue section groups came from individual rats. Scale bars are 1 cm.

FIG. 21 illustrates examples of structures of representative chelators and their linkage mechanism bound to the described nanomaterials.

FIGS. 22A-22F illustrate sources of electron leakage in Complex I and III.

FIG. 23A: This illustrates the KETS mechanism. FIG. 23B: Structures and reduction reactions of resazurin and resorufin, the species utilized in model experiments. FIG. 23C: Mechanism of action for flavin mononucleotide (riboflavin, FMN) mediated reduction of resazurin via PEG-HCCs.

FIG. 31A is a scheme showing the substrates and products of PEG-HCC catalyzed reduction of resazurin by PEG-HCCs.

FIG. 31B is a graph showing the saturation kinetics of PEG-HCCs with respect to resazurin and NADH.

FIG. 34A shows a deconvolution microscopy Z-projection of SHSY-5Y cells expressing a photoactivable GFP with a mitochondria targeting sequence from subunit VIII of human cytochrome c. DEF-PEG-HCCs are shown as an AlexaFluor-647 labeled secondary antibody against a mouse anti-PEG primary antibody. Fluorescence signal from the mitochondria and the nucleus are also shown.

FIG. 34B shows a focal plane within the micrograph of FIG. 32A that shows DEF-PEG-HCCs are internalized by SHSY-5Y cells.

DETAILED DESCRIPTION OF THE INVENTION

Figure 1:
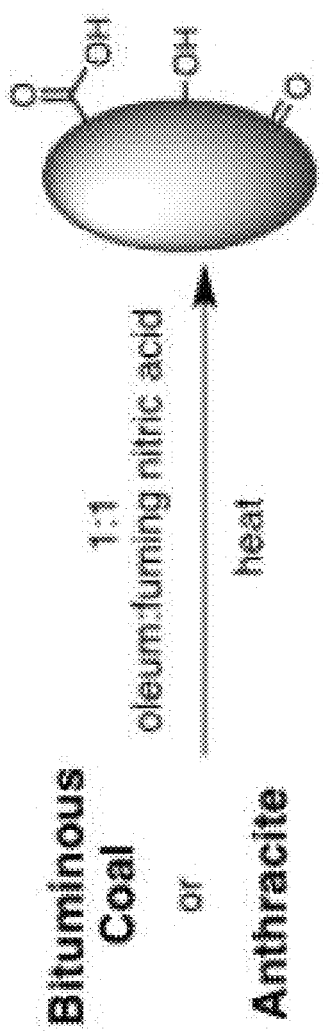
FIG. 1 shows a synthesis of graphene quantum dots (GQDs) from either anthracite or bituminous coal using a 1:1 mixture of fuming sulfuric and fuming nitric acid.

The present invention is a novel therapy for treating tissue injury, and in particular brain injury, such as after hemorrhage in which free iron is released from degraded hemoglobin. One example of this is intracerebral hemorrhage (ICH) in which iron as well as oxidative degradation products of hemoglobin induce cellular toxicity such as to the DNA damage and repair (DDR) responses, cellular death and dysfunction. Iron catalyzes many deleterious processes and in particular oxidative stress due to formation of hydroxyl radical. Iron and other heavy metals also involves many forms of injury including neurodegeneration such as due to accumulation of Alzheimer's Disease toxic proteins that also involve excess binding of iron and other metals. However, these findings have not yet led to an effective treatment to improve functional outcome.

A consequence of this oxidative stress is the occurrence of both oxidative DNA damage and inhibition of DNA repair, both of which have important detrimental effects for genetic integrity. With respect to treating ICH, the repair of DNA damage to neurons due to blood breakdown-related reactive oxygen species (ROS) is inhibited by a low concentration of iron that is expected to be present following ICH. Based on the present invention, it has been discovered that there is a complex yet measurable cross-talk among heme/iron toxicity, ROS and accumulation of genome damage, together with defective DNA damage responses (DDR) in neurons and endothelial cells (vasculature). These factors share a common etiology that may be amenable to therapeutic intervention. This provides a new pharmacological approach to inhibit ROS and restore DDR with a new carbon particle drug combining extraordinary ROS quenching capacity with chelation to address these contributors to poor outcome.

A new mechanism, the KETS mechanism, to shuttle electrons between key surrogates and proteins of the mitochondrial electron transport chain has been discovered. The reduction potential of antioxidants (like PEG-HCCs) is like that of ubiquinone and enables them to shuttle electrons from low reduction potential species such as NADH and NADPH to higher reduction electron transport chain constituents. PEG-HCCs demonstrated an acceleration of the reduction of resazurin (a test indicator of mitochondrial viability) and cytochrome c by NADH and ascorbic acid in solution. Kinetics indicated PEG-HCCs catalyze the oxidation of NADH and ascorbate, and the reduction of resazurin and cytochrome C through a transient tertiary complex as opposed to a ping-pong-like mechanism. Deconvolution fluorescent microscopy identified PEG-HCCs in close proximity to mitochondria after brief incubation with cultured endothelial and neuronal cells. In cell culture, PEG-HCCs were able to protect against hydrogen peroxide and the mitochondrial poison, sodium cyanide. Compared to methylene blue, the prototypical small molecule electron transport shuttle (ETS), PEG-HCCs showed a 10-fold lower $K_m$ at the same mass concentration, revealing that they would not interfere with normal mitochondrial function and demonstrated better protection without the toxicity observed between hydrogen peroxide and MB. This newly described KETS mechanism contributes to the already powerful antioxidant properties and provides for their remarkable in-vivo efficacy in a range of models of oxidative stress. The KETS mechanism can be used to extend the potential use antioxidants materials (such as PEG-HCC, PEG-GQD, etc.) to a range of mitochondrial disorders. I.e., antioxidant materials can be utilized in biochemically relevant pathways specifically as an electron transport shuttle (ETS) in conditions relevant to disruption of mitochondrial oxidative phosphorylation.

Electron shuttles are crucial in cellular respiration. Because components of the electron transport chain are spatially separated in the inner membrane of mitochondria, small carrier molecules are needed to facilitate the transfer of electrons. For instance, ubiquinone has a reduction potential near 0 V and transports electrons from Complex I to Complex III. Cytochrome C has a reduction potential of +280 mV: between the reduction potentials of cytochrome $c_1$ (+250 mV, Complex III reductase subunit) and Cytochrome $b_1$ (+290 mv, Complex IV oxidase subunit).

Antioxidant Nanoparticles Having Attached Chelating Moieties

The treatment of the present invention includes a carbon nanoparticle covalently modified with an iron-chelating moiety. These particles are termed DEF-PEG-HCCs (deferoxamine-pegylated-hydrophilic carbon clusters) and are extended from previous work of the Applicants covering the enormous antioxidant capabilities and applications of PEG-HCCs.

Synthesis

In embodiments of the present invention, PEG-HCCs are synthesized as previously described, such as Samuel, et al., "Highly efficient conversion of superoxide to oxygen using hydrophilic carbon clusters," *Proc Natl Acad Sci USA* 2015, 112(8):2343-8 ("Samuel 2015") and Bitner et al., "Antioxidant carbon particles improve cerebrovascular dysfunction following traumatic brain injury," *ACS Nano.* 2012; 6(9): 8007-14.

For example, the carbon core of the PEG-HCCs can be prepared by subjecting purified (removing exogenous carbon black and gross metal contaminants) single-walled carbon nanotubes (SWCNTs) to a harsh oxidation procedure which uses fuming sulfuric acid (excess $SO_3$, oleum) and nitric acid. Nitric acid initiates the oxidation and cutting process which both shortens the SWCNTs to ~35-40 nm and splits them to remove any tubular residues, thus generating shorten oxidized HCCs. Harsh acidic conditions dissolve and remove even trace metal contaminants as determined by inductively coupled plasma mass spectrometry. The surface of the HCCs is functionalized with various oxygen-containing moieties such as alcohols, ketones, and carboxylic acids, rendering the HCCs water insoluble despite of their many remaining hydrophobic domains.

Graphene quantum dots (GQDs) are synthesized from either anthracite or bituminous coal using a 1:1 mixture of fuming sulfuric and fuming nitric acid (FIG. 1). This is analogous to yet a more harshly oxidizing set of conditions relative to what has been published wherein fuming acid was used rather than merely concentrated acid. See Ye, R. et al., "Bandgap Engineering of Coal-Derived Graphene Quantum Dots," *ACS Appl. Mater. Interfaces* 2015, 7, 7041-7048; Ye, R. et al., "Coal as an Abundant Source of Graphene Quantum Dots," *Nature Commun.* 2013, 4:2943, 1-6.

Figure 2:
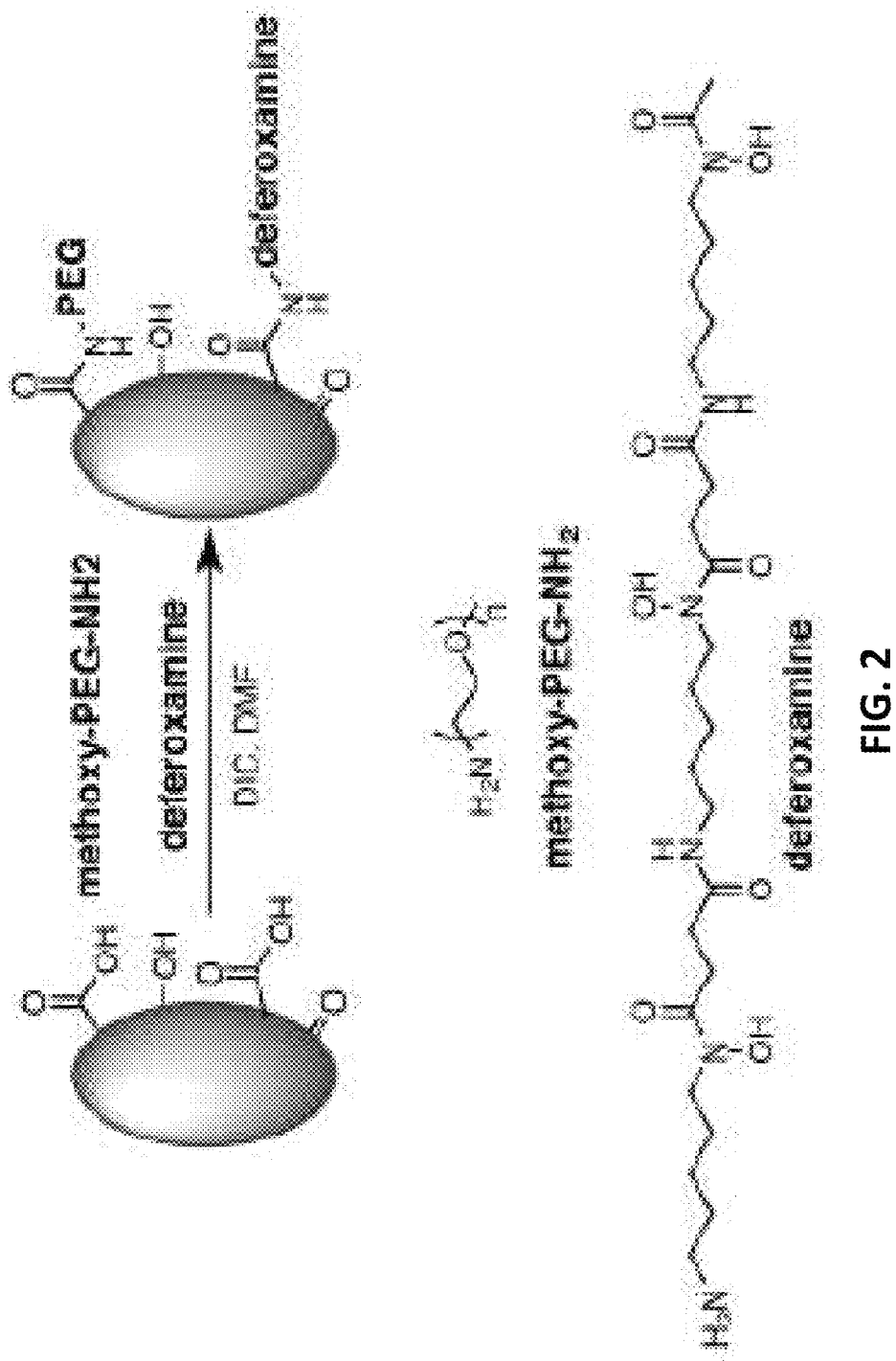
FIG. 2 shows a synthesis of deferoxamine-PEG-HCCs (DEF-PEG-HCC) or deferoxamine-PEG-GQDs (DEF-PEG-GQD) where the DEF is attached through its terminal amine to form a new amide bond.

Deferoxamine is attached to HCCs and GQDs using its primary amine group with carbodiimide crosslinker coupling with DIC, attaching deferoxamine via an amide bond. Methoxy-PEG-amine is attached in the same way, and deferoxamine-PEG-HCCs are synthesized by co-reacting the HCCs or GQDs with both the amino-PEG and deferoxamine as shown in FIG. 2. The ratio of PEG:deferoxamine can be varied and optimized if needed based on initial biological activity results. For example, the ratio of PEG: DEF can be between 1:3 and 3:1, and generally is below 1:1. Purification is carried out in the same manner as with PEG-HCCs via crossflow (KrosFlow Instruments Inc.) tangential flow filtration or dialysis.

Characteristics

PEG-HCCs are a novel carbon nanoparticle that overcomes major limitations of current antioxidants by possessing an enormous, catalytic capacity activity against superoxide, are equally effective against hydroxyl radical while sparing the vasoprotective molecule nitric oxide. These particles have shown remarkable efficacy in reversing loss of cerebral autoregulation and improving outcome due to brain trauma in rats after intravenous injection.

Figure 3:
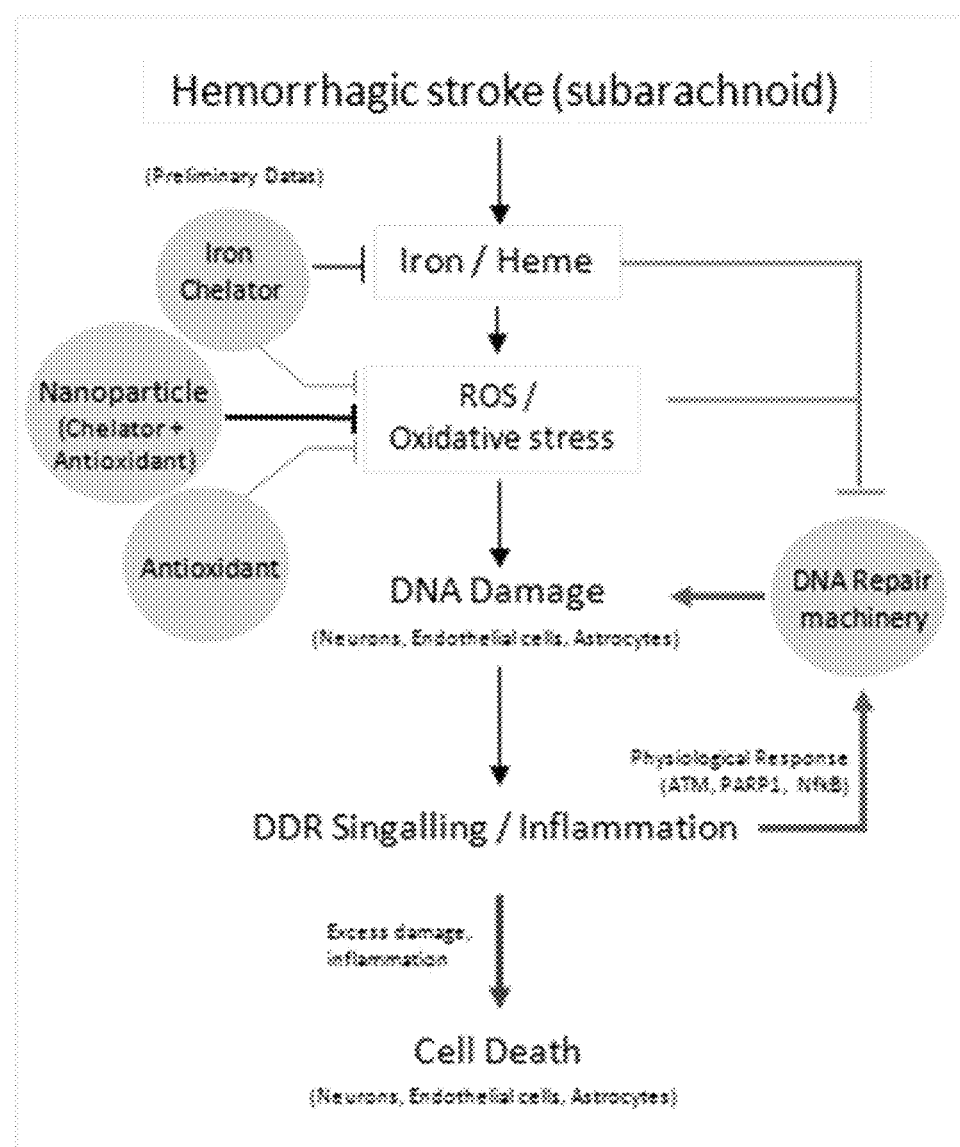
FIG. 3 depicts the role of iron/hemin in mediating genome damage via ROS and oxidative stress. Treatment with nanoparticle (in combination with chelator plus antioxidant is believed to protect genome damage in stroke.)

It has been discovered that, while scavenging ROS, PEG-HCCs release oxygen in 1:1 stoichiometry with consumption of SO radicals, a characteristic that would be particularly beneficial in the context of oxidative injury and loss of normal blood supply termed ischemia. Finally, the available functional groups on PEG-HCCs permit covalent binding of a variety of moieties. Results indicated these nanoparticles are able to salvage neurons and vascular endothelial cells in culture from the lethal effects of heme/iron or the direct application of hydrogen peroxide even when administered after toxin, as would be essential in treating patients following ICH. Because oxidative injury from the presence of hemoglobin and its byproducts is ongoing in patients, this provides for synergistic benefit from the addition of chelation to the acute protective ability of the PEG-HCCs (FIG. 3). It is believed that ICH or subarachnoid hemorrhage (SAH) breakdown products generate specific types of oxidative DNA damage and inhibited DNA repair in neurons, astrocytes and endothelial cells. It is further believe that these events are improved with a combination of PEG-HCCs and metal chelation.

DEF-PEG-HCC Reduction of CellROX ROS

Figure 4B:
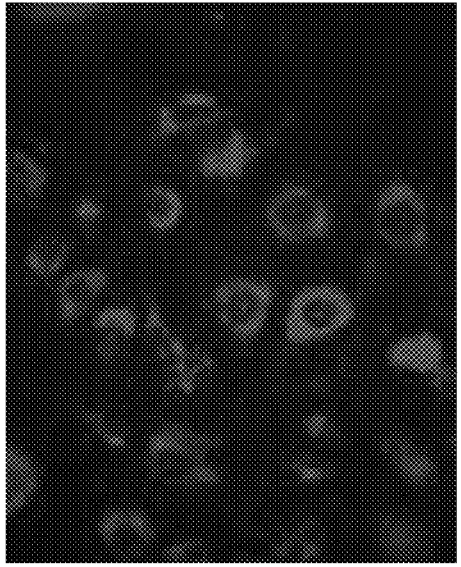
FIGS. 4A-4C shows CellROX™ fluorescence reflecting levels of reactive oxygen species in cultured vascular endothelial cells.
Figure 4C:
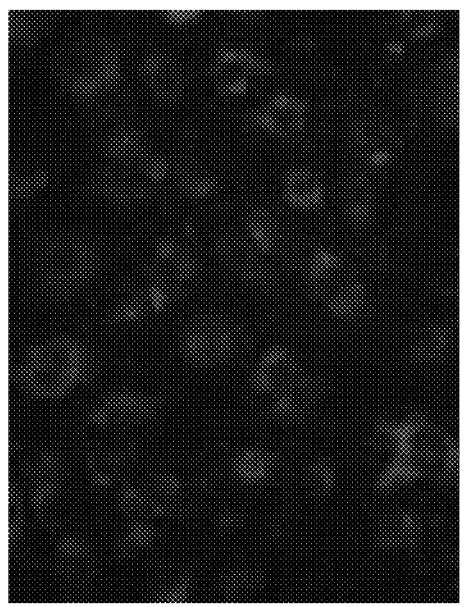
Figure 4A:

DEF-PEG-HCCs were tested against hemin in murine brain endothelial cells using a CellROX ROS accumulation assay (using iron(III) trinitrilotriacetate). The results are shown in FIGS. 4A-4C. FIG. 4A is the control. FIG. 4B is the cellular fluorescence following administration of iron elevates ROS, which (in FIG. 4C) is completely reversed by addition of PEG-HCCs at a concentration achievable in-vivo (4 mg/ml) following the iron administration (cells treated with hemin one hour later DEF-PEG-HCCs assayed at 24 hours).

As shown in FIGS. 4A-4C, PEG-HCCs were able to reverse the increase in ROS induced by direct application of iron to culture endothelial cells (and neuronal cell, not shown) in concentrations that are achievable after intravenous injection in-vivo without evidence of toxicity. These results support utilizing novel variations on PEG-HCC by covalently binding deferoxamine and using it in murine SAH.

CellROX ROS Assay in Murine Cortical E17 Neurons

Figure 5E:
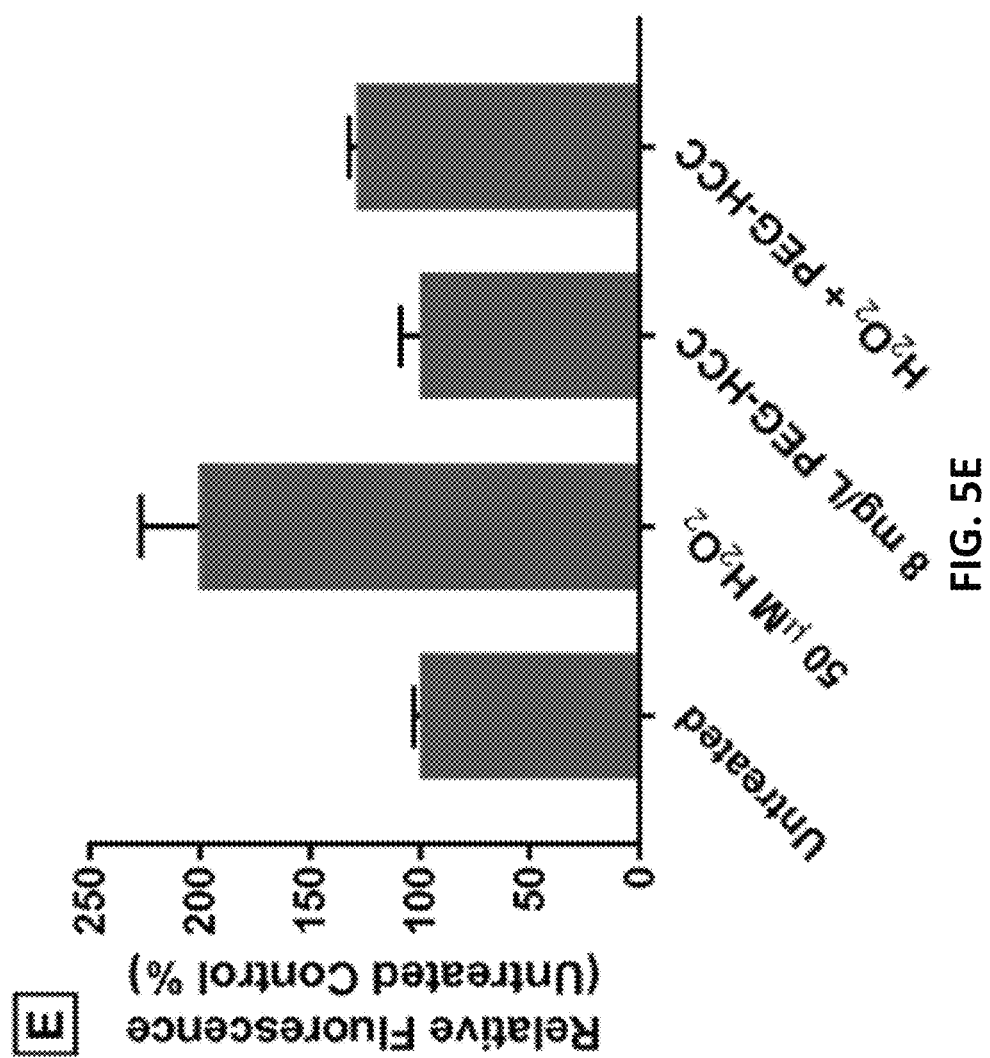
FIG. 5E is a graph showing untreated control-normalized fluorescence of oxidized CellROX dye for the PEG-HCCs of FIGS. 5A-5D.

ROS formation was measured using a CellROX assay in cultured murine neurons. FIGS. 5A-5D show hydrophilic carbon clusters, conjugated to poly(ethylene glycol) (PEG-HCCs) reduce the oxidation of CellROX fluorescent dye in primary murine cortical neurons by hydrogen peroxide. FIG. 5A shows MCNs (50,000 cells/well) untreated. FIG. 5B shows MCNs treated with 50 μM $H_2O_2$ for 45 min. FIG. 5C shows MCNs treated with 8 mg/L PEG-HCCs for 45 min. FIG. 5D shows MCNs treated with 50 μM $H_2O_2$ for 15 min followed by the addition of 8 mg/L PEG-HCCs for an additional 30-min exposure. FIG. 5E is a graph showing untreated control normalized fluorescence of oxidized Cell-ROX dye for the hydrophilic carbon clusters of FIGS. 5A-5D. Total cell counts per condition: untreated (n=137), 50 μM $H_2O_2$ (n=158), 8 mg/L PEG-HCC (n=150), and $H_2O_2$+PEG-HCC (n=139).

E17 cells treated with PEG-HCCs showed no increase in CellROX fluorescence compared with the untreated control (100.1±8.8%). Cells treated with 50 μM $H_2O_2$ for 15 min showed a significant increase in CellROX fluorescence (200±26.5%). Treatment of MCNs with 8 mg/L PEG-HCCs following 15 min of $H_2O_2$ exposure for 30 min showed an increase in CellROX fluorescence of 129±3.4% but was smaller than with $H_2O_2$ by itself. Cell viability was reduced after administration of 50 μM $H_2O_2$ by 20% and was fully restored by PEG-HCCs treatment.

Effects of DEF-PEG-HCCs on DNA Damage Markers

Figure 6C:
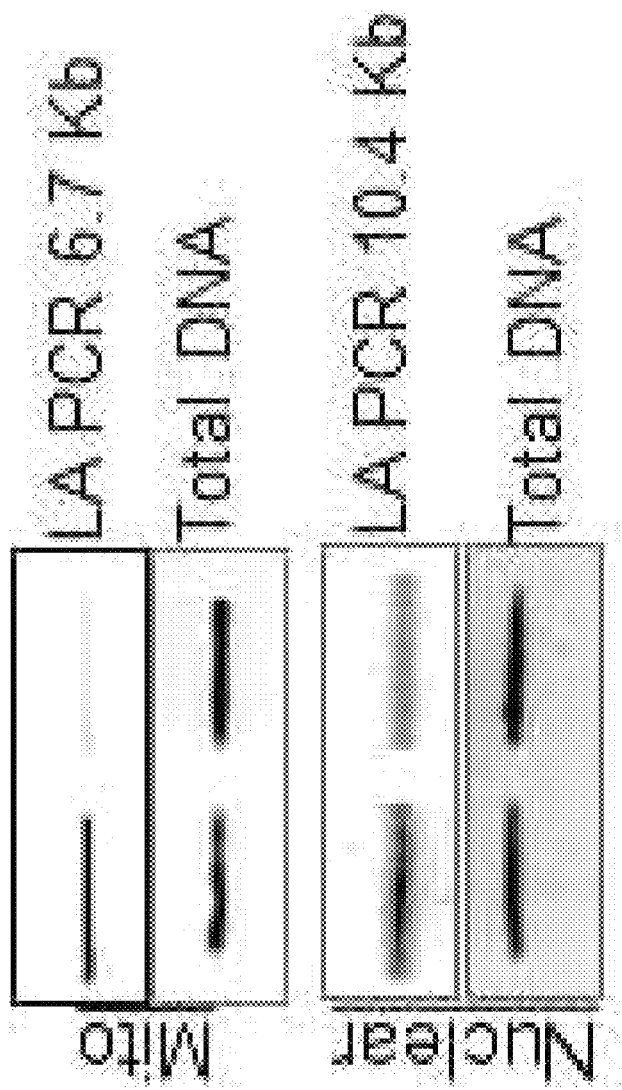

FIGS. 6A-6E illustrates additional in-vitro and in-vivo data related to the mechanism of action involved improvement of the DNA damage response to iron and reactive oxygen toxicity. FIG. 6A-6B show mitochondria specific $H_2O_2$ sensor pHyper fluorescence within 15 min of iron exposure in neurons (FIG. 6A at 0 minutes and FIG. 6B at 15 minutes). FIGS. 6A-6B illustrate the rapid effect of addition iron to cultured neurons in elaboration of reactive oxygen species in the mitochondria.

Figure 6D:
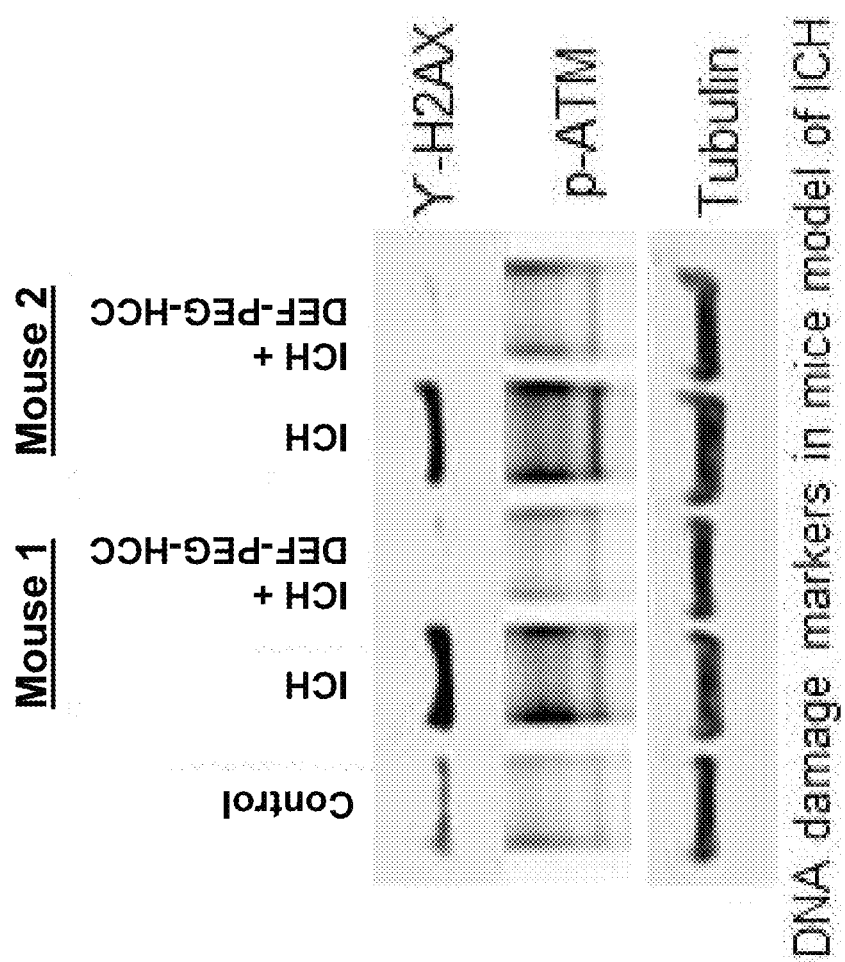
Figure 6E:
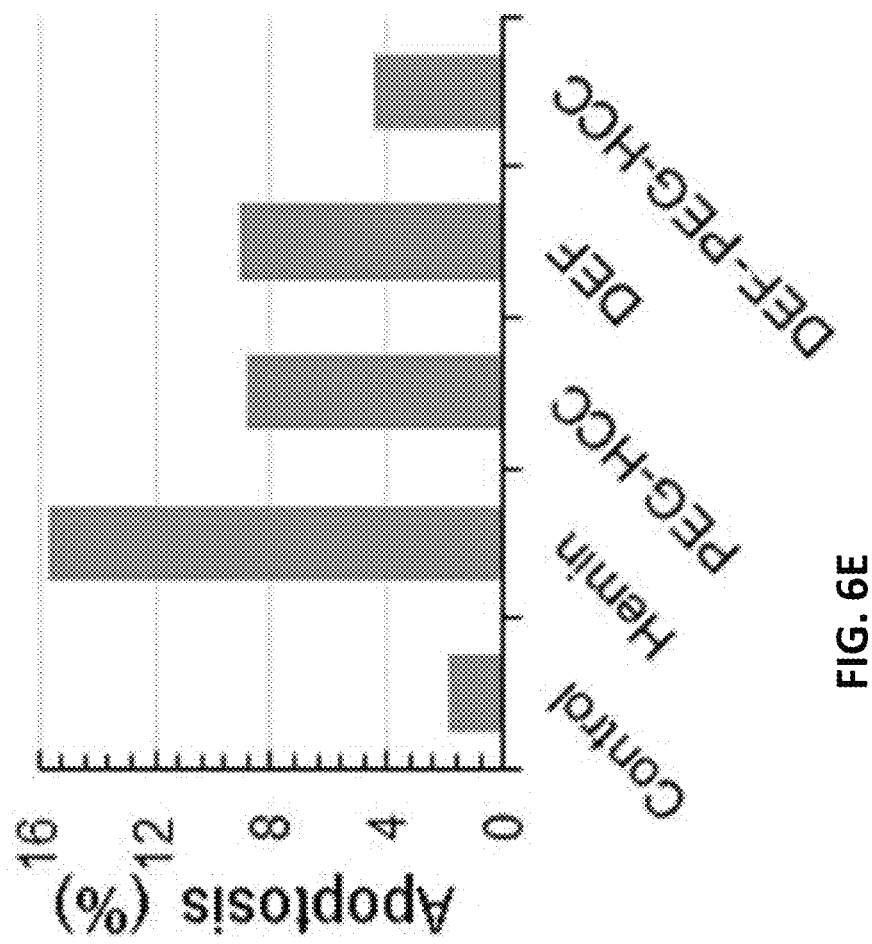

FIG. 6C illustrates that DNA is damaged (lane 2) in both mitochondria and nucleus by the hemoglobin breakdown product hemin. FIG. 6D demonstrates that following experimental intracerebral hemorrhage (ICH) in mice, there is evidence of DNA damage in the peri-hemorrhage region of the brain. FIG. 6E indicates the DEF-PEG-HCC reduces this DNA damage when treated following the ICH better than PEG-HCC or deferoxamine individually.

Figure 7:
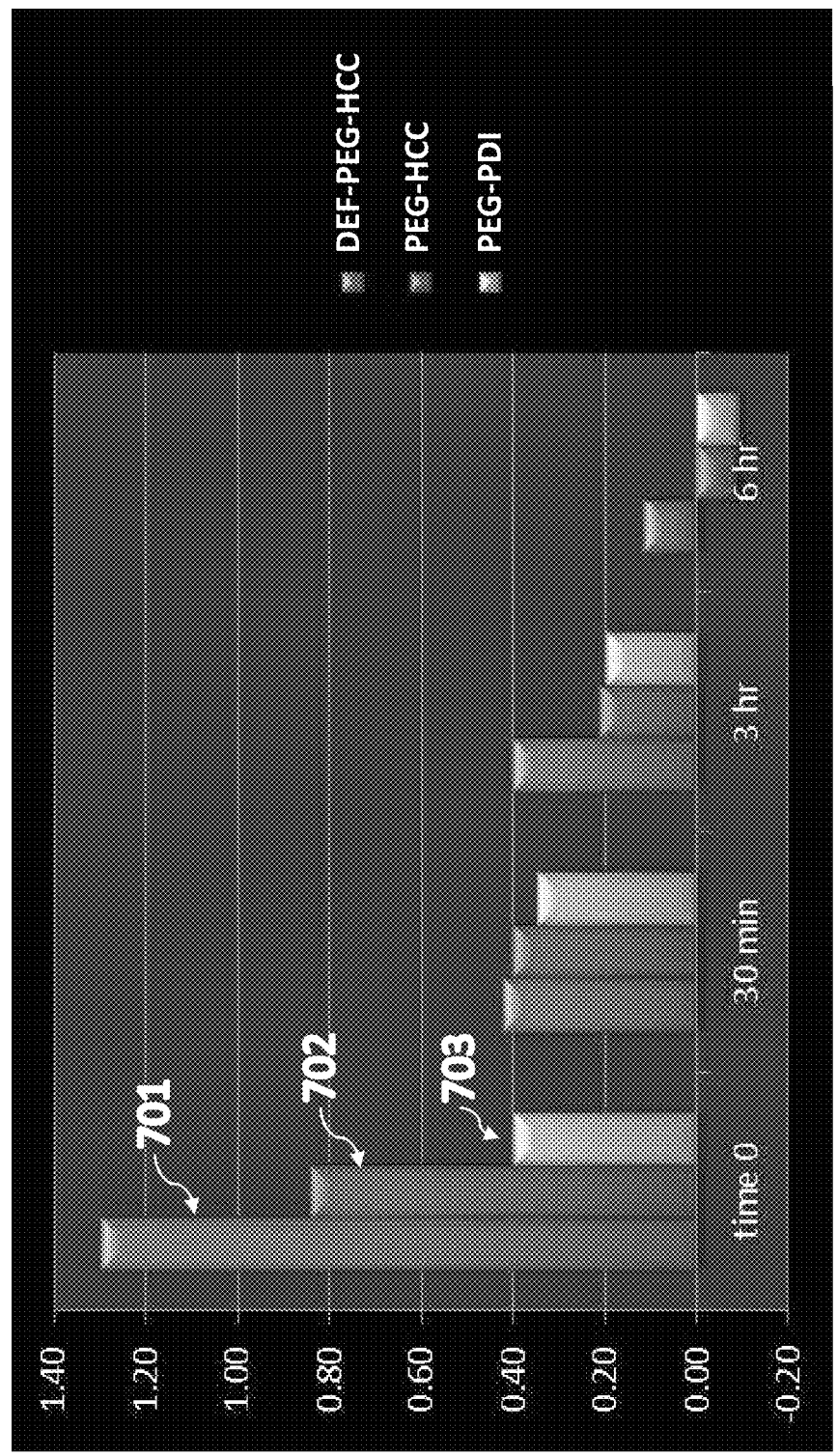
FIG. 7 shows survival of cultured vascular endothelial cells treated with 100 mM hydrogen peroxide and rescued with either PEG-HCCs, DEF-PEG-HCCs, or PEGylated perylenediimide (PEG-PDI) measured 24 hours later after addition of DEF-PEG-HCC (701), PEG-HCC (702) or PEG-PDI (703). PEG-PDI is PEGylated perylenediimide. The times from addition of hydrogen peroxide is shown on the X axis. Superior protection ability from the DEF-PEG-HCC is particularly prominent when added at the same time as the hydrogen peroxide.

FIG. 7 shows cell survival compared to 100 mM hydrogen peroxide in cultured bEnd0.3 murine endothelioma cells and measured 24 hours later. Y-axis is survival percentage compared to hydrogen peroxide alone and the X-axis is the time of treatment relative to the hydrogen peroxide. DEF-PEG-HCC (701) was superior to PEG-HCC alone (702) and the small molecule PEG-PDI (703) with maximal protection evident when added simultaneously with the hydrogen peroxide (time 0). Some protection was evidenced as late as when added at 3 hours.

FIG. 7 illustrates that DEF-PEG-HCCs are superior to either PEG-HCC alone or the graphene-like small molecule PEG-PDI at protection against the lethal effects of hydrogen peroxide when applied to cultured brain endothelial cells (b.End3 cells) at 24 hours after hydrogen peroxide was administered. The protection was complete (percent survival compared to cells treated with hydrogen peroxide; y-axis) when added simultaneously with the hydrogen peroxide (time 0) and sustained some protection even when added at times after the hydrogen peroxide, supporting that treatment can be delayed providing a realistic clinical time window for certain injuries such as ischemic stroke.

Figure 8A:
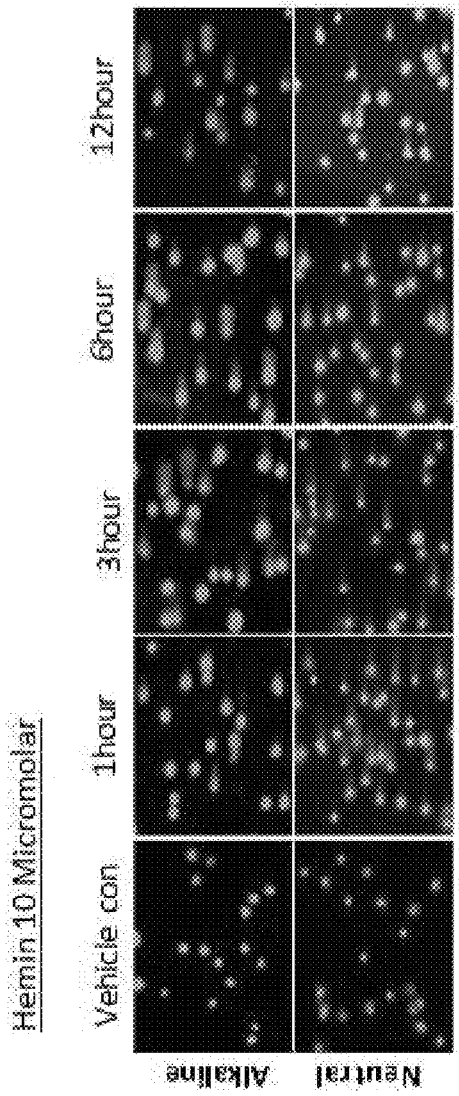
FIG. 8A are images taken of DNA alkaline and neutral comet assays following of DNA damage from exposure to 10 μM hemin.
Figure 8B:
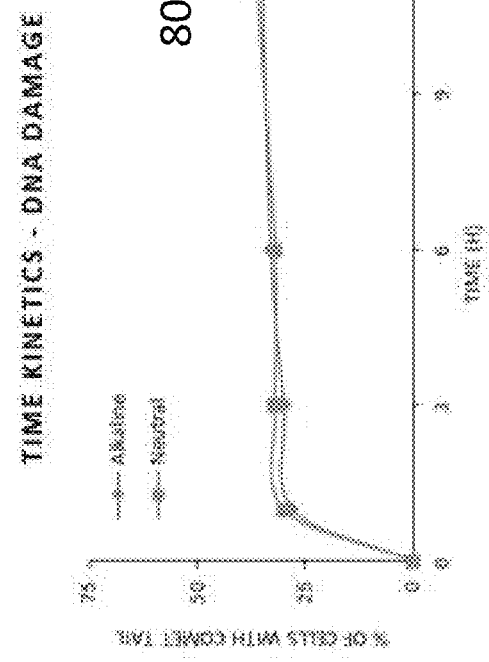
FIG. 8B is a graph showing the time kinetics of DNA damage of the assays shown in FIG. 8A.

DNA damage occurs using 10 μM hemin in differentiated SHSY-5Y neurons. FIG. 8A are images taking over 12 hours of DNA damage that occurs for alkaline and neutral DNA comet assays using 10 μM hemin. FIG. 8B is a graph showing the time kinetics of DNA damage of these assays (with curves 801-802 for the alkaline and neutral assays).

Alkaline and neutral DNA comet assays of hemin-treated cells showed remarkable similarities suggesting that most of the DNA damage that occurs with hemin is of the double strand break variety. The DNA damage that occurs following hemin exposure was maintained for at least 12 hours following the initial insult, suggesting that DNA repair mechanisms are impaired. The alkaline comet assay showed both SSB and DSB in DNA and is more sensitive than neutral which tends to only show DSBs.

Figure 9:
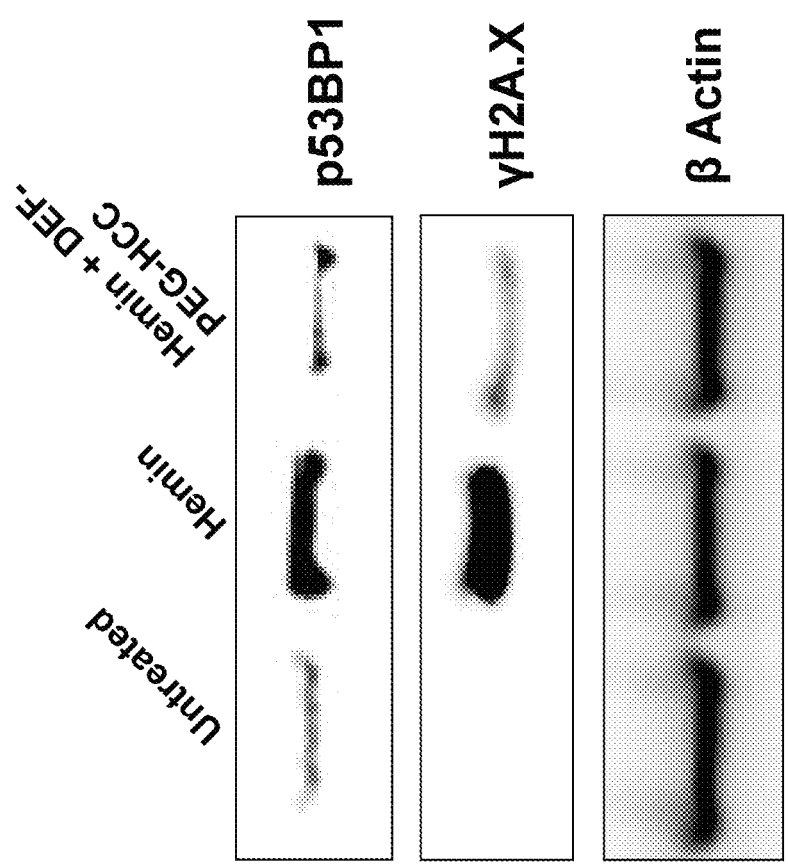
FIG. 9 also shows that DEF-PEG-HCC reduces double strand break (DSB) markers following hemin exposure.

FIG. 9 also shows that DEF-PEG-HCC reduces double strand break markers following hemin exposure. Two markers of DSB: p53BP1 and phosphorylated γ-H2A.X were measured in untreated, hemin-treated, and hemin-DEF-PEG-HCC-treated cells. Following treatment with hemin, the DSB marker expression increases relative to the control. In cells treated with hemin and DEF-PEG-HCCs, p53BP1 and γ-H2A.X expression is suppressed indicating a reduction in DSB formation. H2A.X becomes phosphorylated when dsDNA strand breaks occur. 53BP1 inhibits resection of the dsDNA and promotes non-homologous end joining which is error prone but faster. Reduction in p53BP1 is necessary to favor homologous recombination.

Figure 10:
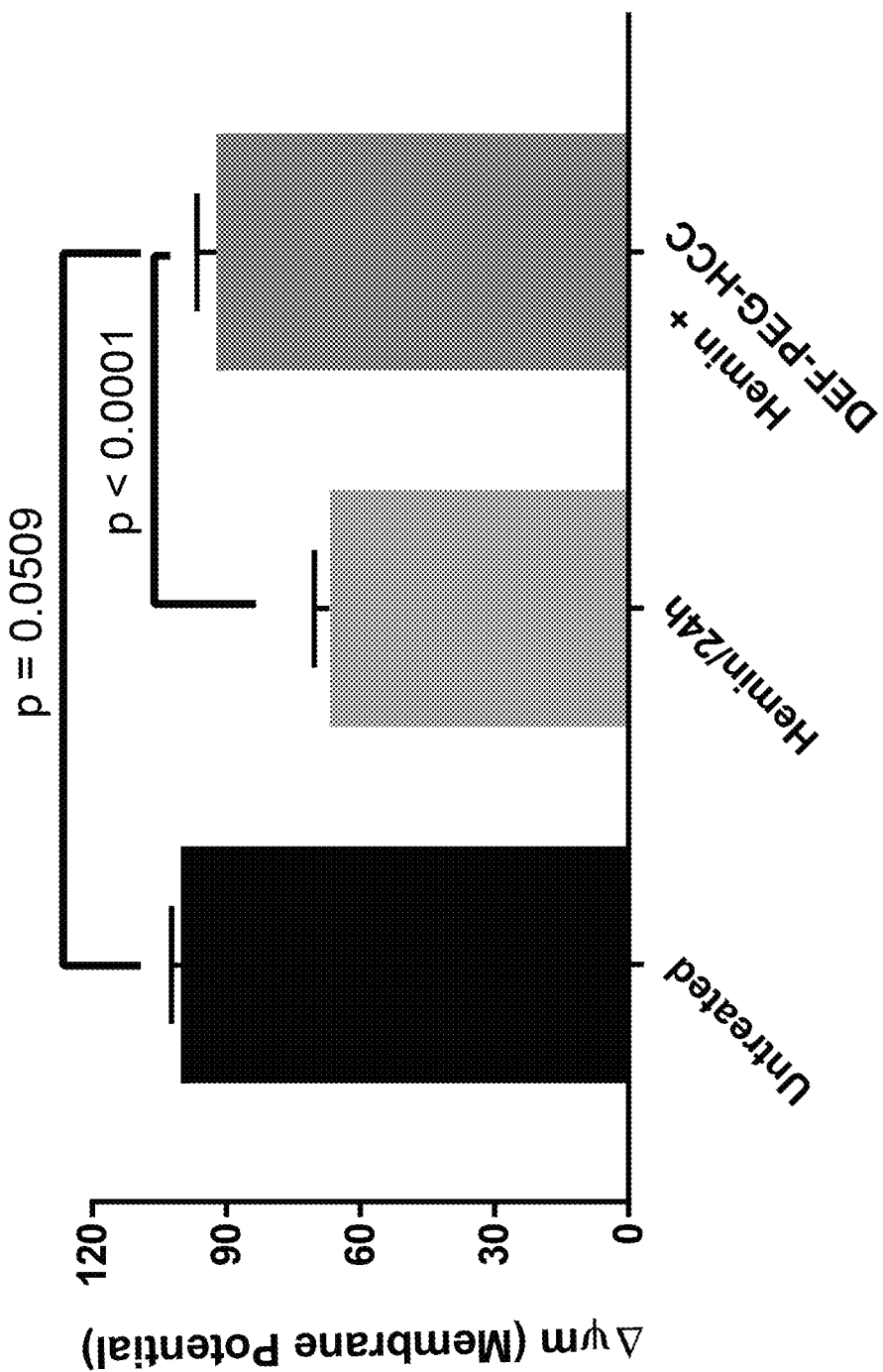
FIG. 10 is a graph showing the effect of hemin on mitochondrial membrane potential and the effect of restoration to baseline by DEF-PEG-HCC as a rescue treatment.

As shown in FIG. 10, the effect of hemin on mitochondrial membrane potential was measured. Chemical oxidants often cause a reduction in mitochondrial membrane potential, which leads to a reduction in ATP synthesis and energy starvation. Cells treated with hemin showed this effect by a significant reduction in MMP. This effect can be mitigated by treating hemin-treated cells with DEF-PEG-HCCs with no significant difference compared to the untreated cells if given one hour after exposure to hemin.

Figure 11A:
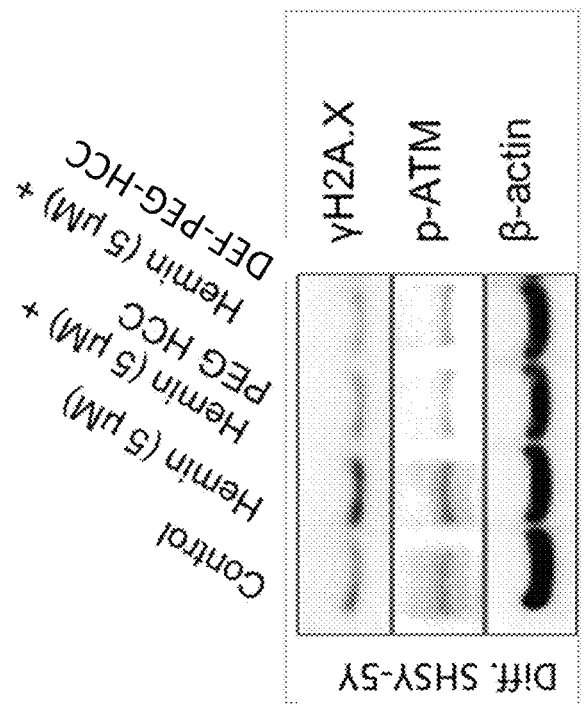
FIGS. 11A-11B is a comparison of the effect of PEG-HCC to DEF-PEG-HCC on DNA damage proteins after addition of iron (Fe) or hemin to both hemin and iron trinitrilotriacetate-treated SHSY-5Y cells.
Figure 11B:
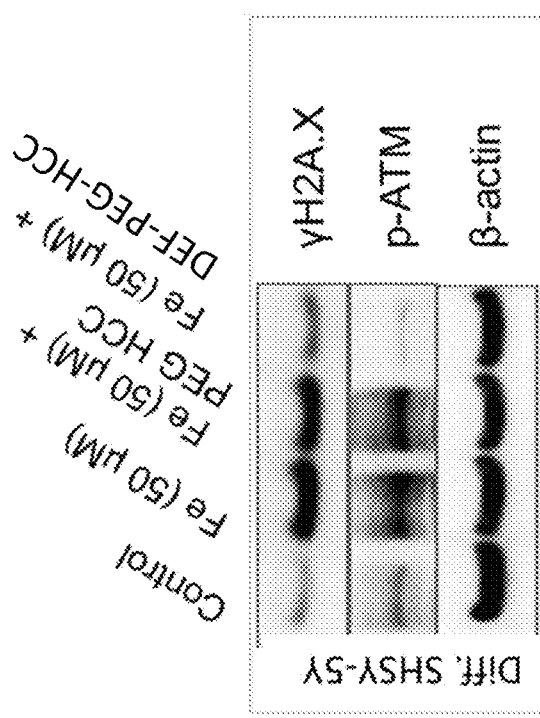
Figure 11C:
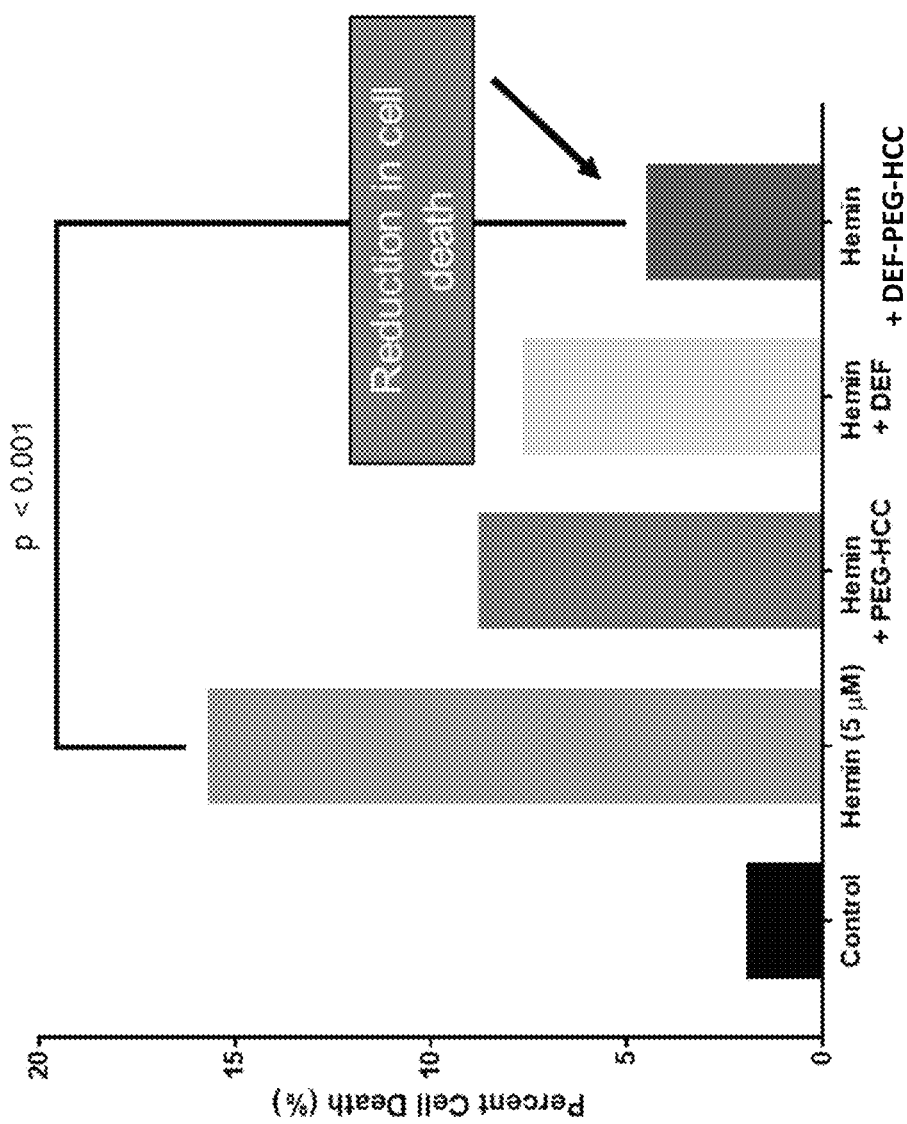
FIG. 11C is a graph showing the percentage of cell death to treatments using an Annexin V cell viability assay after addition of Hemin in cell culture comparing PEG-HCC, DEF-PEG-HCC and deferoxamine alone

DNA damage marker reduction by DEF-PEG-HCC and PEG-HCC was tested in cultured SHSY-5Y cells treated with hemin and iron trinitrilotriacetate PEG-HCCs and deferoxamine in two assays. In FIGS. 11A-11B, for γ-H2A.X and pATM (a cellular senescence promotor) it is seen in that the DEF-PEG-HCC is particularly better than PEG-HCC alone with respect to iron (and is equally good to hemin). As shown in FIG. 11C, in a cell death assay, it was found that hemin promotes death, and that DEF-PEG-HCC is better than either PEG-HCC or DEF alone. At maximally protective concentrations of DEF and PEG-HCC, DEF-PEG-HCC is better at preventing cell death.

Figure 12:
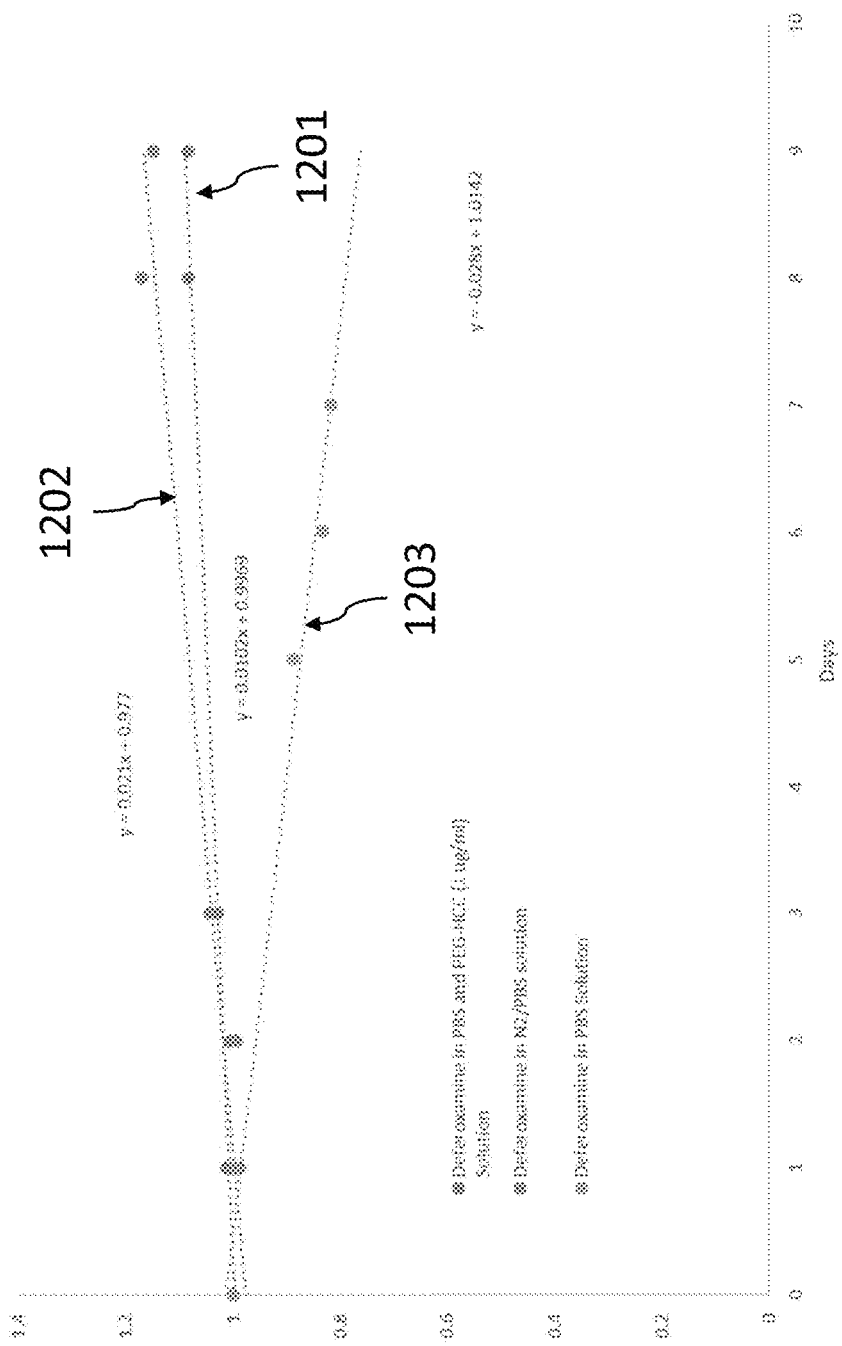
FIG. 12 is a graph in which Y-axis is units of deferoxamine remaining in solution through monitoring of the 262 nm absorbance by UV spectroscopy. Trend line 1203 illustrates deferoxamine degradation in PBS solution (DEF/PBS). Trend line 1201 illustrates the degradation of deferoxamine in a PBS solution and dilute PEG-HCC (DEF/PEG). Trend line 1202 illustrates deferoxamine degradation in a PBS that had nitrogen gas bubbled through it (DEF/$N_2$). The slopes DEF/PEG and DEF/$N_2$ indicate that there was no detectable degradation in the deferoxamine dissolved in the solutions when either $N_2$ purged of when the antioxidant PEG-HCC was present. This DEF-PEG-HCC should be far more stable than DEF alone in PBS solution.

An additional advantage of this formulation is that it prevents the oxidative breakdown of the deferoxamine molecule, likely through an interaction with the antioxidant capacity of the parent nanomaterial (FIG. 12). This is a tremendous advantage clinically because current deferoxamine has a short shelf life when prepared for intravenous administration, which could be dramatically extended through this formulation and thereby be useful for settings other than the hospital, such as in a battle field, automobile trauma, or other setting in which tissue injury must be rapidly treated.

DEF-PEG-HCC Reduction of Brain H2A.X Phosphorylation (γH2A.X)

It was found that, in vivo, DEF-PEG-HCC reduces brain H2A.X phosphorylation (γH2A.X), in-mouse at 24 hours when administered one hour following brain infusion of hemolyzed blood. DEF-PEG-HCCs in-vivo and the expression of γH2A.X were tested using stereotactically injected mice with hemolyzed blood into one hemisphere. (See FIG. 13A). Hemolyzed blood was used to more rapidly mimic the hemoglobin breakdown products in this experiment.

Figure 13B:
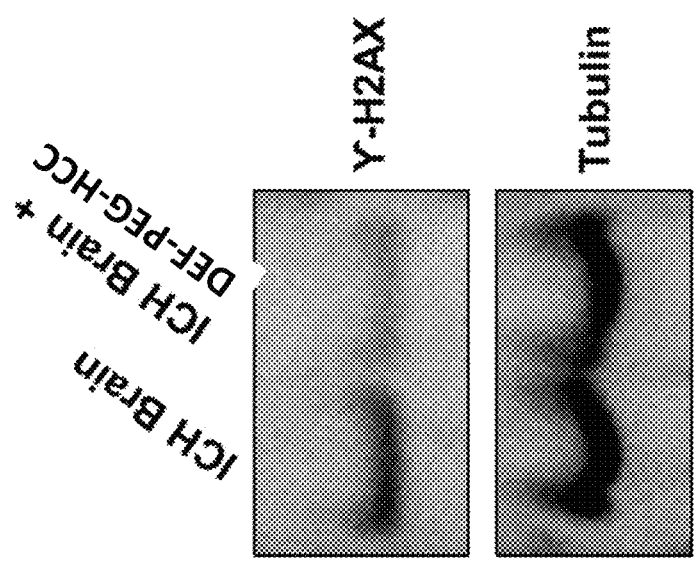
FIG. 13B shows γH2A.X DNA damage marker expression in homogenized mouse brain tissue treated with or without the presence of protein associated with DNA damage DEF-PEG-HCCs in hemolyzed blood-injected mice of FIG. 13A.
Figure 13A:
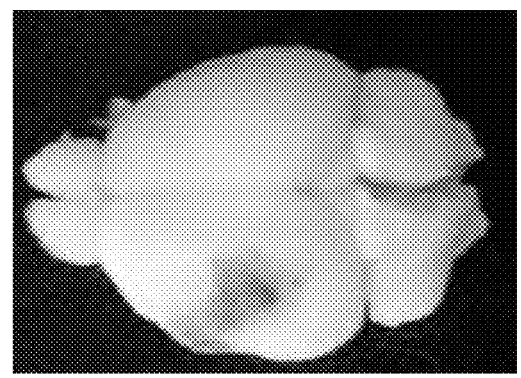
FIG. 13A is a photograph of showing the injected hemolyzed blood into one hemisphere of an injected mouse.

One hour after injection of hemolyzed blood, the mice were treated intraperitoneally with DEF-PEG-HCCs. At 24 hours, the brain was sampled for γH2A.X in the area surrounding the injection. As shown in FIG. 13B, there is a reduction in the double strand break marker for the mice that received DEF-PEG-HCCs, as compared to the mice that did not receive DEF-PEG-HCCs.

In Vivo tMCAO

Seventy-two rats underwent the procedure. Fifty-eight met criteria for outcome analysis. In the 90-min occlusion, four PBS- and one PEG-HCC-treated rats were excluded, and in the 120-min occlusion group, seven PBS- and two PEG-HCC-treated rats were excluded, primarily for early illness/mortality or procedural problems identified by the operator before assessment of outcomes.

Figure 14A:
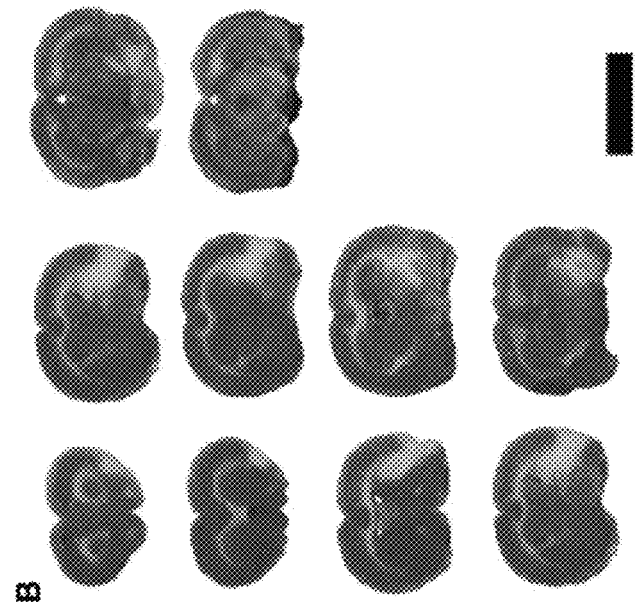
FIGS. 14A-14B are representative tetrazolium chloride sections demonstrated infarct volume with PBS control treatment and hydrophilic carbon cluster, conjugated to PEG-HCC treatment following 90-min ischemia and reperfusion.
Figure 14B:
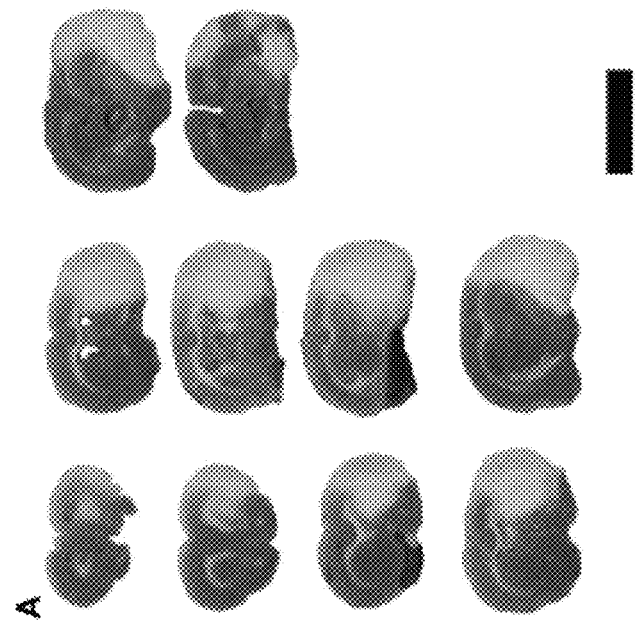

The target of 300 mg/dL preoperative glucose was achieved in the 90-min group. PBS-treated rats showed complete MCA territory infarction (FIG. 14A) while PEG-HCCs treated rats showed mostly subcortical infarctions (FIG. 14B). Quantification of outcome measures (shown in TABLE 1) demonstrated that PEG-HCC treatment improved infarct volume, hemorrhagic conversion, hemisphere swelling and Bederson score, with a trend toward reduced mortality.

TABLE 1

| | PBS (n = 17) | PEG-HCC (n = 16) | p-Value |
|---|---|---|---|
| Glucose (mg/dL) | 274 ± 69 | 299 ± 67 | 0.35 |
| pO$_2$ | 145 ± 19.9 | 144 ± 19.8 | 0.92 |
| pCO$_2$ | 40.2 ± 3.15 | 40.1 ± 5.99 | 0.96 |
| pH | 7.33 ± 0.038 | 7.34 ± 0.061 | 0.68 |
| Lesion volume (mm$^3$) | 275 ± 52 | 161 ± 84 | 0.03* |
| Hemisphere volume change (relative) | 12 ± 4.5% | 6.5 ± 5.1% | 0.027* |
| Hemorrhage score | 1.75 ± 1.16 | 0.83 ± 0.88 | 0.068 |
| Mortality rate | 5/17 | 1/16 | 0.175 |
| Modified Bederson score | 3.6 ± 1.5 | 1.51 ± 0.97 | 0.001* |

The mean overall survival was 2.8 days. Groups did not differ with respect to baseline glucose just before tMCAO or in blood gas parameters taken from a sample of each group. All outcomes were in the direction of improvement with PEG-HCC treatment with controls.
*P < 0.05.

Survival was markedly diminished at the 120-min time point in the PBS-treated controls, such that no rats survived the day of procedure at the original target glucose (300 mg/dL). The streptozotocin dosing was subsequently until a target of 200 mg/dL glucose was achieved at the onset of the tMCAO procedure. Survival without apparent discomfort to at least 24 hours marginally improved in the PBS-treated controls. However, this limited the information that could be obtained from the control group; thus this time point was not pursued to full completion. Rats that required sacrifice before 12 hours postprocedure were not assessed for infarct characteristics as it was felt that this would be unreliable. In this time point, positive trends were observed in all measures, with significance achieved in the infarct volume, as shown in TABLE 2.

TABLE 2

| | PBs (n = 47) | PEG-HCC (n = 11) | p-Value |
|---|---|---|---|
| Glucose (mg/dL) | 199 ± 42 | 203 ± 46 | 0.900 |
| pO$_2$ | 151 ± 12.6 | 149 ± 12.2 | 0.737 |
| pCO$_2$ | 4.9 ± 4.18 | 43.1 ± 7.38 | 0.447 |
| pH | 7.36 ± 0.047 | 7.32 ± 0.033 | 0.056 |
| Lesion volume (mm$^3$) | 259 ± 121 | 130 ± 87 | 0.034* |
| Hemisphere volume change (relative) | ND | ND | |
| Hemorrhage score | ND | ND | |
| Mortality rate | 9/14 | 3/11 | 0.111 |
| Modified Bederson score | 4.8 ± 2.4 | 2.1 ± 1.8 | 0.055 |

The mean overall survival was 2.1 days. Glucose targets were lowered to improve survivability of the procedure. Groups did not differ with respect to baseline glucose just before tMCAO or in blood gas parameters from a representative sample except for trend toward lower pH in the PBS group. All outcomes were in the direction of improvement with PEG-HCC treatment compared with controls with significance achieved with modified Bederson Score.
ND: not done because of premature termination of the experiment (see text).
*P < 0.05.

Actions of DEF-PEG-HCC in Ferroptosis

Figure 15:
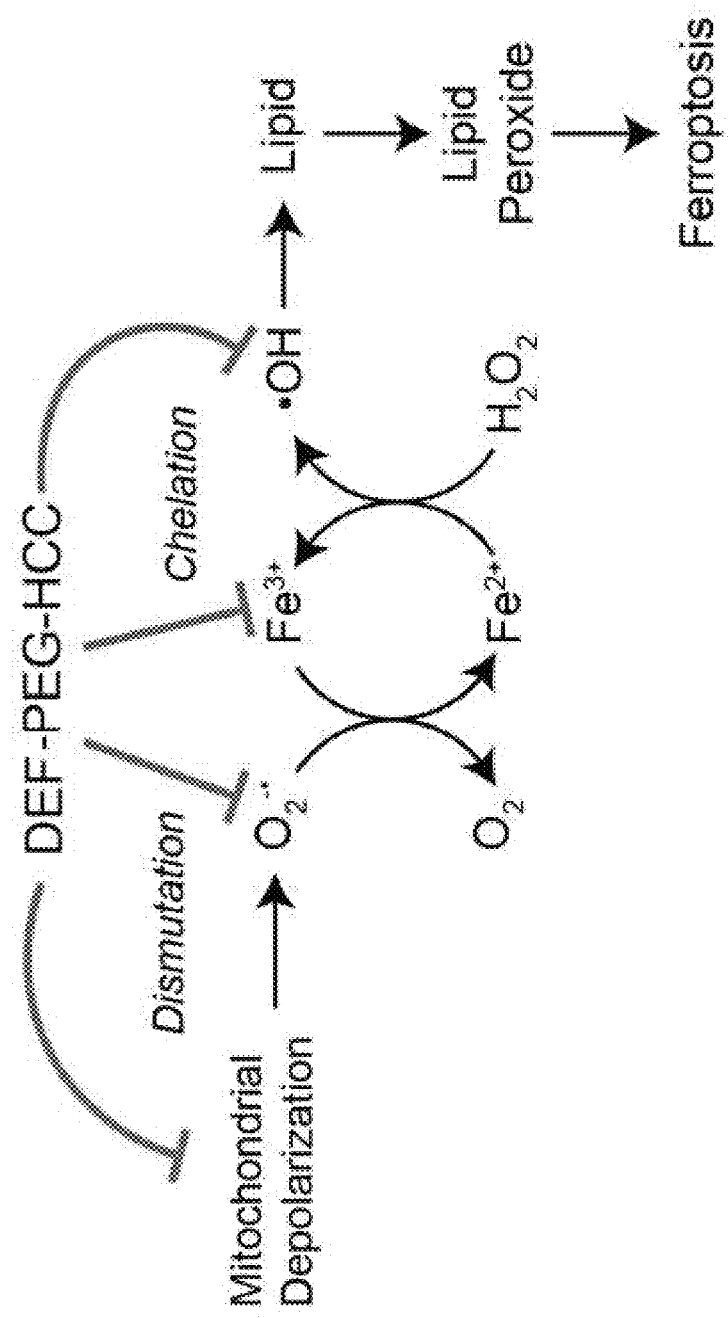
FIG. 15 shows the ferroptosis pathway and how DEF-PEG-HCC may have multiple effects on this pathway.

Because DEF-PEG-HCC can catalytically dismutate superoxide, annihilate hydroxyl radical, protection mitochondrial polarization and chelate iron, DEF-PEG-HCC may inhibit ferroptosis in the later stages following exposure. As shown in FIG. 15, DEF-PEG-HCC may have multiple effects on the ferroptosis pathway (a) superoxide dismutation, (b) hydroxyl radical annihilation, (c), mitochondrial polarization protection, and (d) iron chelation.

Comparison of ETS Kinetics of MB and PEG-HCCs and Efficacy in H$_2$O$_2$ Protection Assay Methylene blue (MB) is a prototypical electron shuttle with demonstrated clinical efficacy in treating methemoglobinemia by oxidizing NADPH in erythrocytes to reduce methemoglobin to hemoglobin. PEG-HCCs and MB are electrochemically similar with respect to midpoint reduction potentials of +11 mV and ~0 mV respectively, although PEG-HCCs have a much broader range. PEG-HCCs appear to have similar effects on the electron transport chain as described for MB.

To make a more direct comparison of MB to PEG-HCCs, Michaelis-Menten parameters for MB were collected with respect to NADH and CytC$_{ox}$ using a fixed concentration of MB (4 mg/L, 12.5 μM) and CytC$_{ox}$ (40 μM).

Figure 16:
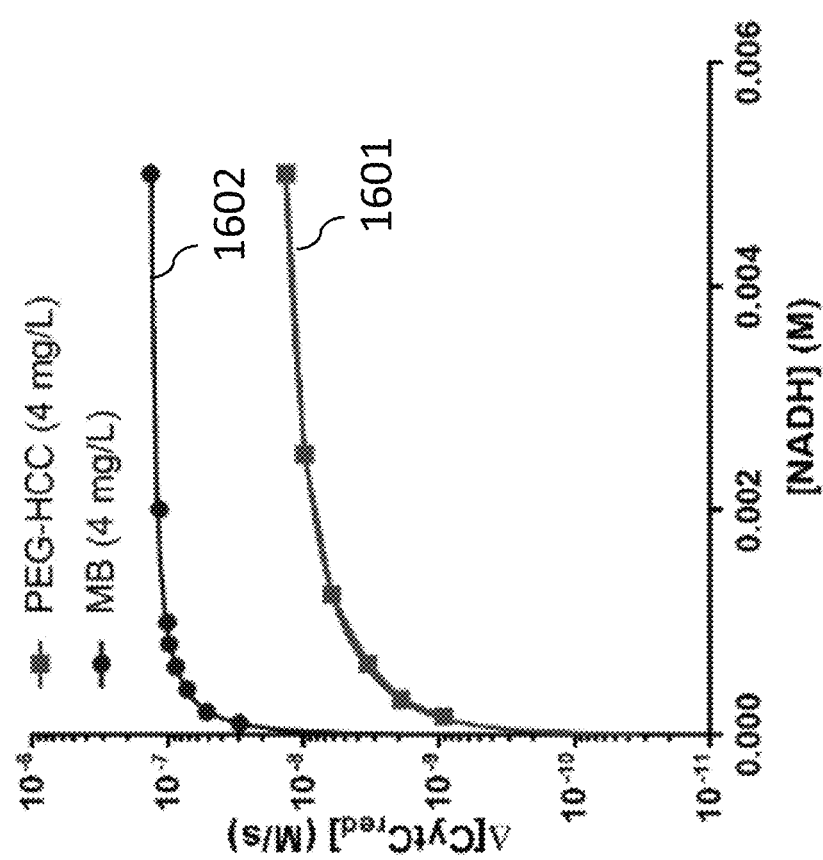
FIG. 16 is a graph showing the comparison of PEG-HCC and methylene blue (MB) at 4 mg/L concentration on reduction of ferricytochrome C ($CytC_{ox}$) (40 μM) by reduced nicotinamide adenine dinucleotide (NADH) (0-5 mM).

Distinct saturation curves 1601-1602 for PEG-HCCs and MB, respectively were obtained using NADH concentrations between 0 and 5 mM as shown in FIG. 16). The calculated V$_{max}$ for MB was significantly higher than the V$_{max}$ for PEG-HCCs (1.432×10$^{-7}$ M/s vs. 2.27×10$^{-8}$ M/s) and the K$_M$ was nearly one order of magnitude lower than that of PEG-HCCs (3.78×10$^{-4}$ M vs. 3.35×10$^{-3}$ M). On a mass concentration basis, methylene blue has a higher Vmax than PEG-HCCs by nearly one order of magnitude. Without NADH, neither PEG-HCCs nor methylene blue reduce cytochrome C.

The electrochemical properties of MB indicated higher affinity and rate of electron shuttling on a mass concentration basis. It is not clear, however, whether these properties will translate to better efficacy against cellular injury. It is possible that higher affinity may compete with normal mitochondrial respiration. During an episode of methemoglobinemia their activity might be helpful, but that might not translate to other conditions such as those that are also accompanied by generation of excess reactive oxygen species. MB does not possess superoxide or hydroxyl radical scavenging functionality. On the other hand, PEG-HCCs scavenge superoxide and hydroxyl radical although they appear to be slower electron shuttles.

The differential properties of MB and PEG-HCCs were tested by using a hydrogen peroxide challenge assay in cultured cells. Hydrogen peroxide exerts toxic effects on endothelial cells through at least four routes: hydroxyl and superoxide radical formation by reacting with reduced species, nitric oxide synthase (NOS) and NADPH oxidase (NOX) stimulation and uncoupling, modulation of mitochondrial permeability, and the Fenton reaction. This employs administering the test agent after the hydrogen peroxide since efficacy under post-injury conditions would be critical for clinical translation.

Figures 17A, 17B:
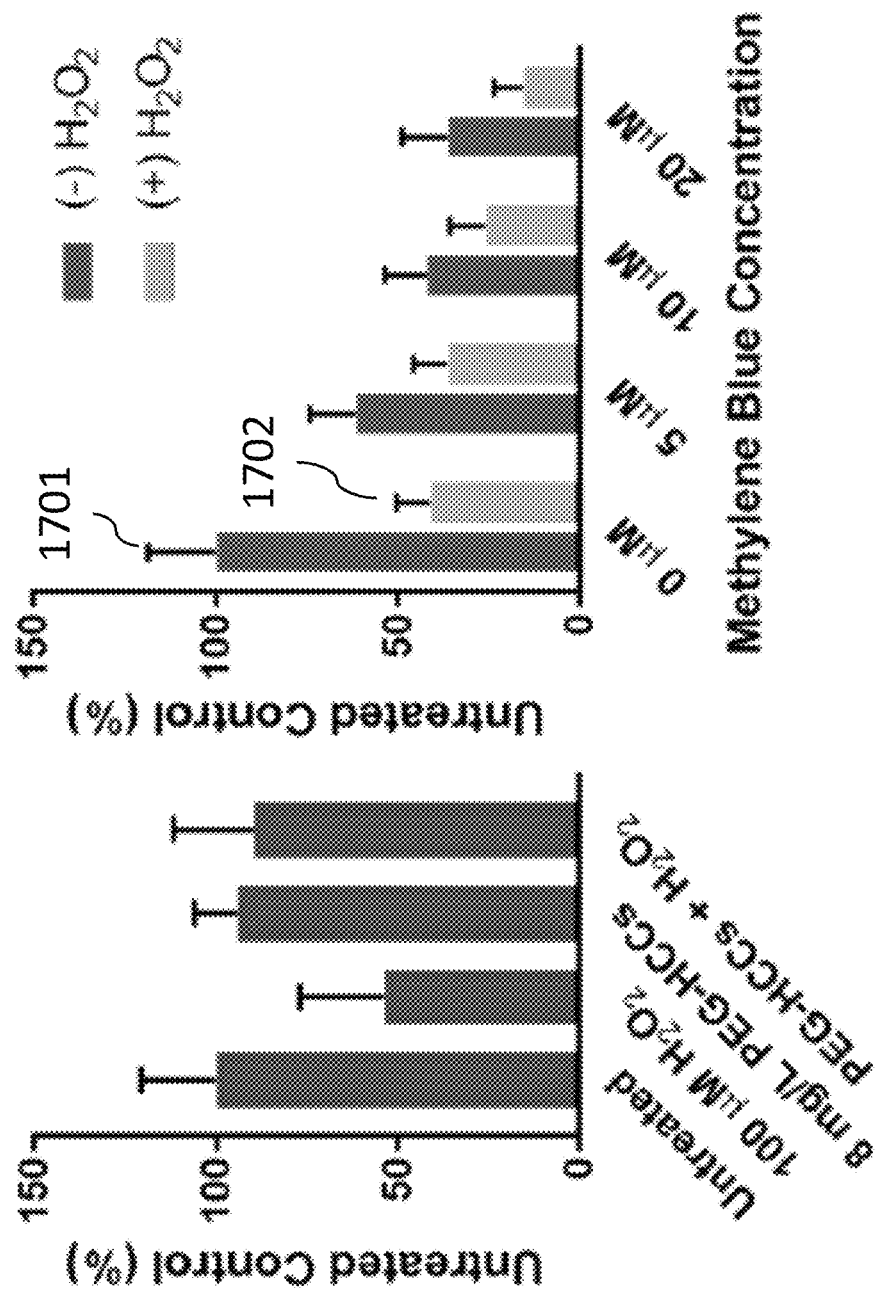
FIGS. 17A-17B are graphs that show PEG-HCCs rescue bEnd.3 cells from hydrogen peroxide toxicity while MB is intrinsically toxic.

PEG-HCCs and MB were compared in two standard hydrogen peroxide challenge assays. In the first experiment, bEnd0.3 murine cerebrovascular endothelial cells were treated with PEG-HCCs, and 100 µM $H_2O_2$ with and without 8 mg/L PEG-HCCs. The cells were incubated overnight and then then detached and counted using a hemocytometer and Calcein AM to label live cells. (Live cell counts n=32). As shown in FIG. 17A, cells treated with PEG-HCCs alone resulted in 94.8% survival, with 100 µM $H_2O_2$, 61.5% of the cells survived, co-treatment with 8 mg/L PEG-HCCs resulted in 93.8% survival.

A similar assay was performed with MB at 0, 5, 10 and 20 µM given 15 minutes after initial exposure to 100 µM $H_2O_2$. As shown in FIG. 17B, in this second challenge assay, there was a dose-dependent reduction in cell survival. The inclusion of 100 µM $H_2O_2$ further reduced survival.

The cytotoxicity of MB in this assay was consistent with effects reported under other conditions. Toxicity has been explained by effects on mitochondrial membrane potential and reactive oxygen species generation. First, because MB is reduced to $MBH_2$ by NADPH, the resulting $MBH_2$ can be oxidized by dioxygen to produce superoxide in situ. Second, MB may be able to decouple the electron transport chain in tightly-coupled mitochondria and lead to a reduction in oxidative phosphorylation. Third, MB is known to directly oxidize glutathione to glutathione disulfide without a hydrogen peroxide intermediate. Finally, a fourth route may also exist, because MB oxidizes NADH to $NAD^+$, and NADH is an inhibitor of the tricarboxylic acid (TCA) cycle, MB may indirectly accelerate glycolysis and lead to a depletion of intracellular glucose and glycogen. One effect seen clinically of this property is a depletion of late glycolysis products in individuals with glucose-6-phosphate dehydrogenase (G6PD) deficiency that can lead to a hemolytic crisis. Additionally, depletion of glucose stores eventually will lead to cell death through ROS-induced cytotoxicity.

Despite PEG-HCCs and MB having similar electron shuttling properties in cell free systems, two key differences exist between PEG-HCCs and MB. First, PEG-HCCs react with superoxide to produce hydrogen peroxide whereas MB tends to generate reactive oxygen species in its reduced state from dioxygen. Second, PEG-HCCs have roughly 0.1× the $V_{max}$ at the same mass concentration as MB, so they are not as strong electron transport chain decouplers.

In Vivo Protection Against $H_2O_2$

Figure 18:
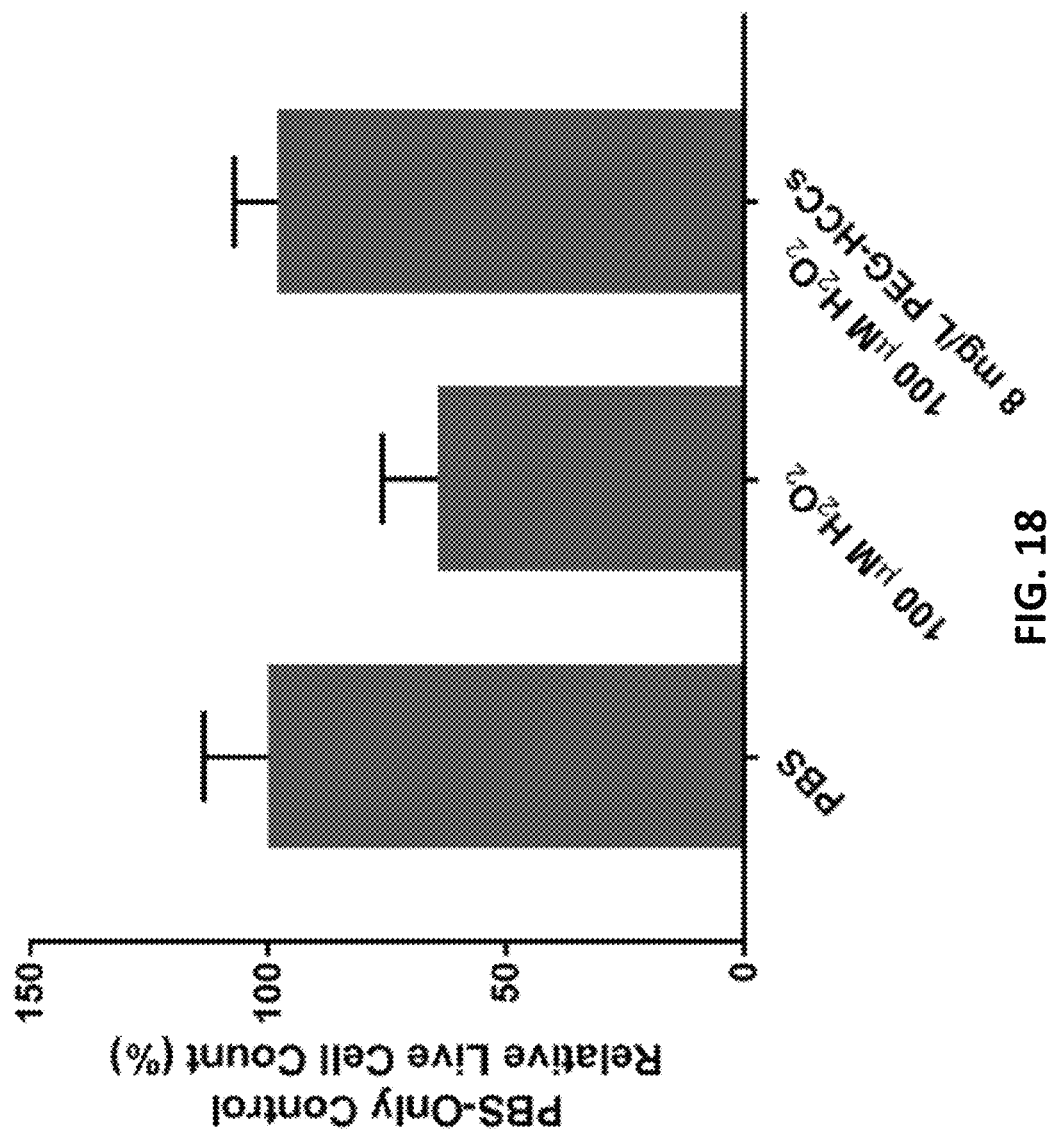
FIG. 18 is a graph of cell viability following addition of hydrogen peroxide to cultured brain endothelial cells (b.End3).

The protection of PEG-HCCs against hydrogen peroxide was measured in both cultured murine cortical endothelial bEnd0.3 cells and in cultured primary murine cortical E17 neurons. It was observed that 100 µM $H_2O_2$ reduced cell viability in bEnd0.3 cells at 24 hours by approximately 50% as indicated by a Live/Dead assay, as shown in FIG. 18. In this FIG. 18, live cell counts (Live/Dead cell viability assay) per well is presented on y-axis as mean and SD of replicates. 100 µM $H_2O_2$ was added and 15 min later either media or hydrophilic carbon clusters, conjugated to poly(ethylene glycol) (PEG-HCCs) (8 mg/mL) was added and live cell/well assessed the following day. $H_2O_2$ reduced cell viability by 50%, which was completely restored by PEG-HCCs.

Figure 19:
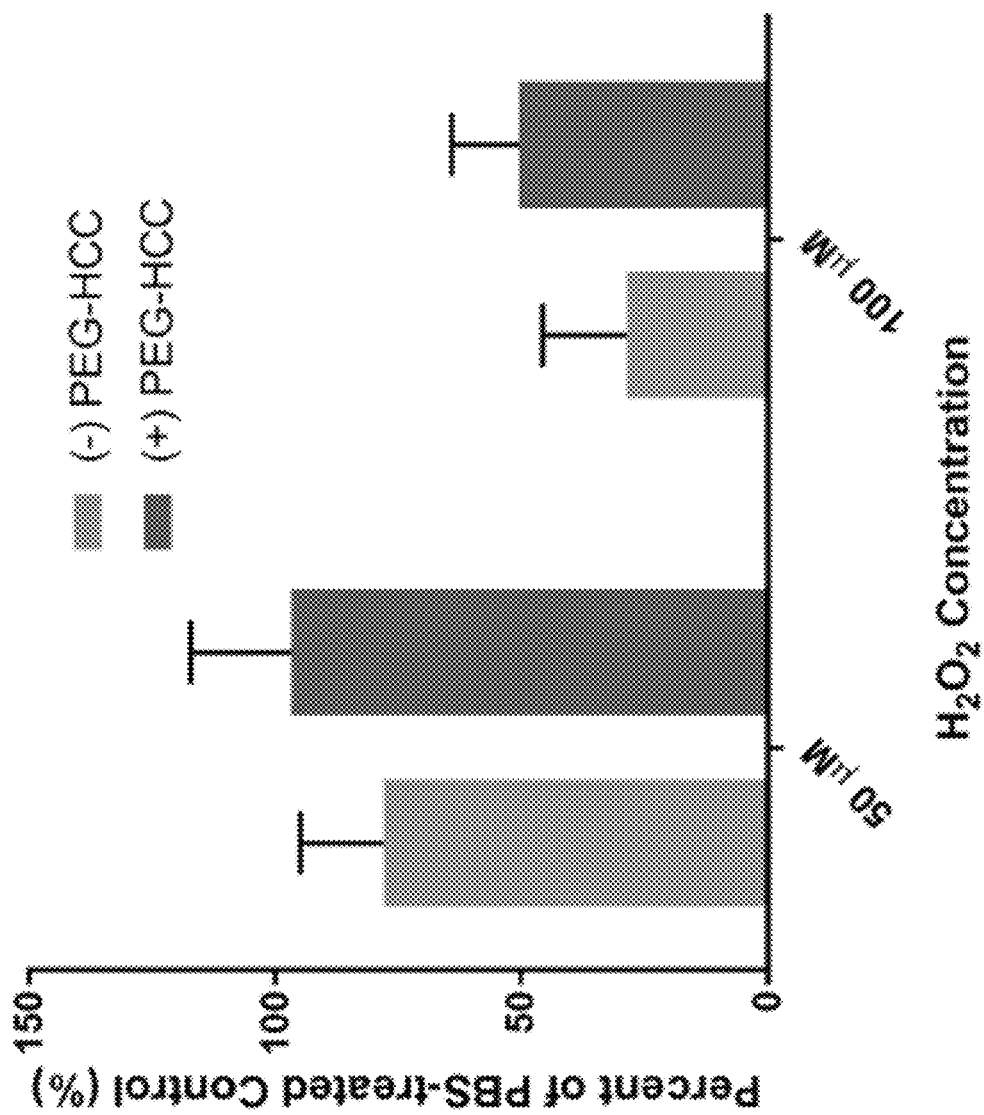
FIG. 19 is a graph of hydrophilic carbon clusters, conjugated to poly(ethylene glycol) (PEG-HCCs) reduce cytotoxicity of $H_2O_2$ on treated murine cortical neurons (MCNs).

The addition of PEG-HCCs after 15 minutes restored cell number to baseline (p<0.001 vs $H_2O_2$). In E17 neurons, it was found that 100 µM $H_2O_2$ was more lethal in neurons than b.End3 cells, nevertheless, partial restoration was achieved with posttreatment with PEG-HCCs. See FIG. 19. In FIG. 19, PEG-HCCs are given at a concentration of 8 mg/L treated immediately following exposure and overnight incubation reduce cell death restored cell number to baseline following 50 µM $H_2O_2$ and doubled cell count following the much more toxic 100 µM.

Cerebral Blood Flow

Figure 20A:
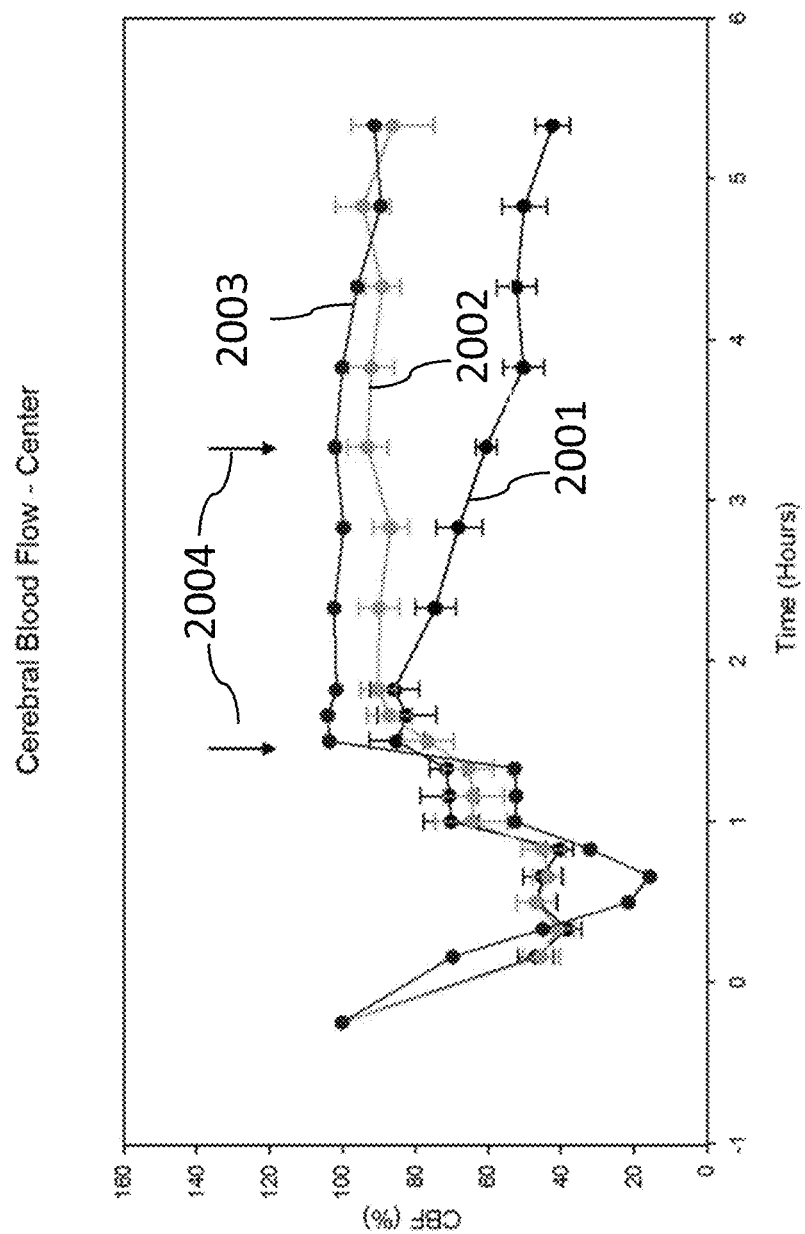
FIGS. 20A-20B are graphs showing the cerebral blood flow (%) over time for two treatments following a protocol. Lines 2001 and 2005 represent the effect of the negative vehicle control (PBS) on cerebral blood flow. Lines 2002 and 2006 represent the effect of PEG-HCCs on cerebral blood flow. Lines 2003 and 2007 represent the effect of PEG-GQDs on cerebral blood flow. Arrows 2004 and 2008 represent the period of time between injections of vehicle, PEG-HCCs, or PEG-GQDs.
Figure 20B:
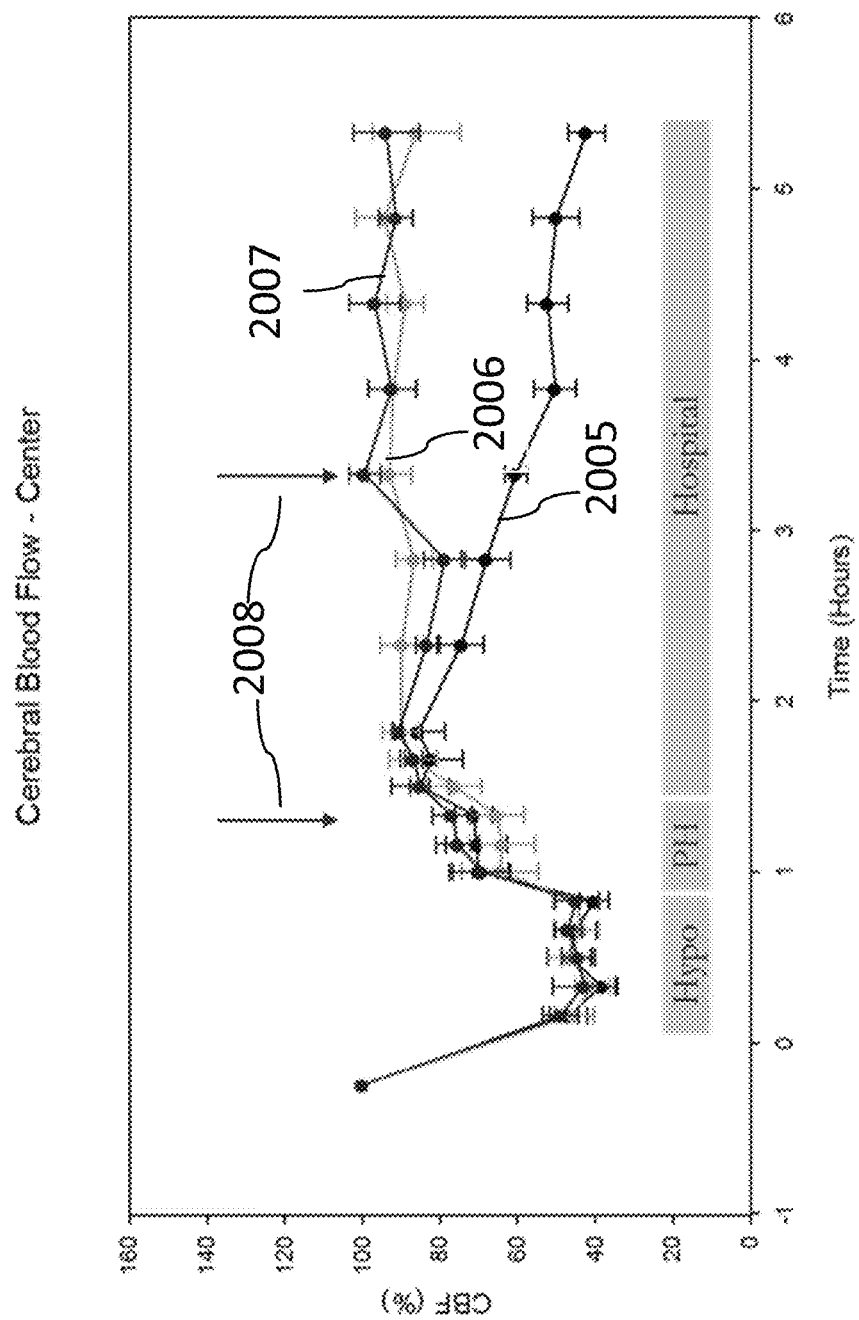

A protocol was followed as follows (a) 50 minutes of hypotensive/hemorrhagic shock phase, (b) 30 minutes of lactate ringers (resuscitative phase), and, finally (c) the definitive hospital period. Dosages were administered under this protocol at 80 minutes and 200 minutes post mild TBI impact injury. FIGS. 20A-20B are graphs showing the cerebral blood flow (%) over time for two respective treatments following the protocol.

In FIG. 20A, curves 2001-2003 are for PBS (n=10), PEG-HCC (n=10), and PEG-GQD (n=1), respectively. In the treatment reflected in FIG. 20A, the one animal treated with PEG-GQDs demonstrated a return and recovery to baseline levels of cerebral blood flow perfusion (when compared to PBS treated animals). Arrows 2004 indicate the two administration times that PEG-GQD was given to the animals (first dose at 80 minutes and second dose at 200 minutes). The dosage was 4 mg/kg for the first dose (at 80 minutes) and 2 mg/kg for the second dose (at 200 minutes). The one animal that received the PEG-QGD showed even greater recovery than the other animals treated with PBS or PEG-HCC.

In FIG. 20B, curves 2005-2007 are for PBS (n=10), PEG-HCC (n=10), and PEG-GQD, (n=6), respectively. In the treatment reflected in FIG. 20B, six animals were treated with PEG-GQD. Arrows 2008 indicate the two administration times that PEG-GQD was given to the rat (again, first dose at 80 minutes and second dose at 200 minutes). The dosage was 2 mg/kg for both dosages. The six animals that received the PEG-GQD showed that they restore cerebral blood flow perfusion to that equal of animals treated with PEG-HCC.

Variations

Metal toxicity is involved in a variety of pathologies throughout the body and its major deleterious action is through stimulation of excessive oxidative radicals. However, the use of chelators is hampered by poor cellular or tissue penetration, large therapeutic doses and short half-lives. After administration into the body, either intravenously or some other route, the novel formulation of the present invention combines an avid cellular uptake delivering the chelator to the important site of action as well as addressing oxidative injury through the combined action of the parent nanomaterial. Additional targeting to either specific tissues or subcellular organelles such as mitochondrial will be employed to differentiate the utility in these different conditions. When used in ischemic injury, the nanoparticles convert $O_2^-$ to $O_2$, making them superoxide to oxygen generators (SOGs). This behavior can be very helpful in the treatment of ischemic tissue where $O_2^-$ overwhelms the body's natural antioxidant defense systems. See Samuel 2015.

The formulation of the present invention can be a novel approach to a variety of acute and chronic injuries, many of which involve excess free metals. Examples include the increased binding of iron and copper to hyperphosphorylated proteins such as tau in Alzheimer Disease.

Systemic shock involves an oxidative reaction especially during resuscitation that could be mitigated by a combination drug available outside of the hospital setting. This preparation has been shown to reduce the breakdown of the deferoxamine and so increase shelf life and its potential utility in new settings not currently feasible.

There is no precedence in the existing literature for combining chelation with antioxidant and intracellular effectiveness of the nanoparticles as described and taught herein. There are formulations of chelators that have been used to enhance cellular uptake, such as attaching polymers to enhance brain uptake as well as molecules that have enhanced cellular uptake intrinsically, but none of these variations address the oxidative reaction, nor do these formulations address potential toxicity from the chelators, which can be mitigated by addressing both the presence of the metal and its deleterious actions through the combination of antioxidant nanomaterial and chelator in a single molecule acting at the responsible site of action. There are several tremendous advantages of the present invention over conventional methods of chelation. First, cellular uptake is enhanced that smaller doses of chelator are effective, thus minimizing the need for high blood levels of chelators, which have deleterious effects such as hepatotoxicity. In particular. DEF, administered intravenously by itself, has to be used in very large doses (50 mg/kg) and has a short half-life in circulation ($t_{1/2} \approx 0.3$ h) which can result in undesired toxicity. Second, this novel combination demonstrates enhanced shelf life, one of the major limitations of DEF. Third, the present invention can demonstrate that cellular uptake results in localization of the DEF-PEG-HCC to critical structures such as mitochondrial membranes. Also, given the crucial role of Fe in catalyzing oxidative stress, the co-localization of the chelator and the intrinsic antioxidant ability of the HCC demonstrates better cellular protection than either alone. Other advantages of combining a chelator with the carbon nanomaterial backbone include the ability to target specific therapeutic moieties that expands the use of the material to a large number of conditions in which both oxidative stress and heavy metals contribute to the deleterious outcomes.

A variety of chelators can be utilized in the present invention. There are certain advantages of using deferoxamine, particularly since only one deferoxamine is needed per metal ion, and others are available that could preferentially target other metals through differential chelating abilities for different metals.

In addition to deferoxamine as a chelator and iron as the target, multiple other chelators that have affinity to a variety of metals and ions are feasible with the present invention. For example, metals such as lead and mercury can be ingested by humans and animals from contaminated environment. The metal copper can be toxic when in excess in the body due a condition such as Wilson's Disease. Many of these toxicities share in common the generation of reactive species that in turn damage membranes, DNA, mitochondria and other vital cellular structures. These toxicities must currently be treated by approaches requiring the oral, ip or intravenous administration of large doses of various chelating agents such as ethylenediaminetetraacetic acid (EDTA) and d-penicillamine. Often large doses of many of these agents are necessary because of poor or inconsistent intracellular uptake. A new approach that promotes cellular uptake while addressing key mechanisms of injury is a major advance.

The present invention describes the conjugation of chelators, such as EDTA, with a parent carbon nanomaterials. This novel approach has the distinct and unique advantages of promoting intracellular transport to the necessary site of action due to the rapid uptake of the PEG-HCC or PEG-GQD, permitting use of a lower total dose (hence less systemic toxicity), while simultaneously supporting the critical mitochondrial functions of electron transport and quenching of oxidative radicals due to the electron transport shuttle properties of the carbon nanomaterial as well as its antioxidant. The unique action of this construct at the crucial cellular sites of action makes this an entirely novel approach to address multiple important facets of metal toxicity. And each of these chelators can be used in much lower dosages than normally used since the carbon particles deliver them to the mitochondrial sites of interest.

Examples of structures of representative chelators bound to nanomaterials are illustrated in FIG. 21.

TABLE 3 provides a list of reported clinically useful chelators for different metal toxicities. See also Wax, P. "Current Use Of Chelation in American Health Care," *J. Med. Toxicol.* 2013, 9:303-307.

TABLE 3

| Metal Toxicities | Chelators |
|---|---|
| aluminum | deferoxamine |
| americium | pentetic acid (DTPA) |
| arsenic | dimercaprol (British anti-Lewisite (BAL)) |
| | succimer (dimercaptosuccinic acid (DMSA)) |
| | unithiol (2,3-dimercaptopropane-1-sulfonate (DMPS)) (*Not for use in USA*) |
| cadmium | None have been shown to be effective in humans |
| cesium | Prussian blue |
| chromium | None have been shown to be effective in humans |
| copper | D-penicillamine |
| | trientine |
| curium | pentetic acid (DTPA) |
| iron | deferasirox |
| | deferiprone |
| | deferoxamine |
| lead | calcium disodium edetate |
| | dimercaprol |
| | D-penicillamine |
| | ethylenediaminetetraacetic acid (EDTA) |
| | succimer (dimercaptosuccinic acid (DMSA)) |
| mercury | dimercaprol (British anti-Lewisite (BAL)) |
| | D-penicillamine |
| | ethylenediaminetetraacetic acid (EDTA) |
| | succimer (dimercaptosuccinic acid (DMSA)) |
| | unithiol (2,3-dimercaptopropane-1-sulfonate (DMPS)) (*Not for use in USA*) |
| plutonium | pentetic acid (DTPA) |
| thallium | Prussian blue |
| uranium | pentetic acid (DTPA) |
| | hydroxypyridonates |
| zinc | calcium disodium edetate |
| | tetrathiomolybdate |

Such chelators can be used in embodiments of the present invention.

In some embodiments, the ratio of PEG:chelator (such as PEG:DEF) is in the range of 1:3 and 3:1, and generally is below 1:1.

Graphenic Materials for the Treatment of Acute and Chronic Mitochondrial Electron Transport Chain Dysfunction Proton-coupled electron transport is crucial to oxidative phosphorylation (OXPHOS), and a variety of disorders involve disruption in that function. In many forms of mitochondrial injury, electron transport is disrupted and triggers the generation of free radicals including superoxide anion ($O_2$—·) and hydroxyl radical (·OH), depleting endogenous antioxidants leading to cellular injury and ultimately cell death. It has been discovered that synthesized graphenic materials can protect against acute mitochondrial injury including cyanide poisoning and arsenic poisoning. This includes mechanistic evidence that these materials can serve as an alternative pathway for electron transport, or bypass, in the electron transport chain following inhibition of Flavin-containing mitochondrial complexes (Complex I and III) thus minimizing the formation of reactive oxygen species (ROS) and/or reactive nitrogen species (RNS).

Importantly, these materials are weakly active with endogenous reducing agents in the mitochondria, however, upon cellular injury, they can utilize the resulting superoxide as an electron-rich source to not only convert superoxide to hydrogen peroxide but also transport electrons to higher potential oxidizers such as cytochrome C. A purpose of the present invention is not to replace faulty mitochondrial complexes but to provide an alternative route, or bypass for electrons released by Flavin-containing electron transport chain members.

Graphenic materials can treat acute or chronic mitochondrial disorders that involve disruption of electron transport alone or as part of a combinational therapy. These materials provide an alternative route for electron transport and simultaneously maintain crucial mitochondrial functions via their superior antioxidant properties and quenching of reactive oxygen species and/or reactive nitrogen species.

The present invention relates to the use of graphenic materials, prototyped as poly(ethylene glycol)-functionalized hydrophilic carbon clusters (PEG-HCCs), in the treatment of electron transport disruption epitomized by acute cyanide poisoning (and by arsenic poisoning). It is believed that these properties will apply to graphenic structured materials regardless of size, but will likely depend on functional groups that interact with mitochondrial structures and electrons. Data is shown regarding the activity of a prototypical graphenic material, poly(ethylene glycol)-functionalized-hydrophilic carbon clusters (PEG-HCCs) [Tour et al., U.S. Pat. No. 9,572,834, entitled "Use of carbon nanomaterials with antioxidant properties to treat oxidative stress," issued Feb. 21, 2017 ("Tour '834 Patent")] that has previously been shown to be high capacity, catalytic superoxide dismutase (SOD) mimetics and are nearly as effective at quenching hydroxyl radical. The Tour '834 Patent is incorporated by reference herein in its entirety. See also Samuel 2015 (showing mechanism of SO dismutation using PEG-HCCs).

PEG-HCCs reduce reperfusion injury in animal models of traumatic brain injury. Here, it is demonstrated that they can transfer electrons both from superoxide ($O_2^-$) and reduced nicotinamide dinucleotide(phosphate) (NADPH) to higher reduction potential species such as resazurin, or cytochrome C.

In the electron transport chain (ETC), several constituents are known to promote the generation of superoxide through 'electron leakage' via the generation of ROS. For instance, at Complex I, flavin mononucleotide is reduced by NADPH through a two-electron reduction to form $FMNH_2$ at the $I_F$ binding site. Under normal conditions, ubiquinone binds to the $I_Q$ binding site near the mitochondrial inner membrane (MIM) and undergoes two single-electron reductions performed by the N2 $Fe_2S_4$ iron sulfur cluster at the end of a seven-member chain with electrons donated by $FMNH_2$ (FIG. 22A). FIG. 22A illustrates Complex I under physiological conditions. Electrons are transferred from reduced nicotinamide adenine dinucleotide phosphate (NADPH) to flavin mononucleotide (FMN) and up an iron-sulfur bridge to the Complex I quinone binding site ($I_Q$) site where electrons are donated to ubiquinone.

Pathological conditions typically are manifest either as a blockade of the $I_Q$ site by an inhibitor such as rotenone (FIG. 22C), or by a downstream blockade in later mitochondrial complexes leading to an overabundance of reduced electron shuttle species such as ferrocytochrome C, ubiquinol, reduced flavin mononucleotide ($FMNH_2$) or reduced flavin adenine dinucleotide ($FADH_2$). A third possibility is the oxidation of the $Fe_2S_4$ clusters by superoxide or hydroxyl radical. FIG. 22C illustrates inhibitors, such as rotenone, can block the $I_Q$ site leading to an accumulation of $FMNH_2$ and the generation of reactive oxygen species (ROS). These types of mitochondrial injuries also cause a reduction in mitochondrial membrane potential and ATP synthesis by the loss of proton transfer into the intermembrane space.

FIG. 22B illustrates oxidation of the iron-sulfur chain leads to a blockade that causes reduced flavin mononucleotide ($FMNH_2$) to remain at the Complex I flavin site ($I_F$) longer than normal and leads to the generation of ROS. With the loss of $Fe_2S_4$ chain continuity, electrons are unable to migrate from the $I_F$ site to the $I_Q$ site leading to an overly-reduced state at the $I_F$ site (FIG. 22B). In the instance of an $I_Q$ blockade, reduced $FMNH_2$ can perform single-electron reductions of dioxygen to form superoxide.

The role of Complex III in ROS generation is also important as ROS can be generated on both sides of the mitochondrial inner membrane and possibly from both quinone sites if the correct inhibitor is utilized (FIGS. 22D-22F). FIG. 22D illustrates that, under normal conditions, ubiquinol reduces ubiquinone via two cytochrome iron complexes in Complex III, and protons are transported across the mitochondrial inner membrane. FIG. 22E illustrates blocking the higher potential quinone site with an inhibitor causes the formation of ROS on both sides of the mitochondrial inner membrane. FIG. 22F illustrates Inhibition of the cytochrome C site can lead to electron leakage from the lower potential quinone site.

Figure 23A:
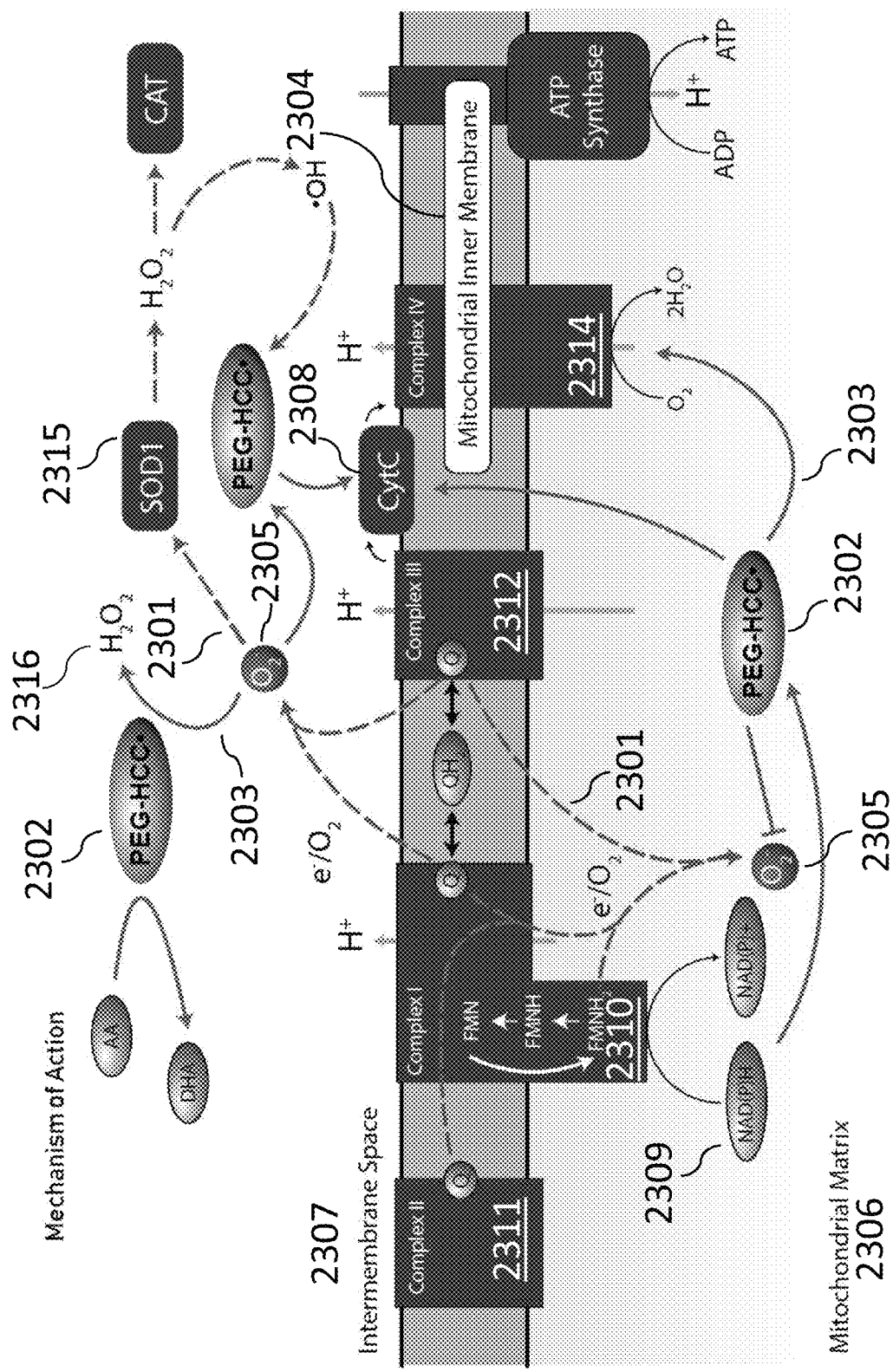
FIGS. 23A-23C illustrate the roles of PEG-HCC in the electron transport chain as an electron shuttle and superoxide dismutase mimetic.
Figure 23B:
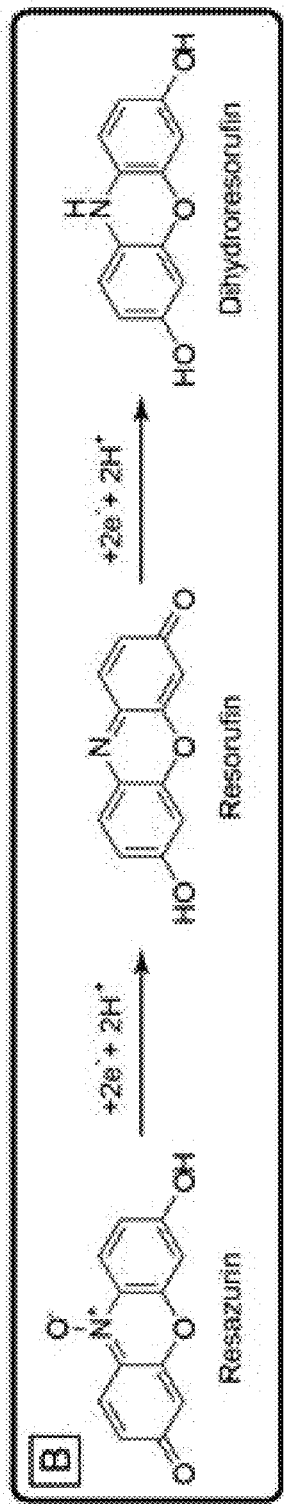
Figure 23C:
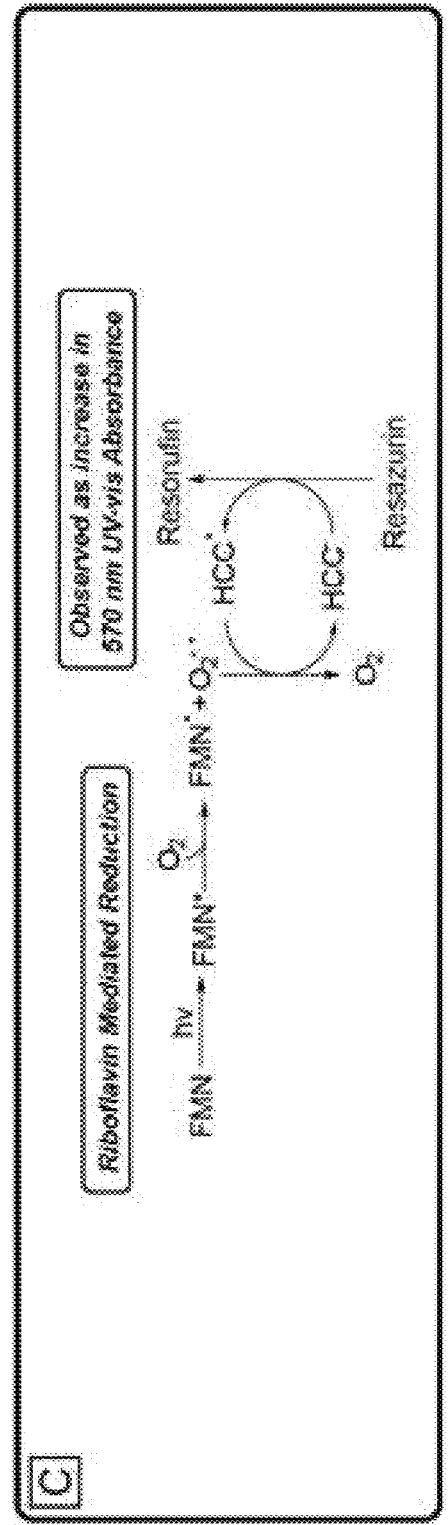

To model flavin-mediated superoxide generation and to demonstrate how PEG-HCCs may be able to circumvent such scenario, the photoexcitation of riboflavin to generate superoxide in a cell-free setting was utilized (FIG. 23C). As shown in FIG. 23C, FMN generates superoxide when photoexcited, PEG-HCCs can then potentially transfer the electron from superoxide to resazurin through an unknown process to generate resorufin. NADPH can also be used to generate resorufin from resazurin and is expected to involve a two-step reaction like that of FMN.

Excitation of flavin mononucleotide (riboflavin-5'-phosphate, FMN) with a 460 nm light source (in this case, a light emitting diode array) generates both singlet oxygen and superoxide as a result. It was observed that photoexcited riboflavin, in the presence of hydrophilic carbon clusters can reduce resazurin to resorufin as evidenced by the change in the absorbance at 570 nm by UV-vis.

Figure 24:
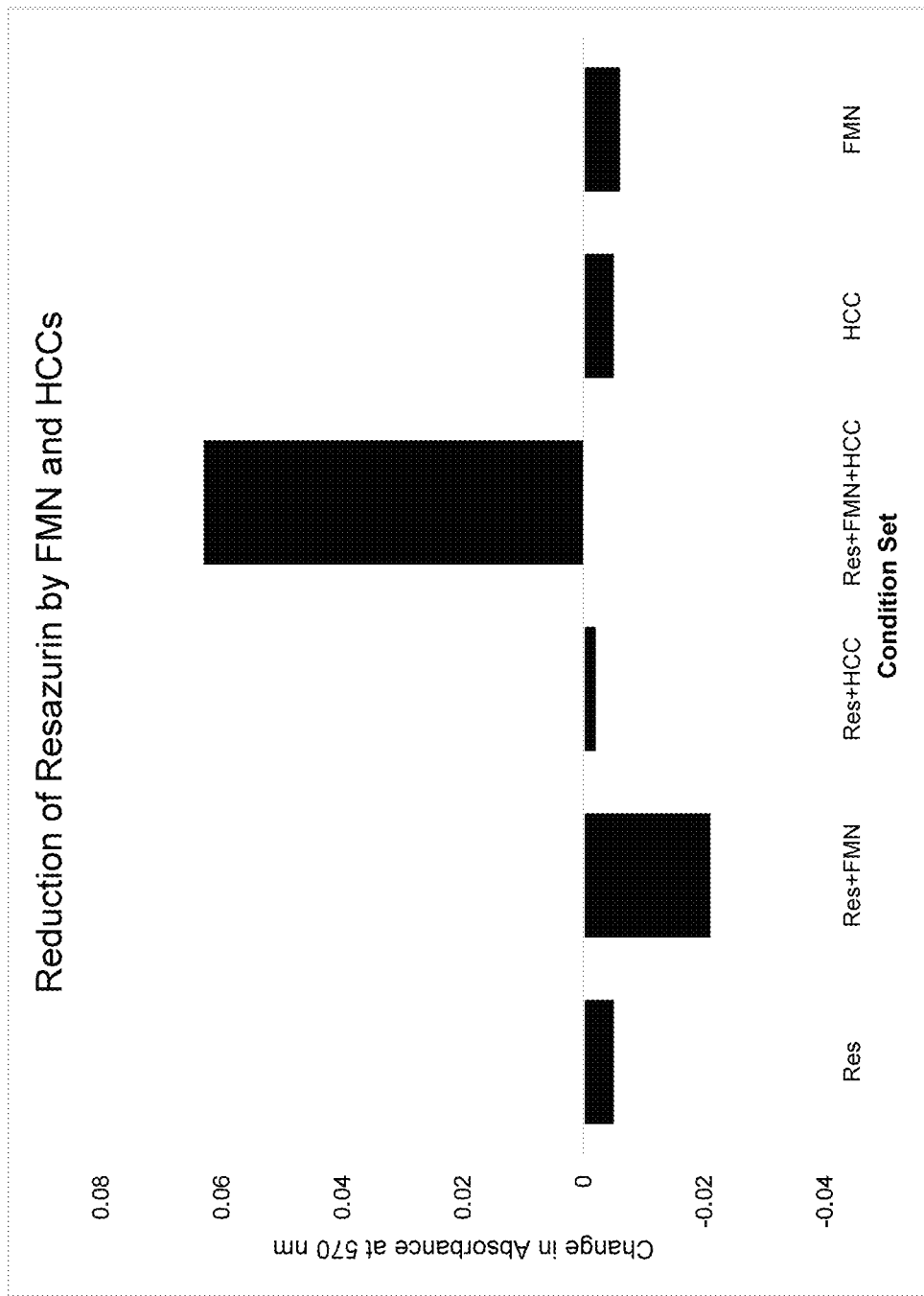
FIG. 24 is a graph showing effect of 10-minute exposure to 460 nm light on solutions containing resazurin, PEG-HCCs and riboflavin-5'-phosphate (shown as HCC in the figure).

As shown in FIG. 24, solutions containing hydrophilic carbon clusters, FMN, and resazurin undergo a shift in absorbance at 570 nm indicative of the formation of resorufin. Only in solutions containing PEG-HCCs (shown as HCC in the figure) is resazurin reduced to resorufin as shown by an increase in the absorbance measured at 570 nm. Resazurin may be reduced to dihydroresorufin directly by FMN, however no spectroscopic evidence presently exists. Without PEG-HCCs, the FMN appears to transform the resazurin into a colorless species, possibility dihydroresorufin (FIG. 23B) or a peroxo-compound. FIG. 23B: Structures and reduction reactions of resazurin and resorufin, the species utilized in model experiments.

It is believed that superoxide can donate electrons to the PEG-HCC and in turn, the reduced PEG-HCC transfers those electrons to resazurin leading to the formation of reduced resorufin (structures shown in FIG. 23B). The bases for the rationale regarding this process includes two key experiments/observations. First, it was observed that PEG-HCCs can reduce resazurin to resorufin in the presence of photoexcited FMN (FIG. 24).

Figure 25:
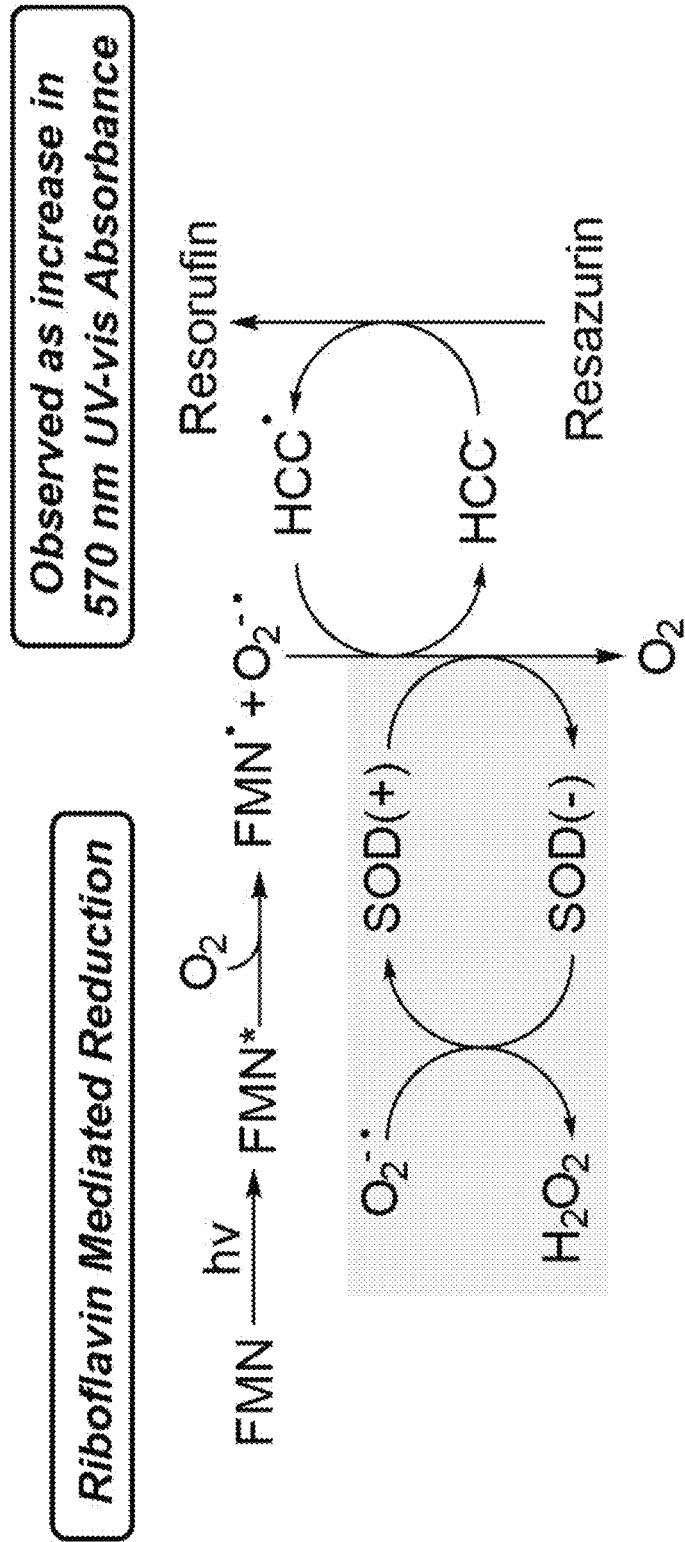
FIG. 25 is a schematic of a competition experiment between PEG-HCCs (shown as HCC in the figure) and SOD.

Next, a competition experiment was performed between PEG-HCCs and superoxide dismutase (SOD) as shown in FIG. 25. FIG. 25 is a schematic of a competition experiment between PEG-HCCs (shown as HCC in the figure) and SOD. SOD competes with PEG-HCCs for superoxide. Reducing the available supply of superoxide leads to a reduced rate of resazurin reduction. Because SOD does not have a binding pocket for resazurin, SO is converted to $H_2O_2$ instead of donating electrons to the PEG-HCCs and onward to resazurin. In the experiment of FIG. 25, superoxide dismutase and hydrophilic carbon clusters were resident in a solution with resazurin and FMN. SOD does not have the proper binding site for quinones or quinone-like species and thus, resazurin should not be able to participate in the SOD dismutation cycle.

Figure 26:
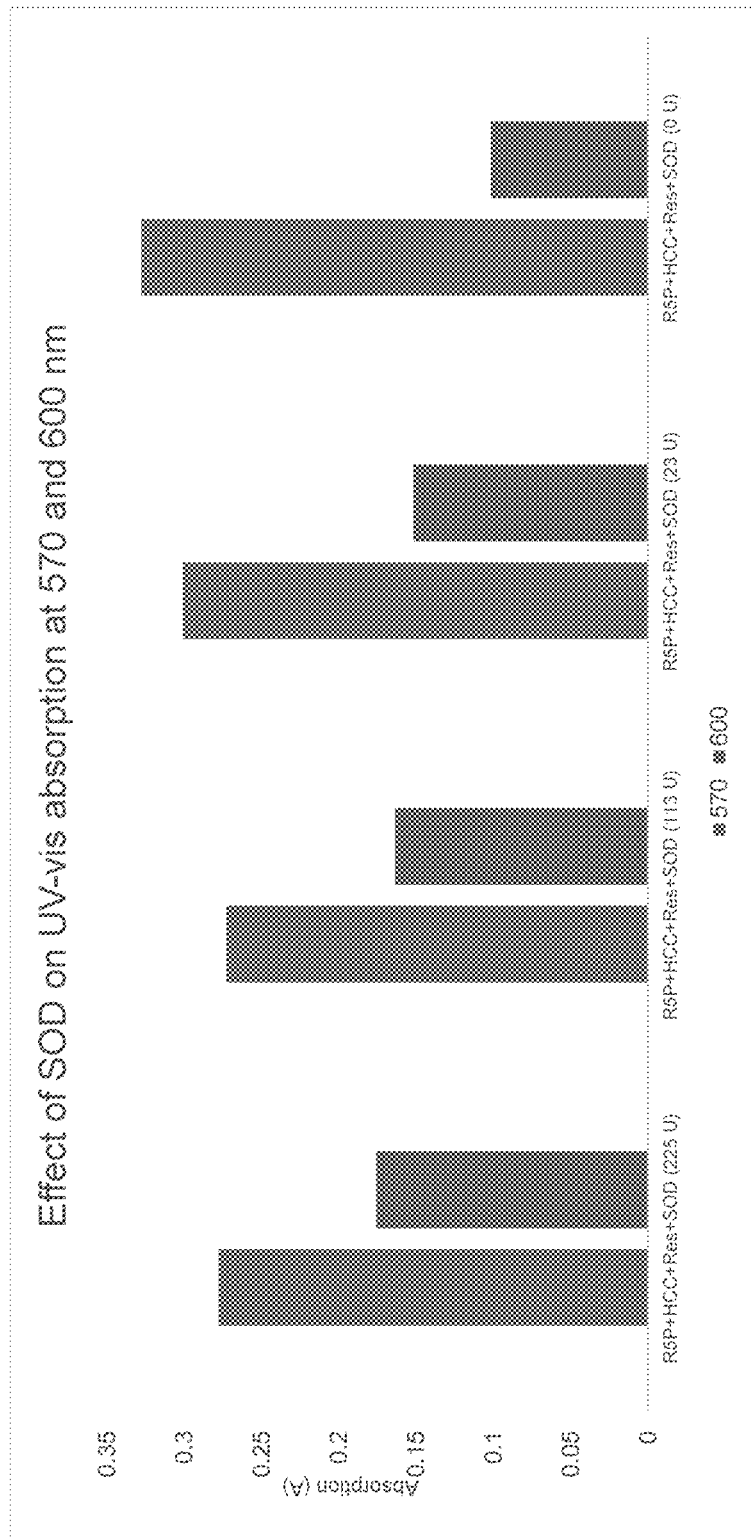
FIG. 26 is a graph showing addition of superoxide dismutase to solutions containing PEG-HCCs (shown as HCC in the figure), resazurin, and FMN.

Because both SOD and PEG-HCCs can dismutate SO into dioxygen and hydrogen peroxide, but only PEG-HCCs can reduce resazurin to resorufin, by adding SOD to the reaction mixture, the rate of resazurin reduction would be lower because there are more SO-dismutating catalyst (SOD and PEG-HCCs) but the same amount of superoxide being generated by FMN. Thus, the concentration of superoxide available for PEG-HCCs to use as an electron source is lower, and the reduction of resazurin to resorufin is slower (FIG. 26). FIG. 26 shows that the addition of superoxide dismutase to solutions containing PEG-HCCs (shown as HCCs in the plot), resazurin, and FMN reduces the absorption at 570 nm and proportionally increases the absorption from oxidized resazurin at 600 nm following exposure to 460 nm light for 10 minutes. The amount of unreacted resazurin increases directly with the concentration of SOD.

It has also been shown that ferricytochrome C can be reduced at a faster rate with PEG-HCCs at low concentration (4 mg/L) than without PEG-HCCs. Ferricytochrome C ($Fe^{3+}$) has a reduction potential of +250 mV and can undergo a single electron reduction to form ferrocytochrome C ($Fe^{2+}$). Ferrocytochrome C donates its electron to Complex IV and acts as a shuttle to transport electrons as they come off Complex III (FIG. 22A). It has been found that while superoxide can reduce cytochrome C, the addition of PEG-HCCs cause this reaction to work faster.

Figure 27:
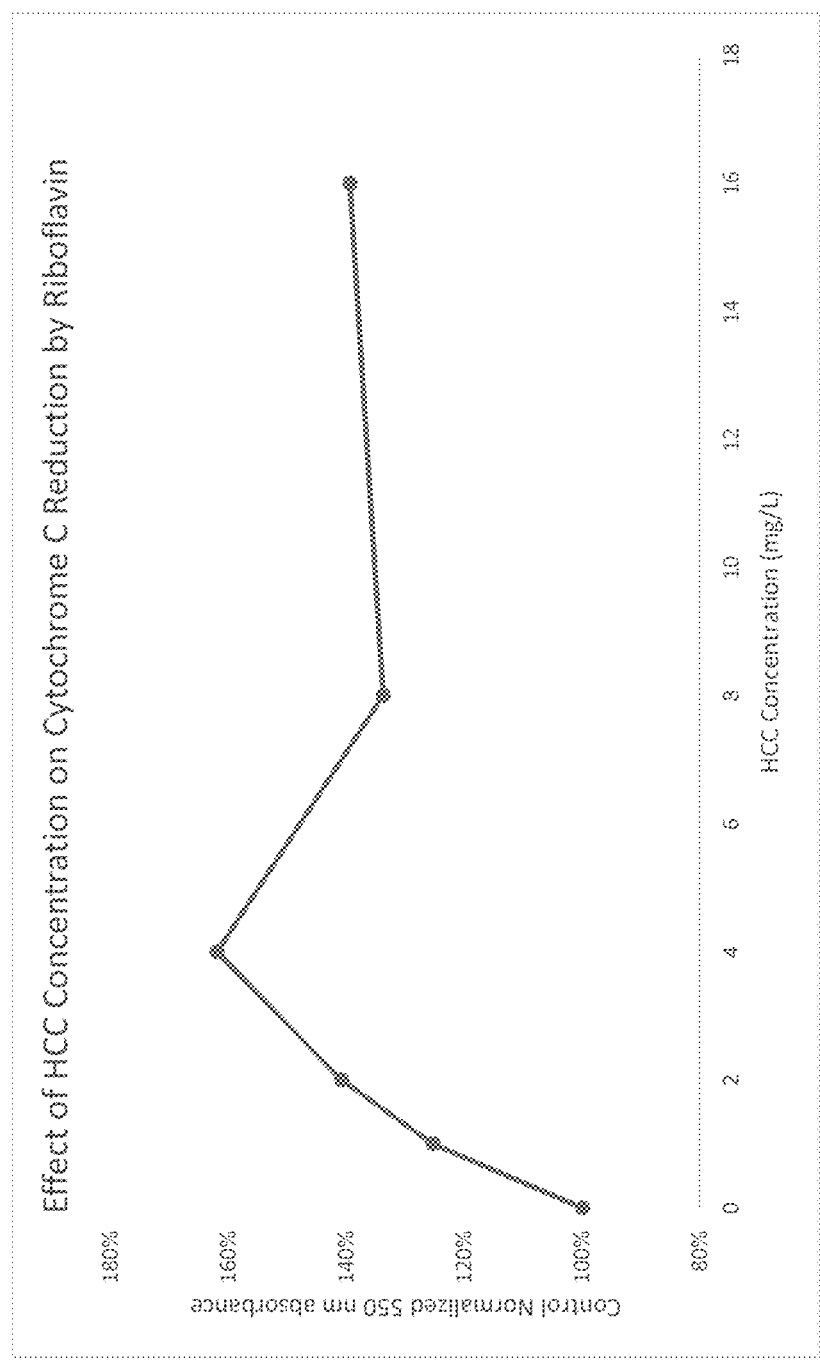
FIG. 27 is a graph showing the effect of PEG-HCC (shown as HCC in the figure) concentration on of cytochrome C reduction by riboflavin.

However, it has also been found that this effect is concentration dependent and at concentrations greater than 4 mg/L, the acceleration effect is less pronounced (FIG. 27). FIG. 27 shows that FMN reduces cytochrome C under exposure of light via the generation of superoxide. The rate of cytochrome C reduction is dependent on the concentration of PEG-HCCs (shown as HCC in the figure) present in solution. A rate maximum repeatedly appears at 4 mg/L with the rate being slower at either higher or lower concentrations.

It is believed that below a certain concentration, PEG-HCCs are not as efficient SOD mimetics as they are electron shuttles. However, because the PEG-HCCs absorb light, they can reduce the amount of light that excites the riboflavin in solution thus giving the appearance of a lower rate. At lower concentrations, this effect is clearly not dominant, however at concentrations greater than 4 mg/L, this effect may become more important and will require further investigation. This finding shows that electrons can be shuttled between superoxide generated by FMN in Complex I or the semiubiquinone at Complex I, II, or III to ferricytochrome C (FIG. 22A).

Figure 28:
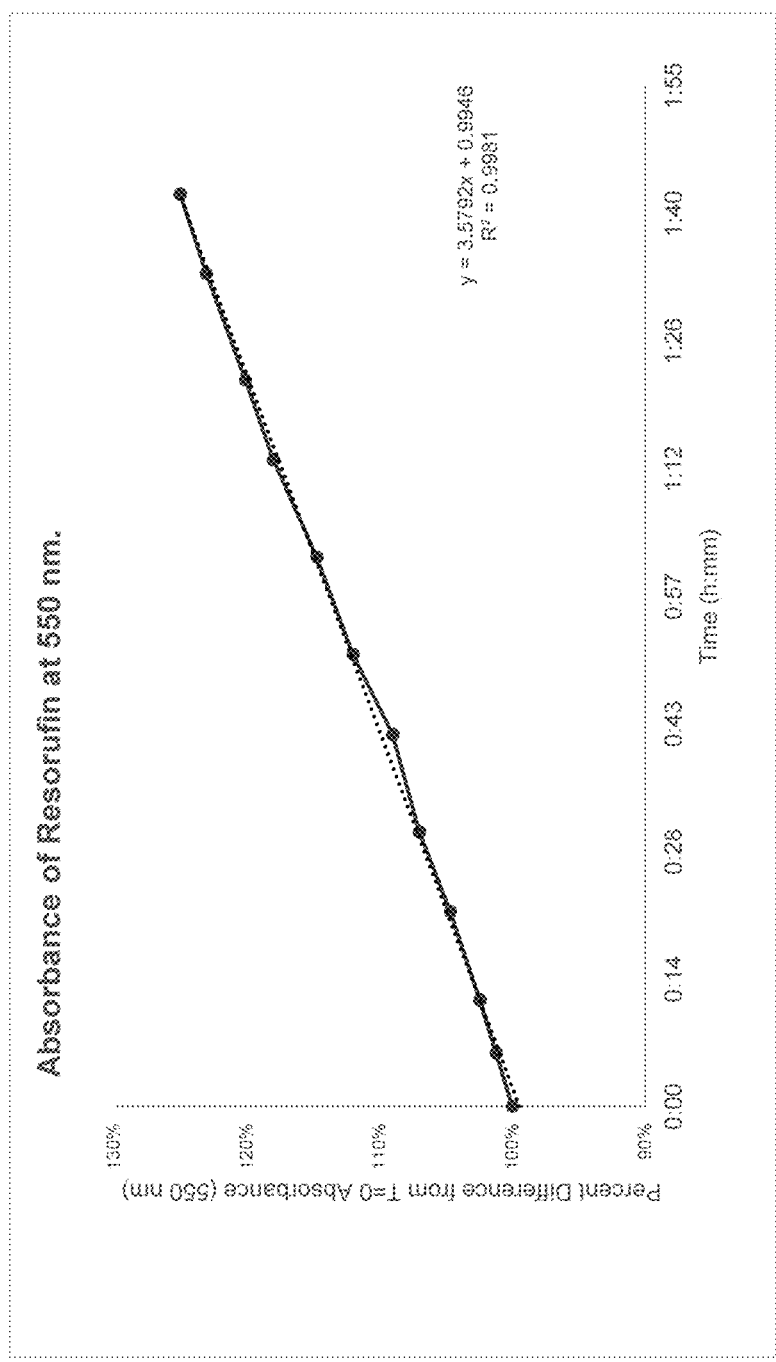
FIG. 28 is a graph showing reduction of resazurin to resorufin is shown as an increase in the absorption of light at 550 nm. In this experiment, the intensity of the 550 nm absorption was tracked in the sample containing PEG-HCC, resazurin and NADPH and compared later time points to the original to obtain a percent difference.

In addition to using superoxide as an electron source, it has been demonstrated that PEG-HCCs can reduce resazurin using NADPH. This effect roughly models the NADPH-iron-sulfur cluster pathway in Complex I with hydrophilic carbon clusters by using NADPH as the reducing agent and resazurin as the final electron acceptor instead of ubiquinone as shown in FIG. 28.

In this second model, electrons are donated to the hydrophilic carbon cluster, possibly by a single electron followed by a hydrogen atom (H·) and then reduce resazurin through two single-electron reductions to form resorufin as a second step. It is believed that PEG-HCCs may be able to take the role of the $FMNH_2$—$Fe_2S_4$ portion of the Complex I transfer chain by reducing ubiquinone along the MIM with mitochondrial NADPH directly instead of going through a flavin or $Fe_2S_4$ chain.

Figure 29:
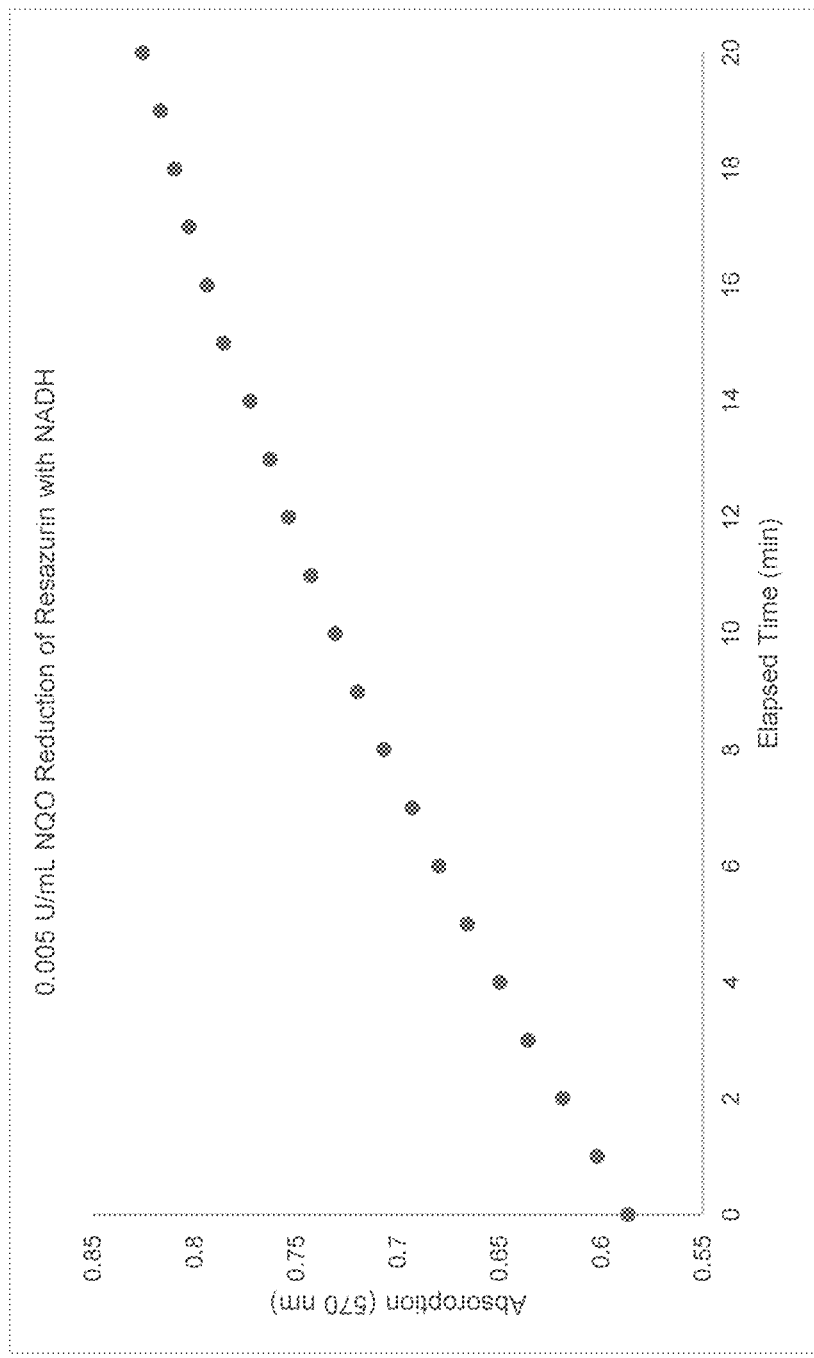
FIG. 29 is a graph showing change in UV-vis absorbance as a function of time with a constant concentration of NADPH-quinone oxidoreductase (NQO) and NADPH.

The reduction rate of resazurin by NQO appears to be much faster than HCCs (FIG. 29). FIG. 29 shows change in UV-vis absorbance as a function of time with a constant concentration of NADPH-quinone oxidoreductase (NQO) (0.005 U/mL) and NADPH ($5.0 \times 10^{-4}$ M). The increase in absorption at 570 nm is due to an increase in the concentration of resorufin. Because NQO has a quinone-binding pocket, it appears that resazurin binds to the pocket and undergoes reduction at that site. Unlike NQO or Complex I, hydrophilic carbon clusters are unable to reduce ubiquinone-1 to ubiquinol in the presence of NADH or NADPH. It is believed that this is due to an energetic barrier caused by the similarity of the reduction potentials of PEG-HCCs and ubiquinone. A larger reduction potential may be necessary for this reaction to occur and does explain the spontaneous reduction of resazurin. However, a slow oxidation of NADPH and NADH may be beneficial as it does not deplete mitochondria of their endogenous NADPH supply which is typically necessary to reduce oxidized antioxidants such as glutathione disulfide.

In the instance of oxidative damage to the mitochondria, the iron in the $Fe_2S_4$ clusters in Complex I, Complex III, and aconitase can be oxidized from $Fe^{2+}$ to $Fe^{3+}$ thus rendering them incapable of performing their task of shuttling electrons through the enzymes. Hydrophilic carbon clusters appear to be able to bypass the loss of these FeS chains by performing the necessary electron transfer outside the complexes. As has been demonstrated, electrons can be donated from FMN-generated superoxide to cytochrome C, and from NADPH at Complex I. In summary, hydrophilic carbon clusters may be able to serve as a bypass mechanism for electron leakage by using either NADPH, or flavin-generated superoxide as an electron source.

Chemical Mechanism of Action of PEG-HCCs on Resazurin

The initial mechanistic was focused on the reduction potential of the reducing agent; however, the reduction of resazurin by ethanol (ethanol→acetylaldehyde $E_0$=−197 mV; $\Delta E_0$=+183 mV) has also been tested with and without PEG-HCCs and it was found that reduction does not occur at 25° C. despite having a positive $\Delta E_0$. The oxidation of ethanol is through a two-electron process as opposed to two successive single-electron oxidations.

While NADH and NADPH are not typically considered to perform single-electron reductions, a small body of literature suggests that this is not always the case. As reviewed by Gebicki et al., multiple oxidation mechanisms exist for NADH including a single-step hydride transfer, a two-step electron-hydrogen atom transfer, and a three-step electron-proton-electron transfer. [Gebicki, J., et al., "Transient Species in the Stepwise Interconversion of NADH and NAD+," *Acc. Chem. Res.* 2004, 37, 379-386]. Single-electron oxidations of NADPH are rare but not unheard of, for instance NADPH was shown by Almarsson et al. to perform an electron-proton-electron reduction of Compound II in catalase. [Almarsson, O. et al., "Mechanism of One-Electron Oxidation of NAD(P)H and Function of NADPH Bound to Catalase," *J. Am. Chem. Soc.* 1993, 115, 7093-7102]. Grodkowski et al. showed that several organic radicals were reduced with rate constants between $10^4$-$10^5$ by NADH through single-electron reductions. [Grodkowskl, J. et al., "One-Electron Transfer Reactions of the Couple NAD/NADH," *J. Phys. Chem.* 1983, 87, 3135-3138]. According to Grodkowski et al., the rate limiting step is in the first single-electron oxidation while subsequent steps are markedly faster.

Because PEG-HCCs have a stable radical, it is not unlikely that PEG-HCCs are reduced by NADPH through an initial single-electron transfer. The proposed superoxide dismutase mechanism discussed by Samuel et al. involves an initial single electron reduction of the PEG-HCC by superoxide followed by a single electron oxidation of the PEG-HCC by superoxide to form hydrogen peroxide (FIG. 27), [Samuel 2015]. It may be possible that NADPH donates a single electron to the PEG-HCC then to the oxidized substrate.

Figure 30B:
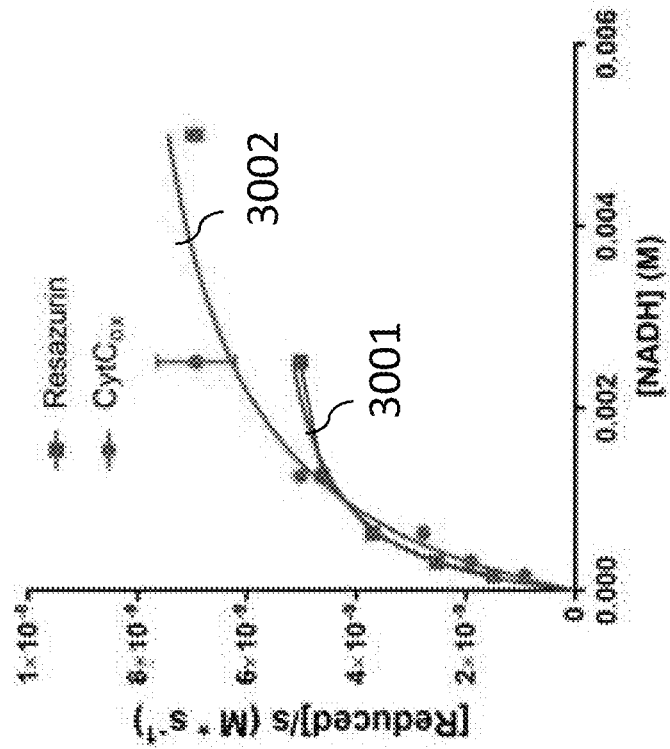
FIG. 30B is a graph showing the saturable catalyst kinetics of PEG-HCCs with respect to reducing resazurin to resorufin and ferricytochrome C to ferrocytochrome C by NADH.
Figure 30A:
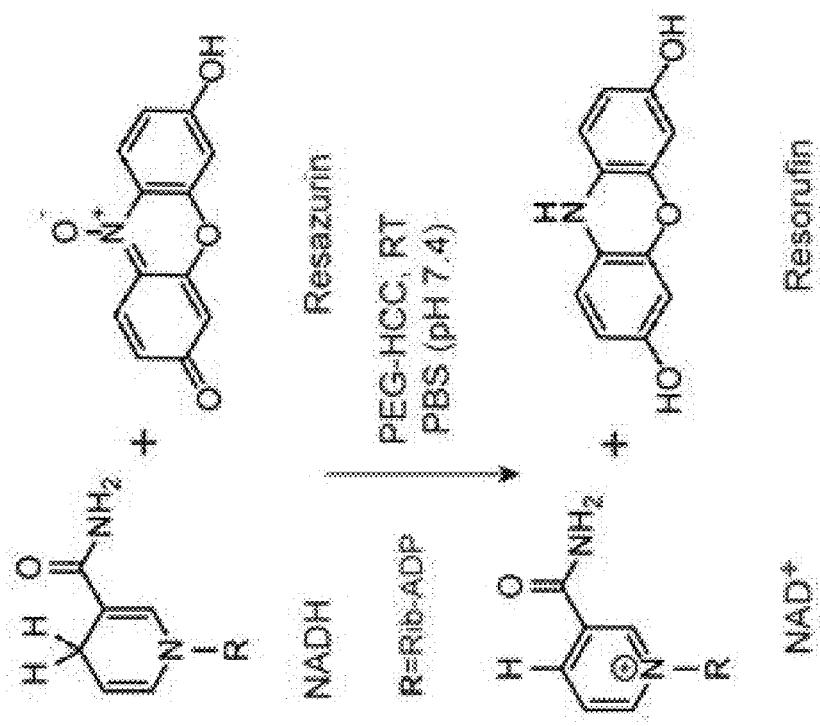
FIG. 30A is a scheme showing the reaction of NADH with PEG-HCCs and resazurin.

In the case of resazurin, the first step is the reduction of resazurin to an anionic radical followed by a second donation to reduce the radical to resorufin anion. This two-step reduction has been observed previously by Khazalpour and Nematollahi using a glassy carbon electrode [Khazalpour, S. et al., "Electrochemical study of Alamar Blue (resazurin) in aqueous solutions and room-temperature ionic liquid 1-butyl-3-methylimidazolium tetrafluoroborate at a glassy carbon electrode," *RSC Adv.* 2004, 4, 8431]. Additionally, NADH and NADPH do not readily reduce resazurin to resorufin except in the presence of light. Candeias et al. showed that N-methylphenazinium methosulfate (PMS) serves as a catalyst that can perform a single-electron transfer is necessary to reduce resazurin to resorufin with NADH or NADPH. [Candeias, L. P. et al., "The catalysed NADH reduction of resazurin to resorufin," *J. Chem. Soc. Perkin Trans.* 1998, 2 2333, 2333-2334]. Thus, it is expected that two-single electron reductions of the PEG-HCCs lead to two single electron reductions of the resazurin to form resorufin. It appears that the extended aromatic domain of the PEG-HCCs may facilitate electron transfer to distant reactive sites on the particle. As mentioned above, superoxide may also contribute in the photochemical reaction with riboflavin (FIG. 27). PEG-HCCs catalyze the reduction of resazurin by NADH in PBS to produce NAD+ and resorufin (FIG. 30A). PEG-HCCs function as saturable catalysts with enzyme-like kinetics with respect to the reduction of resazurin and cytochrome C by NADH. (FIG. 30B, curves 3001-3002 for resazurin and cytochrome C, respectively). Additionally, it was observed that PEG-HCCs also function as saturable catalysts for the reduction of resazurin by ascorbic acid (FIGS. 31A-31B, curves 3101-3102 for 40 µM, 20 µM, and 10 µM, respectively).

Effectiveness of PEG-HCCs Against the Toxic Effects of Cyanide in Tissue Culture It appears that PEG-HCCs can protect against acute cyanide poisoning. Toxic levels of sodium cyanide (NaCN) were applied in cultured brain endothelial cells (bEnd0.3) when assessed 24 hours after poisoning NaCN. The concentration of PEG-HCCs is based on prior data in mice and rats that do not demonstrate toxicity and are well tolerated.

Figure 32:
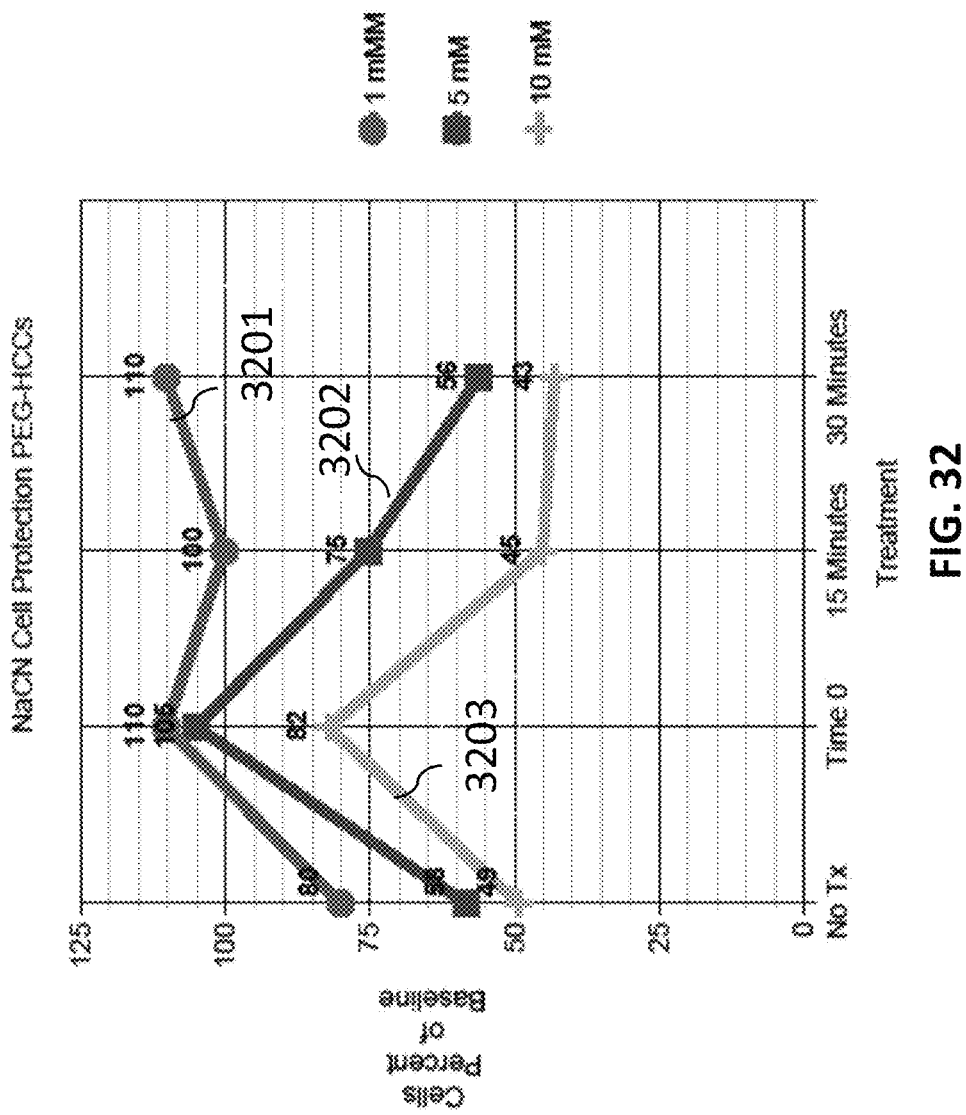
FIG. 32 is a graph showing protection against cell death after addition of sodium cyanide (NaCN) to cultured murine brain endothelial cells by PEG-HCCs.

FIG. 32 shows protection against cell death after addition of sodium cyanide (NaCN) to cultured murine brain endothelial cells by PEG-HCCs. Cell survival assessed 24 hours after addition of NaCN. Percent of cells that survive are on the Y-axis (percent of live cells at 24 hours compared to the baseline (in the absence of NaCN)). The X-axis is the treatment; either no PEG-HCCs. Time 0 is the result NaCN immediately after NaCN addition. 15 minutes is the result with PEG-HCCs added 15 minutes after NaCN. 30 minutes is the result with PEG-HCCs added 30 minutes after PEG-HCCs. Lines 3201-3203 are concentrations of NaCN of 1 mM, 5 mM, and 10 mM NaCN. These results indicate an extended time window after 1 mM, shorter with 5 mM and effectiveness when simultaneously treated with 10 mM.

The data shows that PEG-HCCs are protective against acute cyanide poisoning and shows a dose-response curve where higher cyanide concentration require faster administration of PEG-HCCs. In these experiments, 1 mM CN⁻ was utilized as the lowest dose because this approximates the $LD_{50}$ of CN⁻ exposure in humans. The continued protection at 30 minutes results suggest a time window may be outside the range of the experiment against the approximate $LD_{50}$ of CN⁻. At 5 mM NaCN, partial protection is still present up to 15 minutes for what approximates 5× the $LD_{50}$. There is partial protection present at 10 mM NaCN when administered immediately after the NaCN. Protection at this high dose when administered after the NaCN is quite remarkable.

It is believed that the window of efficacy and protection at higher NaCN can be extended by combination therapy, such as if a CN binding agent is utilized in conjunction with the PEG-HCCs (e.g., cobalamin derivatives).

Figure 33:
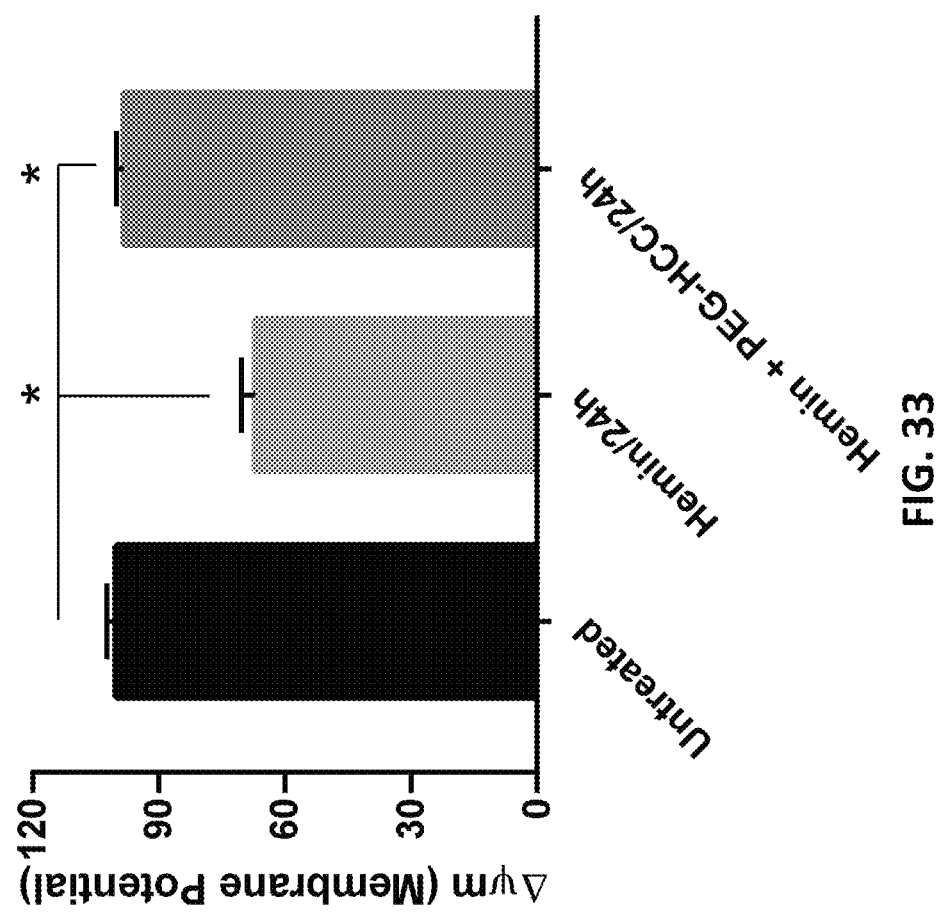
FIG. 33 is a graph showing protection against mitochondrial membrane potential reduction caused by hemin in cultured human neuroblastoma SHSY-5Y cells by PEG-HCCs.

Effectiveness of PEG-HCCs in Rescuing Mitochondrial Membrane Potential Against the Toxic Effects of Hemin in Tissue Culture The primary toxicant in hemorrhagic stroke is the blood hemoglobin-derived product hemin, which is a pro-oxidant heme-iron complex. FIG. 33 shows protection against mitochondrial membrane potential reduction caused by hemin in cultured human neuroblastoma SHSY-5Y cells by PEG-HCCs. Cells were plated in a 96-well plate and treated with 10 µM hemin for 1 h, followed by incubation with or without PEG-HCC for 24 h. Membrane potential was measured by fluorescence spectroscopy using TMRE-Mitochondrial Membrane Potential Assay Kit (Cat #ab113852, Abcam) following the manufacturer's protocol. Error bars represent SD from three independent measurements and * indicates $p<0.01$.

As shown in FIG. 33, hemin causes rapid ROS stress in mitochondria of neurons with 5 min of its exposure and leads a significant decrease in mitochondrial membrane potential, a key pathological process in hemin-mediated neuronal toxicity. Here, PEG-HCC was able to rescue the hemin mediated mitochondrial membrane potential reduction at 24 h to almost the basal level.

Uptake of DEF-PEG-HCCs by SHSY-5Y Cells

Uptake of DEF-PEG-HCC is illustrated in FIG. 34A-34B. SHSY-5Y cells expressing GFP with a cytochrome C targeting sequence have fluorescent mitochondria 3402 and can be used to show the structure of the mitochondria 3402 with a marker at a known target. These cells were treated with DEF-PEG-HCC 3401 and labeled those particles with anti-polyethylene glycol [PEG-B-47] rabbit monoclonal antibody followed by an AlexaFluor-647-conjugated anti-rabbit secondary antibody label to denote the location of the DEF-PEG-HCC 3401 within and outside the cell. FIG. 34A shows a Z-projection of the cells at 100× magnification using a deconvolution microscope. Mitochondria 3401, DEF-PEG-HCC 3402, and the nucleus 3403 are shown. FIG. 34B shows a section within a focal plane that crosses through the body of a cell showing that the DEF-PEG-HCC 3401 signal can come from within the cell body indicating uptake.

In addition to showing that the DEF-PEG-HCC 3401 particles are consumed by the cells, the colocalization of the particles with the mitochondria 3402 suggests that they are within the same volume as the mitochondria 3402 and thus likely the DEF-PEG-HCCs 3401 are internalized with the mitochondria 3402 supporting the mechanism shown in FIG. 23A.

FIG. 23A is an illustration of the KETS mechanism. The sources of pathological electron leakage in the electron transport chain (ETC) are shown in dashed arrows 2301. It appears that PEG-HCCs 2302 can function both as electron shuttles (shown by solid arrows 2303) and as superoxide dismutase 2315 mimetics (2303) depending on factors such as their location in the mitochondria 2304. Superoxide 2305, generated by Complex I, II, and III (2310-2312, respectively), is released into the mitochondrial matrix 2306 and the intermembrane space 2307. PEG-HCCs 2302 can accept electrons from superoxide 2305 and either (a) dismutate additional superoxide 2305 or (b) transfer electrons to cytochrome C 2308 when in the intermembrane space 2306. PEG-HCC 2302 can also accept electrons by NADPH 2309 in the matrix though at a much slower rate than Complex I 2301. After accepting electrons from NADPH, NADH, superoxide, or ubiquinone, PEG-HCCs 2302 may transfer electrons to cytochrome C 2308 or potentially to Complex IV 2312. Another source of electrons is ascorbic acid which is found in the intermembrane space 2307. Ascorbic acid may be used as an electron source for the PEG-HCCs to reduce superoxide into hydrogen peroxide 2316.

Utility

The utility of materials of the present invention that can not only act as high capacity antioxidants but also directly transport electrons and reduce key mitochondrial enzymes would have potential therapeutic advantages in a large range of conditions from rare mitochondrial disorders, accidental or deliberate exposure to toxins that poison complexes within the mitochondria and extremely common conditions such as ischemic and reperfusion injury and hemorrhage, all of which produce mitochondrial injury.

Cyanide poisoning is considered an orphan disorder by the US FDA. Cyanide inhibits the mitochondrial electron transport chain protein cytochrome C oxidase. Cyanide poisoning was therefore selected as a proof of principle condition in which a therapy that could directly reduce cytochrome c could provide a therapy. As discussed and taught above, evidence is shown regarding cyanide poisoning and a potential benefit in brain hemorrhage that generates toxic hemoglobin breakdown products such as hemin.

Cyanide poisoning is considered an orphan disorder by the US FDA. Cyanide poisoning occurs both deliberately in suicide and homicide, but also in sub-lethal exposures from house or industrial fires and contaminated water, such as that found near gold mining operations, and food. Survivors of cyanide poisoning often develop profound neurological impairments reminiscent of Parkinson's disease and experience other systemic impairments as well. In embodiments of the present invention, graphenic materials function as electron transport chain bypasses that allow both for electrons to flow between mitochondrial complexes and to quench superoxide and hydroxyl radical generated by the flavin and quinol species found either as electron shuttles or as prosthetic groups in the mitochondrial complexes.

The present invention addresses one of the shortcomings for the current therapeutic method for treating cyanide poisoning by providing an alternative source for electron transport to reduce permanent cellular damage. Additionally, other chronic mitochondrial disorders may also be treatable with these materials by providing an alternative pathway for electron transport through oxidative phosphorylation.

The ability to bypass normal electron transport pathway is an entirely new property of the materials of the present invention, which has previously been identified as possessing high capacity superoxide and hydroxyl radical quenching capabilities. It was, however, not known that they possess this additional function. This new discovery has profound implications for therapy of conditions in which OXPHOS dysfunction is central to the disorder as it addresses both the primary injury in addition to the free radical damaging consequences of this primary injury.

The electron bypass properties of these materials provide an alternative source to sequester or transfer electrons to oxidized antioxidant species, while their intrinsic antioxidant properties preserve the mitochondria until endogenous antioxidant cofactors, proteins and enzymes can be replenished. This discovery provides an exciting new tool in treatment of mitochondrial disorders.

The current art for cyanide poisoning therapy is primarily focused on directly binding cyanide or reducing cyanide's affinity for iron. Hydroxocobalamin is used to bind cyanide but does not have free radical scavenging properties on its own. The approach described and taught herein is an improvement on current art because it directly addresses electron leakage from the mitochondrial complexes in the electron transport chain by quenching the ROS that are inevitably generated.

One novelty of embodiments of the present invention is that it reduces the toxicity of cyanide by quenching ROS and providing a secondary route for electrons as opposed to the conventional ligand affinity method employed with hydroxocobalamin. Additionally, the graphenic carbon materials can be used acutely to treat cyanide poisoning both by itself and in combination with current therapies such as hydroxocobalamin derivatives in a two-pronged defense both to bind cyanide and quench the subsequent reactive oxygen species that are produced. This cocktail approach follows in the footsteps of highly active antiretroviral therapy (HAART) by addressing multiple causes in a single therapeutic step and may then be an excellent combination therapy.

The current art for treating chronic mitochondrial disorders is to supplement mitochondrial function with essential cofactors such as ubiquinone or cardiolipin, or electron transport mediators such as methylene blue and its derivatives.

Steps and Variations

In the most typical application of treating cyanide exposure: a person, animal, or cultured cell is first exposed to a cyanide-containing or cyanide-generating substance either intentionally or accidentally through any delivery mechanism. After exposure, the graphenic materials are administered either intravenously if available, or intra-muscularly if the intravenous option is not available to the poisoned individual. In the case of inherited or other acquired chronic mitochondrial disorders, the individual would be administered the graphenic material in ways to be determined and optimized by manipulation of side chains and PEGylation to provide a convenient chronic form.

The electron transport shuttle does not itself generate the proton gradient necessary for mitochondrial function. However, it is uncertain that the materials of the present invention are unable to interact with the proton-generating species since they demonstrate such excellent efficacy. Even if they do not themselves restore the proton gradient in the mitochondria, it is believed that prolongation of mitochondrial survival will permit restoration of endogenous complexes, factors and antioxidants to permit restoration of the proton gradient over time.

In the treatment of poisoning, because cyanide is a fast-acting poison, the therapeutic timespan is short. However, because even sub-lethal poisoning causes permanent damage, this intervention will save many lives and improve outcomes.

Microscopic work shows that PEG-HCCs are widely distributed within (and/or in close proximity to) cells including mitochondria. Probably higher than ultimately necessary concentrations were employed, which could be reduced with effective mitochondrial targeting. Versions of graphenic materials with mitochondria targeting ligands will be developed and tested.

It is expected that a variety of substances may be able to function in the same role as the PEG-HCCs.

It is further expected that graphenic materials or materials with SOD-like behavior and molecular weights ranging between 200 and 500,000 daltons can be useful in the present invention.

The graphenic materials can be of the form of single-walled nanotubes, double-walled nanotubes, triple-walled nanotubes, multi-walled nanotubes, ultra-short nanotubes, graphene, graphene nanoribbons, graphite, graphene oxide, graphene oxide nanoribbons, carbon black, oxidized carbon black, hydrophilic carbon clusters, graphene quantum dots, carbon dots, coal, coke, or combinations thereof. Such graphenic materials can be doped with heteroatoms. The heteroatoms can be O, N, S, P, B, and combinations thereof.

It is further expected that these materials will undergo post-synthetic modifications to include functional groups that tune the reduction-oxidation potential of the materials.

Post-synthetic modifications may include, but are not limited to, the inclusion of quinones, stable radicals, halides, nitrates, dihydrides, hydrogen atom donors, sulfur-containing groups, phosphorous-containing groups, amines, aromatic groups, and carbonyl-containing groups.

Poly(ethylene glycol) can be replaced with other polymers to modify solubility and stability in serum. Additional functionality of PEG-HCCs and GQDs can be achieved through simple amide conjugation chemistry. Small molecule quinones and perylene diimides (PDIs) could do the same thing as these PEG-HCCs.

Mixtures of the small molecule systems might be an advantage to encourage a wide range of reduction potentials from near 0 V to −1 V.

To obtain a greater level of target specificity, mitochondrial targeting labels can be used to increase selective uptake of these compounds by mitochondria. Furthermore, additional targeting moieties may allow the directed targeting of specific cell types depending on expressed receptors to limit the effects of these materials to specific tissues.

The ability to shuttle electrons in cells and in cell free culture has been shown. The rescue of cultured murine bEnd0.3 endothelioma cells from cyanide toxicity in vitro has also been demonstrated (bench scale application).

In terms of the effect in proton gradient, it can be important to measure the oxygen consumption and ATP formation activity measurements for isolated mitochondria (or submitochondrial particles) at Stage I-IV respiration with or without specific inhibitor and assess the possible role of the nanomaterial to bypass electron-transfer and maintain partial ATP production activity and to show the efficacy of the nano-antioxidant of the present invention relative to other agents used to treat mitochondrial pathology.

Catalytic Carbon Nano-Antioxidant in Mild Experimental Traumatic Brain Injury

Hypotension worsens outcome after all severities of traumatic brain injury (TBI), with loss of cerebral autoregulation a potential contributor. There are multiple phases of expression of reactive oxygen species associated with the initial injury, first at hypotensive shock and then upon resuscitation at blood infusion. The later burst of superoxide radical comes at a therapeutically relevant time, given that this is also the time when a medication could realistically be administered. A carbon nanomaterial, poly(etheylene)glycol conjugated hydrophilic carbon clusters (PEG-HCCs) treated at a clinically realistic time point was found to prevent a major portion of the neurological injury induced in this mild TBI model complicated by hypotension. PEG-HCC can thus be used to overcome many of the limitations of prior antioxidant strategies by improving outcome in this paradigm of high clinical relevance.

Operative Procedure

A total of 38 Long Evans rats, weighing 300-350 g, were used. The TBI model used was a mild cortical impact injury (3 m/s, 2.5 mm deformation) followed by 50 min of hemorrhagic hypotension. The rats were randomly assigned to receive either PEG-HCC (2 mg/kg, n=21) or saline as placebo (n=17). The assigned study drug was given intravenously at the beginning of resuscitation and again 2 hours after the first dose.

General anesthesia was induced using 5% isoflurane in 100% oxygen, by placing the rats in a vented anesthesia chamber for approximately 3-5 min. After anesthesia induction, the animals were intubated with a 14 gauge angiocath and mechanically ventilated using a volume-controlled ventilator. A surgical plane of anesthesia was maintained throughout the impact injury and period of hypotension with 2% isoflurane.

Under aseptic techniques, intravascular catheters were placed in the tail artery and femoral vein. The tail artery was dissected through a 2-4 mm, in length, incision in the proximal segment of the tail and cannulated using a 22 gauge angiocath Teflon catheter to monitor blood pressure. Through a 5-8 mm, in length, incision in the left groin, the femoral vein was dissected free and cannulated using a 22 gauge angiocath Teflon catheter to allow for the controlled hemorrhagic shock and resuscitation using Lactated Ringer solution or the shed blood. The catheters were secured to the skin with nylon sutures. After catheterization, the animals were mounted in a stereotactic frame in the prone position with the head secured by ear bars and an incisor bar. Body temperature was monitored and kept between 36-37° C. with a heating pad controlled by a rectal probe.

The scalp was shaved and cleaned using an iodine-based solution. The surgical field was draped with sterile linens. A medial sagittal skin incision was performed and the scalp (including the periosteum) and the temporalis muscle were reflected. To expose the brain for the impact injury, a 10 mm diameter craniectomy was performed over the right parietal cortex between the bregma and lambda using a dental drill. Care was taken to not injure the dural surface. A small amount of saline solution was directed at the site of drilling to prevent thermal injury to the brain tissue. With the impactor rod locked in the extended position, the impactor tip was centered in the craniectomy site perpendicular to the exposed surface of the brain at an angle of approximately 45° to the vertical, and then the tip was lowered until it just touched the dural surface. The impactor rod was then retracted, and the tip advanced an additional distance in order to produce a brain deformation of 2.5 mm at the time of the impact. To induce a mild level of traumatic injury, the controlled cortical impact device was adjusted to 30 psi giving an impact velocity of approximately 3 m/s. With the help of a heating lamp aiming at the head of the animal, the brain temperature was kept between 36-37° C. using a temperature probe placed into the temporalis muscle. After cortical injury, the skull defect was closed by using an artificial bone flap, composed of dental acrylic, to avoid extrusion of brain tissue.

Using a mechanical standard infusion/withdrawal pump (Harvard Pump Dual RS-232), blood was withdrawn to reduce the mean arterial pressure (MAP) to approximately 40 mmHg for a period of 50 min. The blood volume required to decrease MAP to such level was ~2 mL/100 g of weight. Half of this volume was withdrawn in the first 5 min, another 25% over the next 5 min, and the final 25% over the next 5 min. This decelerating rate of blood loss mimics the clinical situation of traumatic blood loss. Animals were kept hypotensive for the remaining hypotensive period if necessary by continued intermittent hemorrhage. The shed blood was collected into citrate phosphate dextrose and kept at 4° C. for the duration of the hypotensive and fluid resuscitation period. The shed blood was rewarmed to body temperature (36-37° C.) just prior to reinfusion. Following the assigned hypotensive period, animals were first resuscitated with Lactated Ringer solution using the infusion pump to maintain a constant infusion rate of 1 mL/min until a MAP of at least 50 mmHg was obtained. The final resuscitation was accomplished by reinfusion of the shed blood and providing 100% oxygen ventilation.

After the final resuscitation, anesthesia was discontinued to allow animals to recover. Escape, righting, head support, corneal, pinna, paw and tail reflexes were assessed every 1 min for 30 min once the rats were extubated and breathing spontaneously following termination of anesthetic. When fully awake, the animals were returned to their cages and allowed free access to food and water. For the first 3 days post-injury, the animals were given buprenorphine 0.1 mg/kg IM q12h for analgesia, and enrofloxacin 5 mg/kg IM qd to prevent postoperative infections.

Each rat was weighed on the day of beam walking pre-training, the day of surgery, days 1-5 post-surgery, and days 11-15 post-surgery using a digital scale. On days 1-5 post-injury, the animals were tested on the beam-walking and beam-balancing tasks. On days 11-15 post-injury, the animals were tested on the Morris water maze task. Following the last behavioral assessment, the animals were euthanized and the brains removed for histological examination.

Motor Tasks

Beam walking task. Each rat was pre-trained 2 days before surgery to walk down a beam 1 m long, 2.5 cm wide, and 1 m above the ground into a darkened goal box to escape white noise of 90 db. At the beginning of each training and test trial, the rat sat in the goal box for 30 s. During training trials, the rat was placed at successively longer distances from the goal box until it learned to walk down the entire beam. Any distance from which the rat did not walk down the beam into the goal box was repeated until it did. The rat was given a 30 s rest period in the goal box between trials. After it had traversed the beam in 5 s or less on three successive trials, four plastic pegs (7.5 cm high) were placed in holes in the beam at approximately 20-cm intervals alternating from side to side, 5 mm in from the edge of the beam. The rat was then trained to another criterion of three consecutive trials completed in 10 s or less. If both of these criteria were not met by 30 trials, the rat was disqualified. The final criterion for inclusion in the study was beam-walking times on the day of surgery with the pegs present that were 5 s or less on three consecutive trials within 15 trials. Beam walking with the pegs present was assessed on days 1-5 post-injury.

Beam balancing task. Each animal was placed lengthwise along the center of a beam 1.5 cm wide, 1 m long and 1 m above the ground. The rat attempted to balance on the beam for up to 60 s on each of three trials on the day of surgery and on days 1-5 post surgery. The rat was taken off the beam and placed in the goal box for 30 s between trials.

Histology

At 2 weeks after the impact, the animals were deeply anesthetized, and perfused transcardially with 0.9% saline, followed by 10% phosphate-buffered formaldehyde. The entire brain was removed and fixed in 4% formalin. The fixed brains were examined grossly for the presence of contusion, hematoma, and herniation. The brains were photographed, sectioned at 2-mm intervals, and then embedded in paraffin. Hematoxylin and eosin-stained sections were washed with 0.9% saline, followed by 10% phosphate-buffered formaldehyde. The brain sections were photographed using a section scanner (Polaroid Corporation, Waltham, MA) equipped with a PathScan Enabler (Meyer Instruments, Houston, TX). The injury volume was measured by determining the cross-sectional area of injury in each coronal image and multiplying by the thickness of the tissue between the slices. This slab volume technique was implemented on the image-processing program Optimas 5.2 (Optimas Corporation, Seattle, WA).

Neurons in the middle 1-mm segments of the CA1 and CA3 regions of the hippocampus were counted at a magnification of 200×. Neurons were identified by nuclear and cytoplasmic morphology, and individual cells were counted as either normal or damaged. Neurons with cytoplasmic shrinkage, basophilia, or eosinophilia, or with loss of nuclear detail were regarded as damaged. The regions measured were 1 mm long and 1 mm wide (0.5 mm on either side of the long axis of the segment). The total number of neurons and the number of neurons that seemed normal were expressed as neurons per square millimeter.

Results

These results reflect that PEG-HCC treatment at the time of "definitive resuscitation" in a mild TBI model combined with hypotension and resuscitation improves functional outcome and brain structure.

Figure 35:
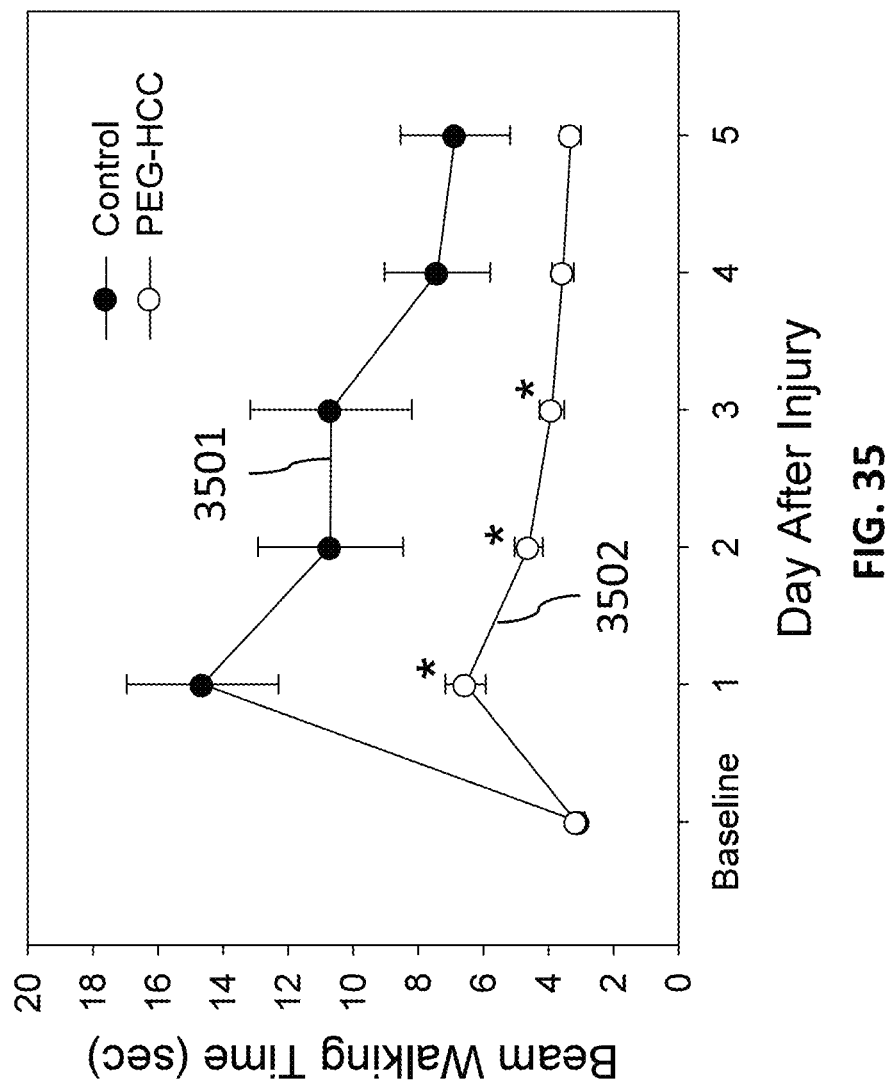
FIG. 35 is a graph that shows the performance on the beam walking task of the test group of rats (injured, untreated treated with saline (vehicle treated, negative control) and injured, treated with PEG-HCCs).

FIG. 35 plots the performance on the beam walking task of the test group of rats (plots (TBI) 3501-3502, respectively for the control and those treated with PEG-HCC). The performance on the beam walking task was significantly better in the PEG-HCC treated group (treatment effect, p=0.007; treatment×day interaction, p<0.001). The asterisks on FIG. 35 indicate values that are significantly different from the control group (p<0.05, Holm-Sidak method.

Figure 36:
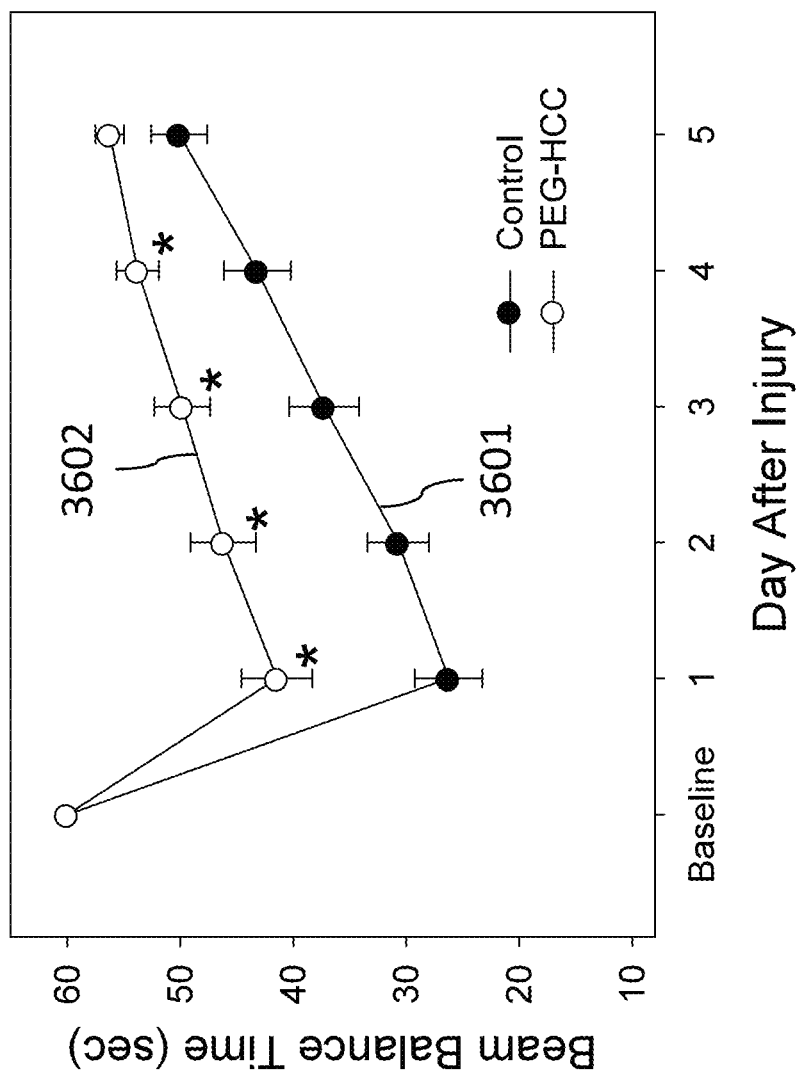
FIG. 36 is a graph that shows the performance on the beam balance task of the test group rats (injured treated with saline (vehicle treated, negative control) and injured treated with PEG-HCC).

FIG. 36 plots the performance on the beam balance task of the test group rats (plots 3601-3602, respectively for the control and those treated with PEG-HCC). The performance on the beam balance task was significantly better in the PEG-HCC treated group (treatment effect, p<0.001; treatment×day interaction, p<0.001). The asterisks on FIG. 36 indicate values that are significantly different from the control group (p<0.05, Holm-Sidak method).

Figure 37:
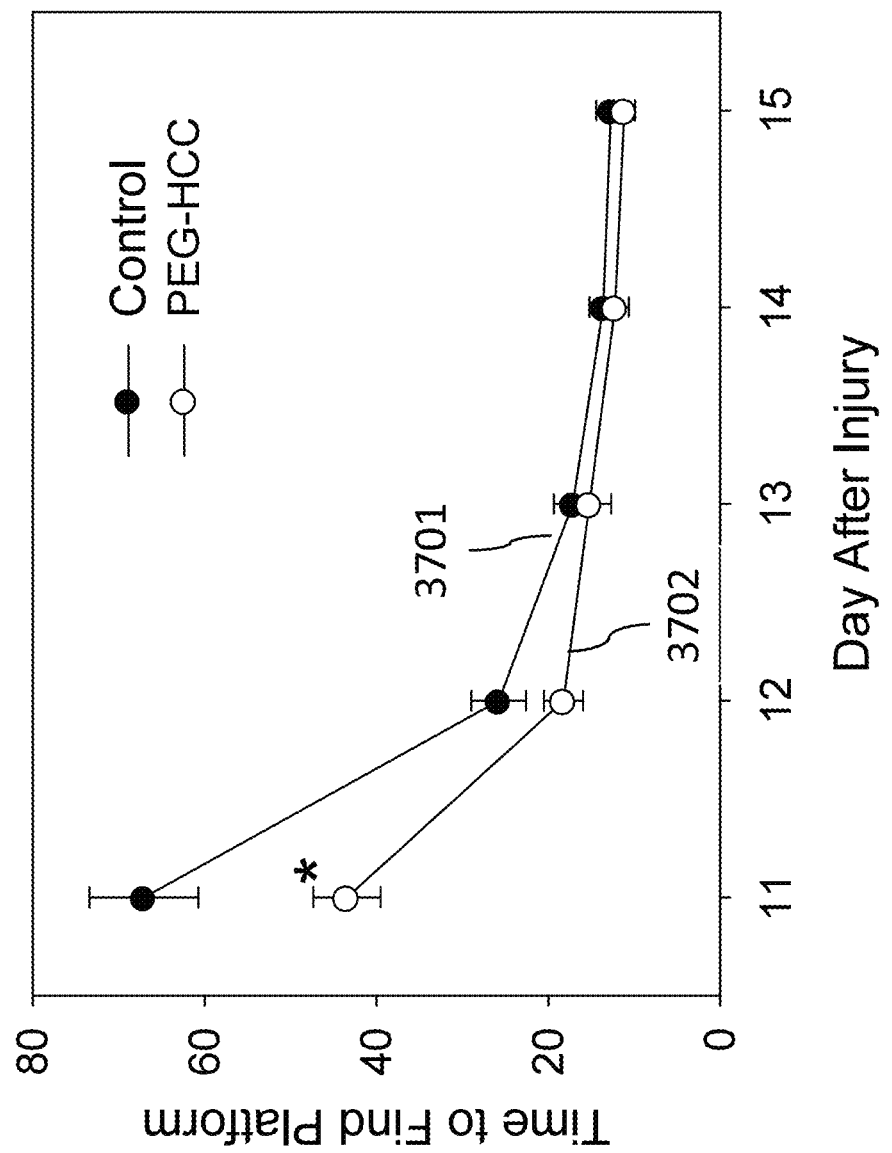
FIG. 37 is a graph that shows the performance on the Morris water maze task of the test group rats (injured treated with saline (vehicle treated, negative control) and injured treated with PEG-HCC).

FIG. 37 plots the performance on the Morris water waze task of the test group rats (plots 3701-3702, respectively for the control and those treated with PEG-HCC). The performance on the Morris Water Waze task was significantly better in the PEG-HCC treated group in the early testing time period (treatment effect, p=0.010; treatment×day interaction, p<0.001). The asterisks on FIG. 35 indicate values that are significantly different from the control group (p<0.05, Holm-Sidak method).

Figure 38:
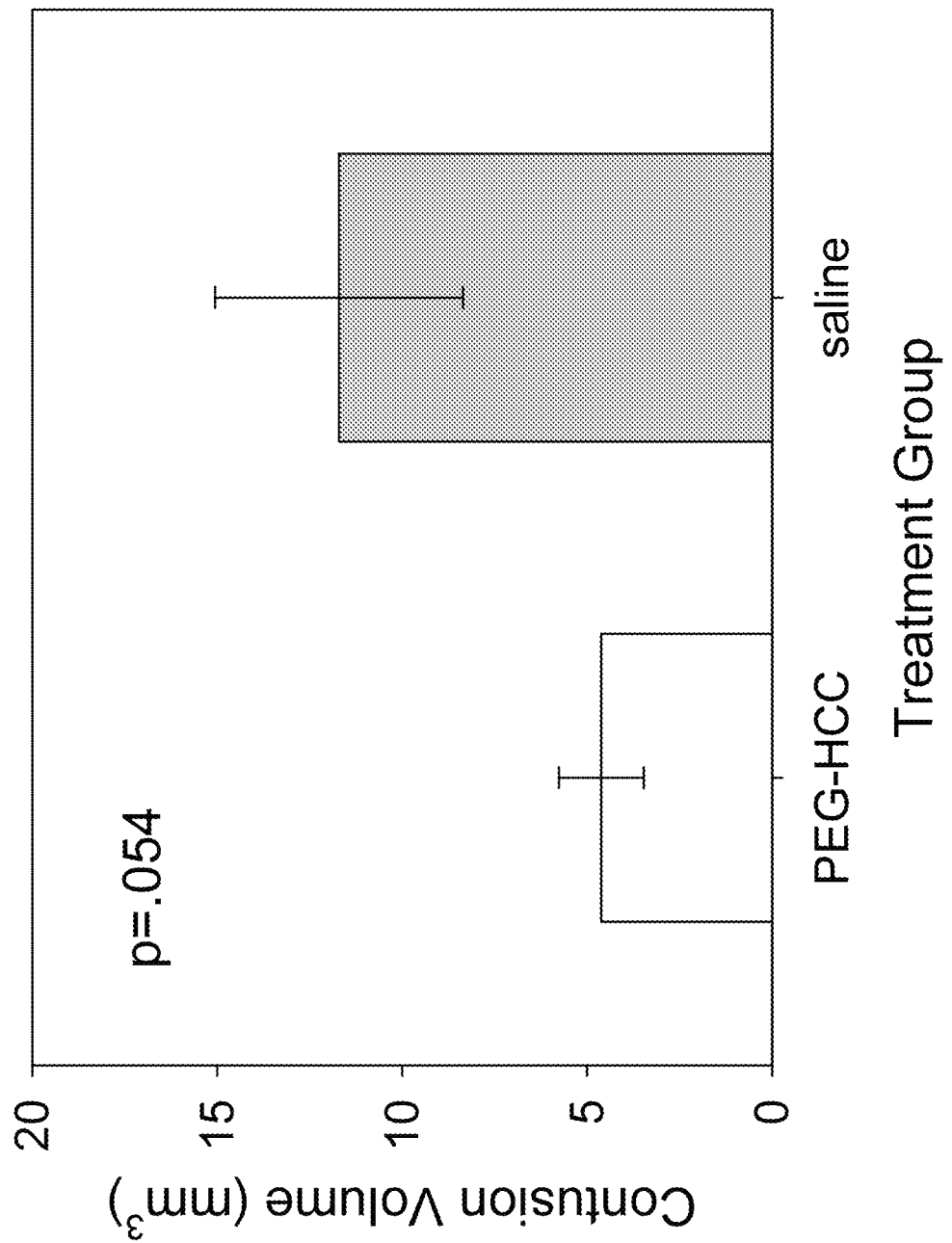
FIG. 38 is a graph that shows the contusion volume at 2 weeks post-injury of the test group of rats treated with saline (vehicle treated, negative control) and PEG-HCC.

FIG. 38 plots the contusion volume at 2 weeks post-injury of the test group of rats. The contusion volume was much less (thus significantly better) in the PEG-HCC treated group.

As these results reveal, PEG-HCCs, given at the onset of definitive resuscitation and repeated 2 hours later, improved measures of functional outcome and reduced lesion size. The exacerbating effect of hypotension revealed that there is a major vascular component to TBI that is brought out by hypotension. Loss of cerebral autoregulation even with mild TBI is likely a factor, and there is evidence, through pre-treatment with antioxidants, that oxidative stress contributes to this phenomenon. It has been shown that, when treated at the time of "definitive" resuscitation, the treatment was highly efficacious both structurally and functionally, showing that viable tissue is salvageable.

While embodiments of the invention have been shown and described, modifications thereof can be made by one skilled in the art without departing from the spirit and teachings of the invention. The embodiments described and the examples provided herein are exemplary only, and are not intended to be limiting. Many variations and modifications of the invention disclosed herein are possible and are within the scope of the invention. Accordingly, other embodiments are within the scope of the following claims. The scope of protection is not limited by the description set out above.

The disclosures of all patents, patent applications, and publications cited herein are hereby incorporated herein by reference in their entirety, to the extent that they provide exemplary, procedural, or other details supplementary to those set forth herein.

Various terms are used to refer to particular system components. Different companies may refer to a component by different names—this document does not intend to distinguish between components that differ in name but not function. In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection or through an indirect connection via other devices and connections.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, the term "and/or" when used in the context of a listing of entities, refers to the entities being present singly or in combination. Thus, for example, the phrase "A, B, C, and/or D" includes A, B, C, and D individually, but also includes any and all combinations and sub-combinations of A, B, C, and D.

Concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a numerical range of approximately 1 to approximately 4.5 should be interpreted to include not only the explicitly recited limits of 1 to approximately 4.5, but also to include individual numerals such as 2, 3, 4, and sub-ranges such as 1 to 3, 2 to 4, etc. The same principle applies to ranges reciting only one numerical value, such as "less than approximately 4.5," which should be interpreted to include all of the above-recited values and ranges. Further, such an interpretation should apply regardless of the breadth of the range or the characteristic being described.

Following long-standing patent law convention, the terms "a" and "an" mean "one or more" when used in this application, including the claims.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that can vary depending upon the desired properties sought to be obtained by the presently disclosed subject matter.

What is claimed is:

1. A therapeutic composition comprising an antioxidant nanoparticle covalently modified with a chelating moiety, wherein
   (a) the antioxidant nanoparticle has both antioxidant and pro-oxidant properties;
   (b) the therapeutic composition is operable to act as a high capacity oxidant having an oxygen radical absorbance capacity value between 200 and 15,000 and directly transports electrons and reduces key mitochondrial enzymes when administered to a subject;
   (c) the therapeutic composition has a chelation efficacy that is at least ten times greater as compared to a same amount of the chelating moiety without the antioxidant nanoparticle;
   (d) the chelating moiety is a metal-chelating moiety; and
   (e) the metal-chelating moiety is a chelator of a metal selected from a group consisting of aluminum, americium, arsenic, cadmium, cesium, chromium, copper, curium, iron, lead, mercury, plutonium, thallium, uranium, and zinc, wherein
(i) the chelating moiety is deferoxamine (DEF),
(ii) the antioxidant nanoparticle is selected from a group consisting of poly(ethylene glycol)-hydrophilic carbon clusters (PEG-HCCs), poly(ethylene glycol)-ylated graphene quantum dots (PEG-GQDs), and poly(ethylene glycol)-ylated perylenediimide (PEG-PDI),
(iii) the therapeutic composition is selected from a group consisting of deferoxamine poly(ethylene glycol)-hydrophilic carbon clusters (DEF-PEG-HCCs), deferoxamine poly(ethylene glycol)-ylated graphene quantum dots (DEF-PEG-GQDs), and deferoxamine poly(ethylene glycol)-ylated perylenediimide (DEF-PEG-PDI), and
(iv) ratio of poly(ethylene glycol) (PEG) to chelating moiety is between 1:3 and 3:1.

2. The therapeutic composition of claim 1, wherein the therapeutic composition has a chelation efficacy that is at least 100 times greater as compared to a same amount of the chelating moiety without the antioxidant nanoparticle.

3. The therapeutic composition of claim 1, wherein the metal is selected from a group consisting of arsenic, cadmium, copper, iron, lead, zinc, and combinations thereof.

4. The therapeutic composition of claim 1, wherein the therapeutic composition is operable to treat or reduce mitochondrial injury.

* * * * *